United States Patent [19]
Blume

[11] Patent Number: 6,010,861
[45] Date of Patent: *Jan. 4, 2000

[54] TARGET SPECIFIC SCREENS AND THEIR USE FOR DISCOVERING SMALL ORGANIC MOLECULAR PHARMACOPHORES

[75] Inventor: Arthur J. Blume, Montclair, N.J.

[73] Assignee: DGI BioTechnologies, LLC, Edison, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/473,105

[22] Filed: Jun. 7, 1995

Related U.S. Application Data

[63] Continuation-in-part of application No. 08/286,084, Aug. 3, 1994, abandoned.

[51] Int. Cl.⁷ .............................. G01N 33/53; E12Q 1/68; C12Q 21/06
[52] U.S. Cl. .............................. 435/7.1; 435/69.1; 435/6; 436/536
[58] Field of Search ................... 436/536; 435/6, 435/7.1, 69.1

[56] References Cited

U.S. PATENT DOCUMENTS

| | | |
|---|---|---|
| 4,593,002 | 6/1986 | Dulbecco . |
| 4,797,363 | 1/1989 | Teodorescu et al. . |
| 4,818,684 | 4/1989 | Edelman et al. . |
| 4,859,609 | 8/1989 | Dull et al. . |
| 4,946,778 | 8/1990 | Ladner et al. . |
| 4,962,777 | 10/1990 | Cuervo et al. . |
| 4,963,263 | 10/1990 | Kauvar . |
| 5,030,576 | 7/1991 | Doll et al. .............................. 435/69.7 |
| 5,133,866 | 7/1992 | Kauvar . |
| 5,144,010 | 9/1992 | Erlanger et al. . |
| 5,217,869 | 6/1993 | Kauvar . |
| 5,230,998 | 7/1993 | Neurath et al. .......................... 435/7.1 |
| 5,264,563 | 11/1993 | Huse . |
| 5,300,425 | 4/1994 | Kauvar . |
| 5,322,699 | 6/1994 | Wright et al. . |
| 5,403,484 | 4/1995 | Ladner et al. ........................ 435/251.1 |
| 5,418,135 | 5/1995 | Pang ......................................... 435/7.1 |
| 5,427,908 | 6/1995 | Dower et al. .............................. 435/5 |
| 5,488,099 | 1/1996 | Persohn et al. .......................... 530/399 |
| 5,576,423 | 11/1996 | Aversa et al. . |
| 5,591,831 | 1/1997 | Feldman et al. . |
| 5,597,920 | 1/1997 | Shaw et al. . |
| 5,602,024 | 2/1997 | Gerald et al. . |
| 5,605,911 | 2/1997 | Olney et al. . |

FOREIGN PATENT DOCUMENTS

| | | |
|---|---|---|
| 0239400 | 9/1987 | European Pat. Off. . |
| 0328404 | 8/1989 | European Pat. Off. . |
| 0338745 | 10/1989 | European Pat. Off. . |
| 0368684 | 5/1990 | European Pat. Off. . |
| 0523949 | 1/1993 | European Pat. Off. . |
| 0528469 | 2/1993 | European Pat. Off. . |
| WO-A-8807089 | 9/1988 | WIPO . |
| WO-A-8903430 | 4/1989 | WIPO . |
| WO-A-8909233 | 10/1989 | WIPO . |
| WO-A-9002809 | 3/1990 | WIPO . |
| WO-A-9110907 | 7/1991 | WIPO . |
| WO-A-9117271 | 11/1991 | WIPO . |
| WO-A-9119739 | 12/1991 | WIPO . |
| WO-A-9119818 | 12/1991 | WIPO . |
| WO-A-9201047 | 1/1992 | WIPO . |
| WO-A-9201787 | 2/1992 | WIPO . |
| WO-A-9206176 | 4/1992 | WIPO . |
| WO-A-9206204 | 4/1992 | WIPO . |
| WO-A-9211272 | 7/1992 | WIPO . |
| WO-A-9220791 | 11/1992 | WIPO . |
| WO-A-9412215 | 6/1994 | WIPO . |
| WO-A-9418219 | 8/1994 | WIPO . |

OTHER PUBLICATIONS

F. Breitling, et al., "A Surface Expression Vector for Antibody Screening", Gene, 104, 1991, 147–153.
G. Winter, et al., "Making Antibodies by Phage Display Technology", Annu. Rev. Immunol., 1994, 12:433–55.
A.D. Griffiths, et al., "Isolation of High Affinity Human Antibodies Directly from Large Synthetic Repertoires", The Embo Journal, No. 14, 1994, 13:3245–3260.
M. Figini, et al., In Vitro Assembly of Repertoires of Anitbody Chains on the Surface of Phage by Renaturation, J. Mol. Biol., 1994, 239:68–78.

(List continued on next page.)

*Primary Examiner*—Paula Hutzell
*Assistant Examiner*—Susan Ungar
*Attorney, Agent, or Firm*—Morgan & Finnegan, L.L.P.; Kenneth H. Sonnenfeld

[57] ABSTRACT

The invention relates to a general process by which recombinantly derived variable domains of antibodies encompassing either or both light and heavy variable regions with or without respective constant regions are engineered and selected for identification of unique surface domains of pharmaceutical targets or parts thereof which regulate target function. The recombinant antibodies are useful as reagents for high volume, rapid screening of occupation of the active surface domains by natural or synthetic entities. This invention is also directed to elucidating the three dimensional conformation of the antibodies, or parts thereof, which bind to the pharmaceutical targets and confers activity. Methods for creating high resolution molecular models which can direct the synthesis of biologically active small organic molecules useful as viable discovery drug leads are also provided.

33 Claims, 32 Drawing Sheets

OTHER PUBLICATIONS

P.M. Colman, et al., "Three–Dimensional Structure of a Complex of Antibody With Influenza Virus Neuraminidase", Nature, 1987, 326:358–363.

W.R. Tulip, et al., "Crystal Structures of Two Mutant Neuraminidase–Antibody Complexes With Amino Acid Substitutions in the Interface", J. Mol. Biol., 1992, 227:149–159.

A. Nissim, et al., "Antibody Fragments from a 'Single Pot' Phasae Display Library as Immunochemical Reagents", The Embo Journal, No. 3, 1994, 13:692–698.

Lei Jin, et al., "Structure From Function: Screening Structural Models with Functional Data", Proc. Natl. Acad. Sci. USA, 1994, 91:113–117, Biochemistry.

C.S. Ring, et al., "Structure–Based Inhibitor Design by Using Protein Models for the Development of Antiparasitic Agents", Proc. Natl. Acad. Sci. USA, 1993, 90:3583–3587, Biophysics.

T.E. Ferrin, et al., "The Midas Display System", J. Mol. Graphics, 1988, 6:13–27.

E.C. Meng, et al., "Automated Docking with Grid–Based Energy Evaluation", J. Computational Chem., No. 4, 1992, 13:505–524.

J.L. Wrana, et al., "Mechanism of Activation of the TGF–β Receptor", Nature, 1994, 370:341–347.

R. Peters, et al., "Three–Dimensional Modeling and Drug Development", Bio/Technology 1994, 12:147–150.

K.A. Chester, et al., "Phage Libraries for Generation of Clinically Useful Antibodies", Lancet 1994, 343:455–456.

Tai Te Wu, et al., "Length Distribution of CDRH3 in Antibodies", Proteins: Structure, Function, and Genetics 16:1–7 1993.

Huse et al (Science, 1989, 246: 1275–1281).

Klausner (Biotechnology 1986, 4: 1042–1043).

Winter & Harris (TIPS, 1993, 14: 139–143).

Cheldi et al (J. Immunol, 1989, 142: 4301–4306).

Helmes et al (Biochem, Cell, Biol. 1989, 67: 581–588).

Stanfield et al (Immunomethods, 3; 211–221, 1993).

Yamamura et al (Methods in Neurotransmitter Receptor Analysis Raven Press 1990, NY. pp. 1–68.

| STAGE | ACTIVITY | PRODUCT |
|---|---|---|
| Stage I | | |
| a. | Construct Recombinant Antibody Library | :rVab.lib |
| b. | Select rVab which Bind Target Specifically | :rVabTS+ |
| c. | Isolate rVabTS+ Which Regulate Target Activity | :rVabTSA+ |
| Stage II | | |
| a. | Convert rVabTSA+ to Labelled Active Surface Reporters one for each unit domain of the active site | :[*]rVabTSA+ |
| b. | Use [*]rVabTSA+ in Binding Assays to Isolate competing small organic molecules one for each Reporter of a active site unit domain | :SOMERS :SOMERS-$T_n$ |
| c. | confirm SOMER activity on Target at single domain active sites | :SOMER($T_1$+) |
| | at multiple domain active sites chemically linking SOMERS for each active site domain | :SOMER($T_1$-$T_n$) [= MULTIMER+] |
| Stage III | | |
| a. | Extract Structural Information from rVabTSA+ | : rVab InfoBase |
| b. | Create a Biological Enhanced Ensembled Pharmacophore (i.e., structures which Regulate Target Activity) one for each domain of the active site | :BEEP-$T_1$ :BEEP($T_{1-n}$) |
| c. | Find active SOMERS for Targets (using Computation Screens and Synthetic Efforts) with BEEP $T_1$ for single active domain of Target with BEEP-$T_{1-n}$ for multiple active domains and then chemically coupling SOMERS($T_1$-$T_n$) | :SOMER-$T_1$+ :SOMER-$T_{1-n}$* :MULTIMER+ |

FIG. 1

2A Antibody Structures:
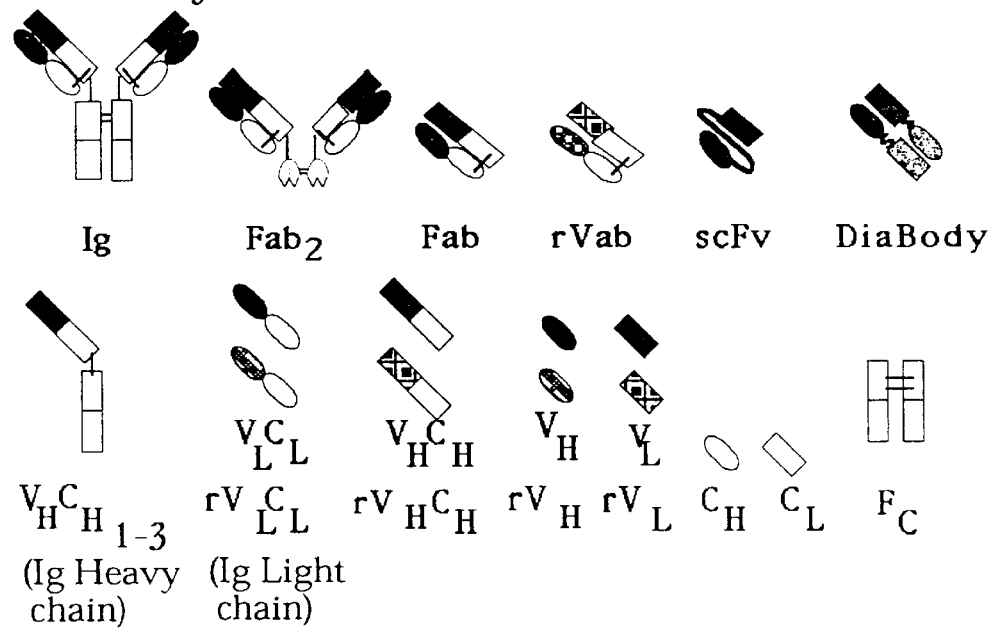
2B Variable Region Domains:
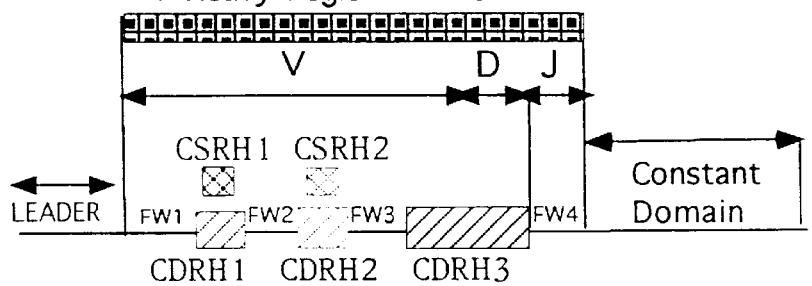
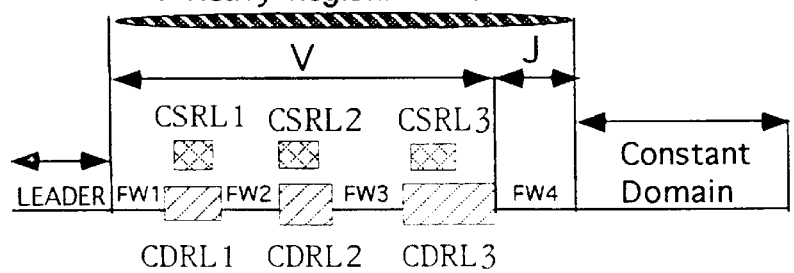
FIG. 2

| Combining Site Class | CDRH3 aaSize | CDRH3 Sequence* | Brkhvn Entry | Common Name | Type Antigen | Burried Surf.Area | VH-L IntrFce | VH-L Rotatn | Crstyl A Resoltn | AgContacts NonH3/To | Ref |
|---|---|---|---|---|---|---|---|---|---|---|---|
| cavity | 5 | DHG(.........)SD | | NQ10/12.5 | hapten | 170 | | | | | a,b |
| cavity | 10 | SSGNKWAM(.........)DY | 1ligi | 26-10 | hapten | | | | 2.7 | 6/10 | a,b |
| cavity | 6 | GWP(.........)LAY | 1baf | AN02 | hapten | | | | 2.9 | 5/7 | a,b |
| cavity | | | 1bbd | 8F5 | hapten | | | | | | a |
| cavity | 10 | GDYVNWPG(.........)DV | 1dba;b | DB.3nat;prog | hapten | 223-291 | 1425-1556 | ? | 2.8 | | a,b |
| cavity | | | | D7B2 | hapten | | | | | | a, |
| cavity | 7 | SYYGM(.........)DY | 4fab | 4-4-20 | hapten | 266 | 1375 | | | | a,b |
| cavity | 11 | | 1mcp | McPC603 | hapten | 137 | 1675 | | | | a |
| ? | 15 | FYYGGSHLAVYY(4)FDS | | R19.9 | carbohydrate | | | | 2.8 | 5/28 | a,b |
| ? | 9 | | jfbj | J539 | carbohydrate | | 1547 | | 1.95 | | a |
| ? | 12 | SEYYGGSYK(.........)FDY | 6FAB | 36-71 | hapten | | | | | | b |
| groove | 10 | YSSDPFYF(.........)DY | 1lgf;2lgf | B1312;n.1 | peptide | | 1409-1508 | | 2.8 | | a,b |
| groove | 11 | | 1lgf | B1312.n.2 | peptide | | 1537 | | | | a |
| groove | 11 | | 1hil;m,n | 17/9 | peptide | 400 | 1455-1545 | 2.3-4.2 | 2.0 | | a |
| groove | 5 | | 1ggi;b;c | 50.1 | peptide | 475 | 1063-1175 | 14.8-16.3 | 2.8 | | a,b |
| groove | 4 | | 1igm | POT | peptide(CTX) 503 | | | | 2.3 | | a |
| groove | 7 | | | TE33 | peptide | | | | 2.9 | 10/46 | a,b |
| groove | 9 | | 1mfb | MCG | saccharide | | | | | | a |
| ? | | | | SE115-4 | | | | | | | b |
| planar | 13 | SGGSYRYDGG(.........)FDY | | NC10 | protein(Neu) 716 | | | | | 9/12 | c |
| planar | 11 | GEDNFGSLS(.........)DY | 1nca | NC41 | protein(Neu) 879 | | | | | 8/13 | a,b |
| planar | 8 | RDYRL(.........)DY | 1fdl | D1.3 | protein(Lyz) 680 | | 1453 | | | 5/15 | |
| planar | a,b | | | | | | | | | | |
| planar | 5 | WDG(.........)DY | 3hfm | HeHel10 | protein(Lyz) 774 | | 1411 | | | 14/17 | a,b |
| planar | 7 | GNYD(.........)FDG | 2hfl | HyHel5 | protein(Lzy) 750 | | 1305 | | | 8/12 | a,b |
| planar | | | | FvD13.11 | protein | | | | | | a |
| planar | 8 | GLAFY(.........)FDH | 7fab | E225;antiD1.3 | protein(D1.3)800 | | 1483 | | 2.0 | | a,b |
| planar | 9 | QGTIAG(.........)JRH | 8fab | NEW | myeloma | | | | 1.8 | | a,b |
| ? | 12 | DPDLILTAPS(.........)DY | 1mam | HIL | myeloma | | | | 2.5 | | a,b |
| planar | 8 | | | YST9.1 | carbohydrate | | | | | | a |
| planar | 8 | | 2fbj | Jel318 | | | | | | | a,b |
| planar | 9 | | 1mcb | J539 | | | | | | | a,b |
| planar | 7 | | 1cbv | MCG | | | | | | | a,b |
| planar | 10 | DQDGTA(.........)WFAY | | BV04.01;nat | | | | | | | a,b |
| planar | a,b | | | | | | | | | | |
| ? | | | | dna | DNA | | 1387-1404 | 7.5 | | | a |
| ? | >8 | | | Jel72 | | | | | | | a,b |
| ? | 17 | | 2fb4 | KOL | | | 1612 | 1.9 | | | a,b |

Ag:Ab Contact are v.d.W., salt bridges and hydrogen bonds. Ref a=[Webster,Henry,Rees;1994]; b = [Wu,Johnson and Kabat;1993] and c = [Malby et.al. 1994 ] x/y= Ratio of aa contacts between aa of Ab not in CDRH3 (i.e., Non-CDRH3) and An to total aa contacts between Antibody(Ab) and Antigen(Ag) * = CDRH3 Sequence given as VH aa from position 95-102 using maximum CDRH3aa size as19 and with alignment (....) as used by Wu, Johnson and Kabat [1993]

FIG. 3

| NAME | L1 | L2 | L3 | H1 | H2 | H3 |
|---|---|---|---|---|---|---|
| CDR aa | | | | | | |
| Positions | [24-34] | [50-56] | [89-97] | [31-35] | [50-65] | [95-102] |
| Insertion Points | 27a-f | | 95a-c | 31ab | 52a-c | 100a-k |
| CSR | | | | | | |
| aa Positions | [26-32] | [50-52] | [91-96] | [26-32] | [52a-55] | - |
| # Known | 5 | 1 | 6 | 3 | 4 | 0 |
| Essential aa | | | | | | |
| in CSR | 29* | - | 94**,95* | 26*,27*,29* | 52a*,54**,55* | - |
| in CDR | 25*,33* | - | - | - | - | - |
| in FW | 2*,71* | 48*,69* | 90* | 34*,94* | 71* | - |
| Surface aa | 27-33 | 49-53 | 91-96 | 28-33 | 52,-58,60 | - |
| Buried aa | - | - | - | 34 | 51 | 96-100 |
| AA variance in CDR | | | | | | |
| κ mu | 30>31=28>29 | 50>>55>>53=51 | 94>92=91=93>96 | 35>33 | 50>52=53=54 | 95=96=100>97>98=99 |
| κ all | 28=31=34 | 50>>55>53=51 | 94>92-91=96>93 | 30=31=32=34 | - | - |
| λ all | 43>31=29>28=27 | 50>51=52=53 | 95>96>94=92 | - | - | - |
| κ,λ all | 27-31=34 | 50>>51=52 | 94>96=92>91=93 | 35>33>31 | 50>52=53=54 | 95=100>96>99=97=98 |
| Nonessential all | 28,30,31 | 50,51,52 | 94*,92,96,91,93 | 28,30,31,32 | 53,54 | - |
| Library Diversification | 28,30,31 | 52,50,53 | 91-94;95abc | 28,30,31 | 53,54 | 96-100a-k |

CSR= Canonical structure; CDR = complementary determining region of high variance; FWK= framework residues
Chothia and Lesk (1987); Chothia, et.al. (1989); Kabat,E.A., et.al. (1991); Chothia, C., et.al.(1992) andTomlinson, I.M.,et al (1992).

```
CANONICAL                       CDR
STRUCTURE                       CSR                                CSR    DIVERSITY
L1      KNOWN   2   24252627abc282930abc31abcdef323334  71  SIZE   P O S I T I O N
L1.1    YES     I*  + A*S S ---S V*+ ---- ------+ M*+       Y*     6AA    30,32
L1.2    YES     I*  + A*S Q ---S I*+ ---+ ------+ L*+       Y*     7AA    30,31
L1.3    YES     I*  + S*S E ---S L*+ ---+ SGNEKN+ L*+       Y*     13AA   30,31
L1.4    YES     V*  + S*Q S ---S L*+ ---+ S-NGNT+ L*+       F*     12AA   30,31
L1.5    YES     S   + G*S S ---S D*+ GS-+ ------+ L*+       A*     9AA    30,31
L1.6    NO      S   + G D N ---L N + ---+ ------+ V*+       A*     7AA    30,31

CANONICAL                       CDR
STRUCTURE                       CSR                                CSR    DIVERSITY
L2      KNOWN   4849    50515253545556         64           SIZE   P O S I T I O N
L2      YES     I*+     + + S + + + +          G*           3AA    5 0 , 5 1

CANONICAL                       CDR
STRUCTURE                       CSR                                CSR    DIVERSITY
L3      KNOWN   8990919293ABCDEF94959697                    SIZE   P O S I T I O N
L3.1    YES     + Q*+ + + ------+ P*+ +                     6AA    9 3 , 9 2
L3.2    YES     + Q*+ + + ------P*+ + +                     6AA    9 3 , 9 2
L3.3    YES     + Q*+ + + ------+ P*- +                     5AA    9 3 , 9 2
L3.4    YES     + Q*+ + + ------P-P-+ +                     6AA    9 3 , 9 2
L3.5    YES     + Q*+ + + ++----+ + + +                     8AA    9 3 , 9 2
L3.6    YES     + Q*+ + + +-----+ + + +                     7AA    9 3 , 9 2
```

2. VH

```
CANONICAL                       CDR
STRUCTURE                       CSR                                CSR    DIVERSITY
H1      KNOWN   2425262728293031ab323334       94           SIZE   P O S I T I O N
H1.1    YES     A*+ G*F*+ F*+ + --+ + M*                    R*     7AA    3 1 , 2 8
H1.2    YES     A*+ G*S*+ F*+ + --+ + W*                    R*     7AA    3 1 , 2 8
H1.3    YES     A*+ G*Y*+ F*+ + +-+ + W*                    R*     7AA    3 1 , 2 8
H1.4    NO      A*+ G*F*+ F*+ + +++ + M*                    R*     7AA    3 1 , 2 8

CANONICAL                       CDR
STRUCTURE                       CSR                                CSR    DIVERSITY
H2      KNOWN   505152a bc535455565758596061626364 65  71   SIZE   P O S I T I O N
H2.1    YES     + + + - --+ + G*+ + + + + + + + + V*        4AA    5 3 , 5 4
H2.2    YES     + + + P*--+ + G*+ + + + + + + + + A*        5AA    5 3 , 5 4
H2.3    YES     + + + P*--+ G*F + + + + + + + + + R*        5AA    5 2 , 5 3
H2.4    YES     + + + N*KG+ K*Y*+ + + + + + + + + R*        7AA    5 2 , 5 3
```

```
* = NONRANDOM,CRITICAL CSR AA RESIDUE(S);
+ = PARENTAL (or REPLACEMENT) AA RESIDUE NONESSENTIAL TO CSR;
- = AA RESIDUE NOT PRESENT; P- = ANY AA RESIDUE BUT PROLINE;
DIVERSITY POSITION = POSITION HAVING RANDOMIZED AA IN LIBRARY
```

FIG. 6

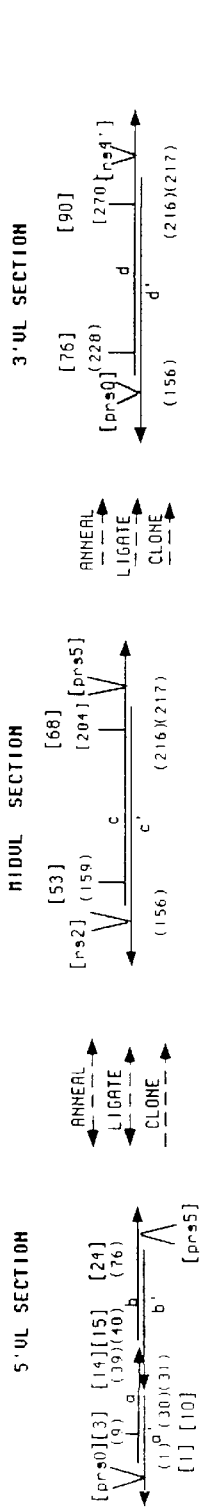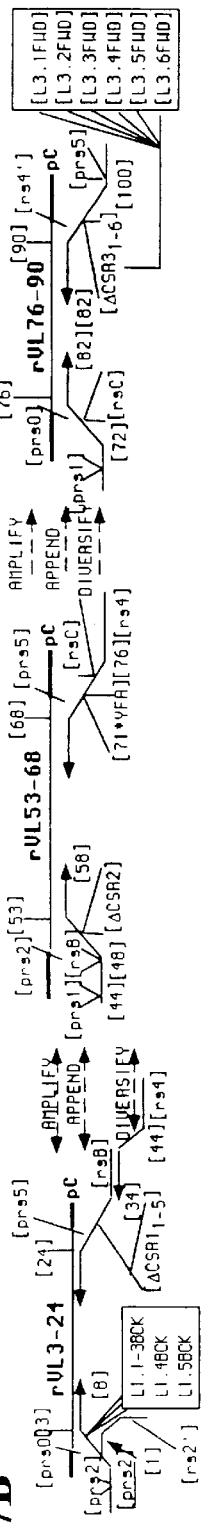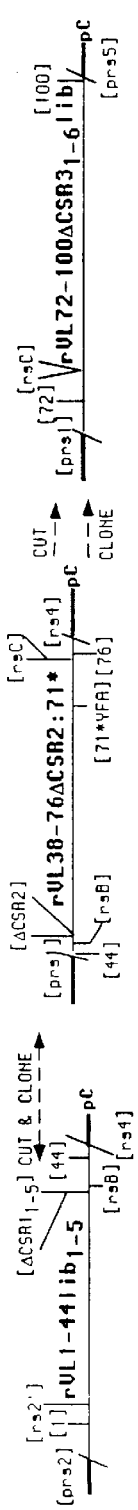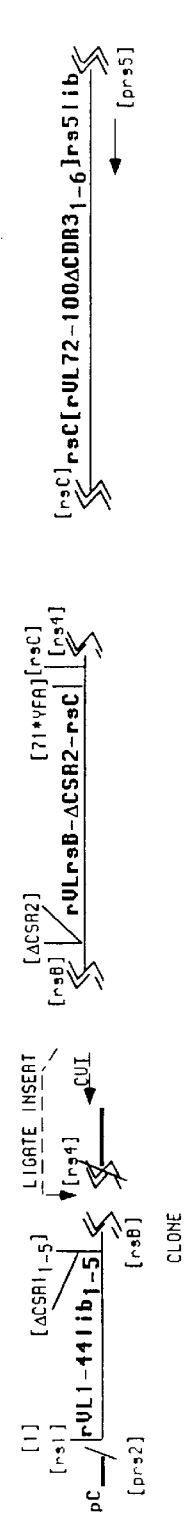
FIG. 7A
FIG. 7B
FIG. 7C
FIG. 7D rVLlib PRIMER CONSTRUCTION

| | | | | |
|---|---|---|---|---|
| 1. | L1.1FWD: | 19-24ASSSV(NNN)2M3435-rsB-38-rs4...... | 63mer | ΔCDR |
| 2. | L1.2FWD: | 19-24ASQSI(NNN)232L34-rsB-38-rs4...... | 66mer | ΔCDR |
| 3. | L1.3FWD: | 19-24SSESL(NNN)232L34-rsB-38-rs4...... | 66mer | ΔCDR |
| 4. | L1.4FWD: | 19-24SQSSL(NNN)232L34-rsB-38-rs4...... | 66mer | ΔCDR |
| 5. | L1.5FWD: | 19-24GSESD(NNN)2SNGNT32L34-rsX-36-rs4...... | 66mer | ΔCDR |
| 6. | L1.1-3BCK: | ......prs2-prs2',2(I)3-9 | 36mer | APPEND |
| 7. | L1.4BCK: | ......prs2-prs2',2(V)3-9 | 36mer | APPEND |
| 8. | L1.5BCK: | ......prs2-prs2',2(S)3-9 | 36mer | APPEND |
| 9. | L1ALLFWD: | 34-rsB-44-prs5...... | 54mer | APPEND |
| 10. | L1ALLBCK: | .....prs0-prs1-rs2' | 45mer | AMPLIFY |
| 11. | L271YFWK: | 63-71(Y)-rsC-76-prs5(10) | 49mer | APPEND |
| 12. | L271YFWK: | 63-71(F)-rsC-76-prs5(10) | 49mer | APPEND |
| 13. | L271YFWK: | 63-71(A)-rsC-76-prs5(10) | 49mer | APPEND |
| 14. | L2ALLBCK: | 38-rsB-48(I)49(NNN)252-58 | 60mer | ΔCDR |
| 15. | L1-8ALLBCK: | .....prs1-prs2-1-8 | 49mer | AMPLIFY |
| 16. | L3.1FWD: | 84-89Q 91(NNN)294P9697-100 | 54mer | ΔCDR |
| 17. | L3.2FWD: | 84-89Q 91(NNN)2P959697-100 | 54mer | ΔCDR |
| 18. | L3.3FWD: | 84-89Q 91(NNN)294P97-100 | 54mer | ΔCDR |
| 19. | L3.4FWD: | 84-899091(NNN)294959697-100 | 54mer | ΔCDR |
| 20. | L3.5FWD: | 84-8990919293(NNN)294959697-100 | 54mer | ΔCDR |
| 21. | L3.6FWDV | 84-89909192(NNN)294959697-100 | 54mer | ΔCDR |
| 21. | L3ALLBCK: | prs6-72-rsC-76-82 | 48mer | APPEND |
| 22. | LJCLLNKFWD: | 95-100-rsC-110-rs4 | 51mer | APPEND |
| 23. | CLFWD: | 209-rs4'-216(rs4)-prs5 | 36mer | APPEND |
| 24. | CLBCK: | prs0-105-107(CLLNK)-110-116 | 45mer | APPEND | rVHlib PRIMER CONSTRUCTION

| | | | | |
|---|---|---|---|---|
| 25 | 5'VHFWD: | 40-51-rs3-pUC | 54mer | APPEND |
| 26 | 5'VHBCK: | prs1-1(prs2)-7 | 30mer | AMPLIFY |
| 27 | H1.1BCK | 17-rsB-23A*25G*F*28F*30(NNN)3233M*35-40 | 63mer | ΔCDR |
| 28 | H1.2BCK | 17-rsB-23A*25G*S*28F*30(NNN)3233M*35-40 | 63mer | ΔCDR |
| 29 | H1.3BCK | 17-rsB-232425G*Y*28F*30(NNN)31a3233W*35-40 | 66mer | ΔCDR |
| 30 | H1ALLFWD | pCFWD= pCLONALLFWD (see ...) | | AMPLIFY |
| 31 | H31FWD: | 100-104-rs3o-rs3(CH1LNK)-rs3'-prs4 | 39mer | APPEND |
| 32. | H31BCK: | pC-17-rsB-24 | 30mer | APPEND |
| 33 | H2.1FWD | 474849505152(NNN)54G*56-rsD-59... | 45mer | ΔCDR |
| 34 | H2.2FWD | 474849505152P*(NNN)54G*56-rsD-59... | 48mer | ΔCDR |
| 35 | H2.3FWD' | 474849505152P*(NNN)G*F 56-rsD-59... | 48mer | ΔCDR |
| 36 | H2ALLBCK | 15-24pC | 36mer | AMPLIFY |
| 37 | 3'VHFWD: | 89-95-rs5-pCFWD | 30mer | AMPLIFY |
| 38 | 3'VHBCK: | prs2-56-rsD*-59-65 | 39mer | AMPLIFY |
| 39 | H3.5FWD: | 89-95(NNN)3DY-rs3o-104 | 39mer | ΔCDR |
| 40 | H3.7FWD: | 89-95G(NNN)Y(NNN)D(NNN)DG-rs3o-104 | 45mer | ΔCDR |
| 41 | H3.10FWD: | 89-95Y(NNN)S(NNN)P(NNN)YFDY-rs3o-104 | 54mer | ΔCDR |

SEQUENCING PRIMERS

| | | | | |
|---|---|---|---|---|
| 42. | pCFWD | pUCFWD = pCLONALLFWD | | SEQ. |
| 43. | pCBCK | pUCBCK = pCLONALLBCK | | SEQ. |

FIG. 10

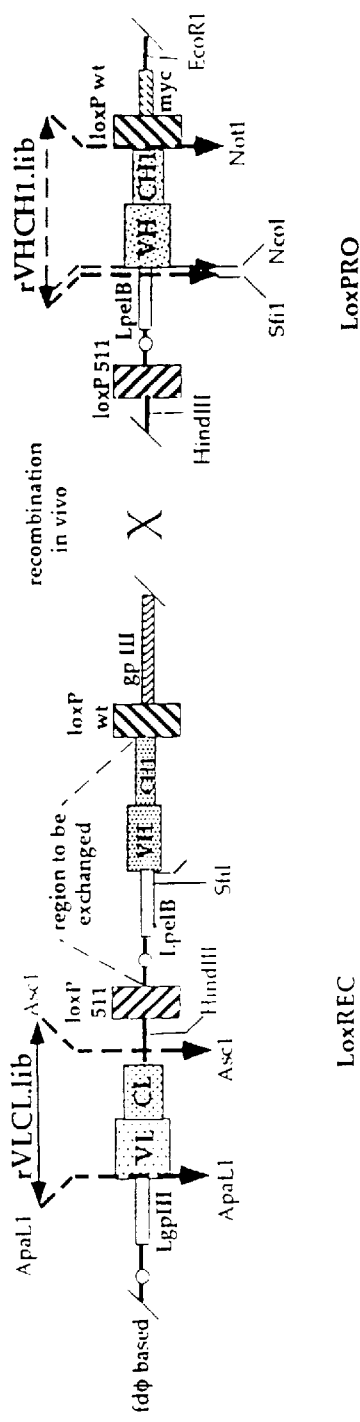
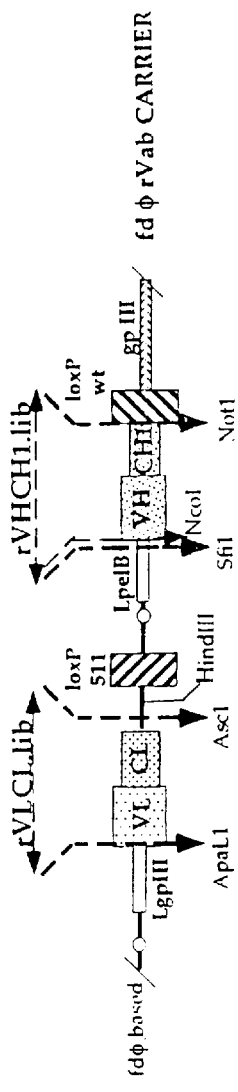
FIG. 11C  Individual VHCH1 and VLCL within a bacterium are recombined in vivo (X) by Cre recombinase
FIG. 11D

16A. Isolation for Target Recognition (T+)
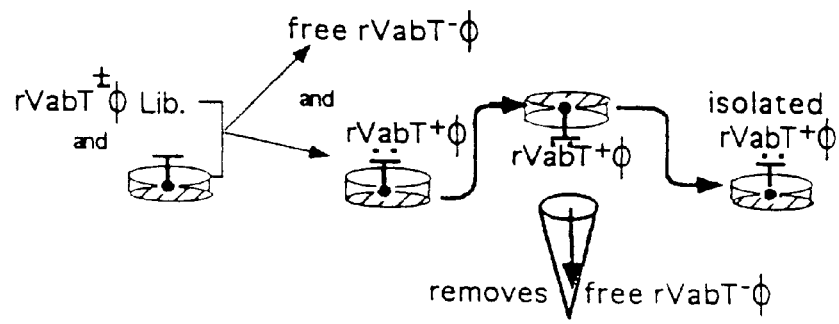
16B. Isolation for Target Specificity and/or Selectivity (S+)
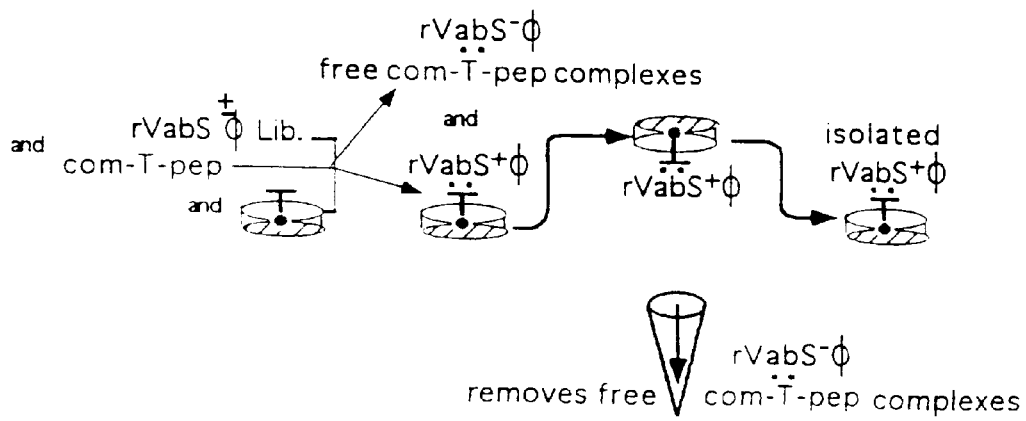
FIG. 16

FIG. 19

24.1 For a set of TSA⁺ rVabs for a specific Target:Determine the General Orientational Matrix for each attribute $R_j$ $R$ = Generalized orientational matrix $[\phi, \Psi, \omega]$ mapping similar attributes $\alpha, \beta, \gamma$ = Chemical and structural attributes $$[x, y, z, \alpha, \beta, \gamma, ...]_j \longrightarrow [x^+, y^+, z^+, \alpha, \beta, \gamma, ...]_j$$

$$x^+, y^+, z^+ = R_j(\phi, \Psi, \omega)(x, y, z)$$

24.2 Find the set of Rj's that minimizes some target function of $\alpha, \beta, \gamma$ without atomic clashes

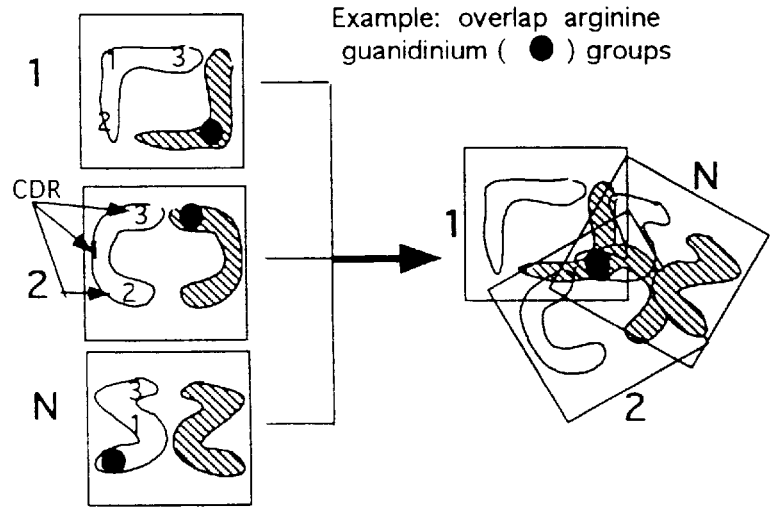

Example: overlap arginine guanidinium ( ● ) groups $V_{HEAVY}$ CSRS+CDRH3 =     $V_{LIGHT}$ CSRS =

FIG. 24

1. After obtaining the first {attribute}$_j$; i.e., { R }$_j$,
   Repeat process for hydrophobicity ; i.e., { H }$_j$
   Search for the overlap of the
      {H}$_j$ of methyl groups with the {R}$_j$ of arginines 2. Now use {R}$_j$ ⊗ {H}$_j$ as good predictor of other
   overlaps for the other sets of chemical attributes 3. Iterate process; eliminate 'outliers' and derive a single,
   overlapping neighborhood Active Surface Scanner surface
   $$S = \{R⊗ H⊗.....Z\}_{j=1,N}$$
   this is the BEEP ,
   i.e., the Biological Enhanced Ensemble Pharmacophore 4. Model of a 2D-BEEP

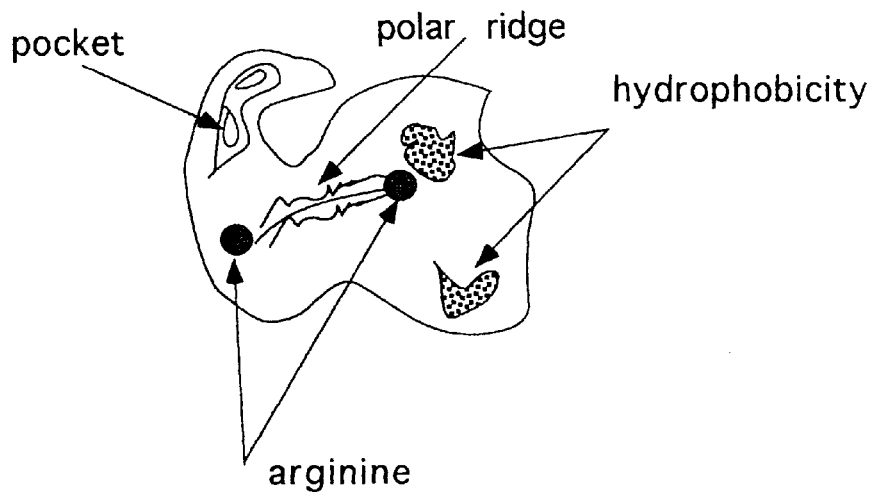

FIG. 25

TARGET SPECIFIC SCREENS AND THEIR USE FOR DISCOVERING SMALL ORGANIC MOLECULAR PHARMACOPHORES

This is a continuation-in-part of abandoned U.S. application Ser. No. 08/286,084 filed Aug. 3, 1994 and which is incorporated in its entirety herein.

FIELD OF THE INVENTION

The invention relates to a general process by which recombinantly derived antibodies (rVab) are engineered and selected to identify unique active surfaces of pharmaceutical targets. These recombinant antibodies are useful as reagents to identify natural or synthetic entities which occupy active surfaces of pharmaceutical targets and which therefore may be useful as therapeutics. This invention also relates to elucidating the three dimensional conformations of the various rVabs which bind to the pharmaceutical target and confers target regulation and the use of high resolution molecular models to identify or synthesize biologically active small organic molecules useful as viable discovery drug leads.

BACKGROUND OF THE INVENTION

Today there are many approaches to identifying chemical entities which have a desired effect on a pharmaceutical target and therefore potential as drugs. Common to all of these processes is the sequential use of multiple assays to identify a test compound's composite activity profile. This activity profile usually consists of information on four basic attributes: potency, activity, selectivity and specificity. Selectivity indicates the ability to distinguish among closely related members of a particular target family. Specificity is the ability to distinguish between unrelated targets. Only two types of assays are used to develop the activity profile of a potential drug: one, a binding assay to measure affinity (i.e. potency) of the compound; and a second, an activity assay, to measure the compounds effect (i.e. agonistic or antagonistic) on the target. Binding assays measure the formation of the complex between target (T) and ligand (L). Targets include receptors, enzymes or structural components. Ligands include signals such as hormones, neurotransmitters, growth factors or test compounds. Until recently, L was labelled in some fashion (L*) for identification and quantitation of the L:T complex. Recently, binding assays have been developed which use a tagged R (R*) to assess L affinity (see below). All these processes of labelling and R:L complex isolation and quantitation are known to those skilled in the art and have been reviewed.

In the process of searching for small organic molecules with appropriate potency, activity, selectivity and specificity for a particular pharmaceutical target, the order of testing is most often affinity, activity, selectivity and then specificity. In addition, some form of binding and/or activity assay, is interspersed with synthetic chemistry efforts at improving the compounds attributes. This generates an iterative cyclic discovery processes in which various assays and synthesis are repeated over until a compound possessing all of the desirable properties is obtained.

The present iterative process, although successful, is extremely time consuming and has a high probability of failure for several reasons. Although binding and activity assays have now been automated, screening takes significant time as it is done on individual entities within chemical files containing over 100,000 entities. In addition, the properties of potency, activity, specificity and selectivity are separable, such that the presence in a compound of any one property is not predictive of attaining another. For example, binding assays give no conclusive data on the activity (i.e., a compound with high affinity may be an antagonist), and activity assays do not predict selectivity or affinity. As a result, modifying a compound so as to change one of its attributes (i.e., agonist activity) without modifying another (i.e., target affinity or selectivity) is unpredictable and considerable time is added to the discovery program when high affinity compounds identified early in the discovery process turn out to have inappropriate activity or selectivity.

The relatively large number of biologically active small organic ligands having different general structures and which are capable of binding to a particular pharmaceutical target suggest that the binding surface of the target is not singularly unique. Furthermore, binding assays using an endogenous ligand or close analog thereof are inherently biased to compounds which bind to only a fraction of the available surface of the target. Even where the labelled ligand is not an endogenous one, this confinement means that the vast majority of active compounds identified by this process will be greatly restricted to the surface domain of the target which is used for interaction with the endogenous ligand.

This limitation is often viewed as desirable because the recognition domain for the endogenous ligand are those known via previous studies to have the ability to modify target activity. However, investigation of only one target area severely restricts the ability to identify useful ligands. As endogenous ligands in most instances are agonists peptides as in the case of opiate receptors, antagonist discovery can become a rare event. In addition, because endogenous binding domains often exhibit limited diversity among receptor members of a single target family, it becomes difficult for active compounds to discriminate among target family members. This often occurs when the endogenous signal for the family is a single entity and not a group of closely related entities. Acetylcholine (ACh) receptors are an example of a target family with only one signal entity. The catecholamine receptors are an example of a target family with a few but highly related endogenous catechol signals.

In many cases, target diversity is found in target domains other than the specific binding site of the endogenous ligand. Some of these domains may be associated with the target's other functions, i.e., signal transmission while others are quiescent domains not being used by any endogenous signals recognition or transmission. An example of a dilemma in discriminating among target family members is that found for the muscarinic receptor family (AChRm) where the binding domain for acetylcholine is used to monitor a test compound's potency, yet finding AChRm agonists which distinguish among the five ACHRm subtypes has proven illusive to date.

The task for drug discovery is to devise a screening approach which provides detectable ligands to be used to screen compounds which bind to the target and provide information regarding potency, activity, specificity and selectivity, as well as the three dimension (3D) conformation of compounds active at that particular site on the pharmaceutical target.

As part of any solution of these problems it is also necessary to establish binding assays which report the interaction of test compounds with allosteric modulatory sites on targets. An allosteric site is one which modifies the endogenous ligand binding site yet is discontinuous and non-overlapping with that site. Such target sites have important physiological and pharmaceutical consequences and have been reported. For example, the allosteric site on the Gaba A receptor binds benzodiazepines (BDZ) and thereby modulates the binding of the endogenous neurotransmitter Gaba. Occupation of the allosteric BDZ site, which can be done by chemicals from many unrelated structural groups, has a significant and recognized therapeutic influence on physiological processes including anxiety and sedation.

It is also known that active allosteric sites exist which are modulatory for endogenous ligand binding and have observable effects of their own on the target. Such an allosteric site is present on the Gaba receptor. [Garrett, Blume and Abel 1986; Garrett, Abel and Blume 1986].

Present screening techniques which monitor direct binding of test compounds to allosteric target sites are not routinely done because a) high affinity tagged ligands which bind to these sites are usually unavailable at the start of a discovery program; and b) the necessary monitoring of detectable endogenous ligand dissociation or bioassays are too time consuming in initial screening protocols. Without a simple, rapid and comprehensive way to observe all potential target sites, investigation of the surface of a pharmaceutical target for potential modulation remains limited to a small part of the target surface. New methods are necessary to survey the entire target surface in early screening for discovery leads.

Recently methods of identifying various entities which recognize target surfaces have been reported which do not depend upon the availability of tagged ligands with high affinity for the target. [Delvin, J. J., Panganiban, L. C., and Devlin, P. E., 1990]. These assays detect a compounds surface recognition activity directly via formation of an identifiable tagged target (T*):Ligand complex. In one version, test compound is coupled in identifiable compartments to a solid matrix of varied composition at concentrations which allow sufficient amounts of labelled target to bind and form stable ligand-labelled target complexes for subsequent detection via chemical, radioactive, or biological methods known to those skilled in the art. Subsequent isolation (or identification) of test compound from the compartments containing labelled target provide active chemical structures. In one such version where test compounds are free oligonucleotides, the oligonucleotides are isolated in complexes with the target, and are amplified and sequenced by PCR technology. [Delvin, J. J., Panganiban, L. C., and Devlin, P. E., 1990].

Phage display is a particularly sensitive method of presenting peptide test compounds to a target. Phage may be engineered to express the gene encoding the test peptide as a fusion protein with one of its surface proteins. Methods involving phage display are referred to in Winter et al. PCT application WO 92/20791; Huse, WO92/06204; and Ladner et al. WO90/02809.

Although these newer approaches have now been incorporated into random drug screening protocols, they do not resolve the following problems: the assays of the critical attributes of potency, activity, selectivity and specificity are still unconnected; active target surfaces including the endogenous ligand site and allosteric sites have not been identified; and 3D information on conformation of the active agent is not provided. More importantly, most of the agents available for screening, i.e., peptides, nucleotides, lipids, and carbohydrates which are available in large libraries, are not totally satisfying as discovery leads because none are expected to be orally active, or pass membrane barriers to get at intracellular or central nervous system targets. In addition, these classes of compounds are so flexible as to obscure their active 3D-configuration to such a degree as to prevent or severely limit their use as models for organic synthetic efforts. An improvement in screening would then encompass a resolution of these deficiencies so that these broad surface recognition libraries could attain their full usefulness.

In covering the prior art for high throughput binding screens for target modifiers, it also is necessary to review what is known of the endogenous ligand signals as well as their targets. Both shed significant light on additional problems and limitations encountered in the binding assays available today for discovery approaches.

Endogenous ligand signals are those ligands which directly modify target activity. The size of endogenous ligands varies greatly, ranging from 100 Daltons (e.g., as for glycine in its regulatory role as an excitatory amino acid neurotransmitter) to over 100 kD (e.g., as for some extracellularly active growth factors (GF) with a proportioned increase on surface area. The composition of endogenous ligand is equally varied including organics such as neurotransmitters; peptides e.g. somatostatin, LH, LHRH and TRH; proteins eg., growth factors; and lipids; carbohydrates; and inorganics such as ions.

For discovery purposes, common to all is the desire to replace the endogenous ligand with a small organic molecule. The problem of screening for replacements appears to be very different for most small endogenous ligands, i.e, neurotransmitters and neuropeptide modulators compared to large endogenous ligands i.e., hormones, growth and differentiation factors. Although small organic molecules have been found which can be active at targets for small endogenous ligands, few, if any have been found for the larger molecules such as proteins.

Corresponding to the diversity in endogenous ligands is the equally extensive diversity in target domains which are responsible for recognizing (i.e., binding) and responding to endogenous ligand signals. It is generally accepted that both signal and target have specific domains involved in forming the actual contact points found within the endogenous ligand:target complex (EnL:T). Recent data on crystallized growth hormone (GH) and its receptor complex provides detailed molecular information on the amino acids within the GH hormone ligand and its target GH receptor interactive domains.

Recent data on the crystal structure of GH and its receptor has shown a single GH molecule to contact the same set of amino acids in each of two identical GH receptor units complexed with one GH molecule. [Cunningham and Wells 1989; Cunningham et al. 1991; DeVos, et al. 1992]. Each of the receptor units therefore has only one target site which is the same on both units. Each receptor uses the same 7 amino acids to define the binding site which participate in GH binding and receptor dimerization necessary for activity. [Cunningham and Wells 1989; Cunningham et al. 1991; DeVos, et al. 1992].

Dimerization of at least two receptor subunits by monomeric or multimeric hormones is required for receptor activation for the majority of hormones studied to date, such as growth factors, including nerve growth factor (NGF), epidermal growth factor (EGF), fibroblast growth factor (FGF), interleukins (IL2, 4 and 6), interferons and insulin. [DeFronzo, Bonadonna, and Ferrannini, 1992; Bamborough, Hedgecock and Richards 1994; Kishimoto, et al. 1994; Claesson-Welsh, 1995]. In some cases, the two units of the hormone, as well as receptor are not genetically related. In such cases one subunit provides high affinity hormone binding and the other intracellular signalling (e.g., tyrosine kinase activity). [Ullrich, et al., 1986; Kaplan, Martin-Zanco, and Patrada, 1991; Kaplan, et al. 1991; Klein, et al. 1991; Argetsinger, et al. 1993; Obermeier, et al. 1993; Weiss 1993]. In some cases, the lower affinity receptor when dimerized can be activated. [Ullrich and Schlessinger 1990; Stahl and Yancopoulos 1993; Claesson-Welsh 1995].

Among many hormones and hormone receptors, it is now apparent that an unexpected and unanticipated degree of structural homology exists with subgroups of these signals and receptors forming homologous families which sometimes follow along different genetic evolutionary lines. Other functional similarities may be brought about as a result of convergent evolution. In either case, the active 3D conformations of ligands and receptors appear to follow some general principals. However, for drug discovery, the principals gleaned from these studies have not yet been detailed enough to bypass crystallography of particular hormone/receptor complexes in order to gain sufficient specific information as to deduce the molecular shape of active small organic molecules.

Deciphering the elements necessary in a signal to activate a hormone/growth factor receptor has included (1) crystal formation and analysis at <3 Å of receptor and endogenous ligand complexes; (2) the influence on function (i.e, ligand binding and receptor activation) caused by molecular biological mutagenesis of single amino acids or short peptide deletion/replacement, or chimera formation of both the hormone and receptor units. In addition, monoclonal antibody binding to surface domains available when ligand and receptor are either uncomplexed or in the R:L complex, along with the ability of Fab2 versus Fab1 to activate or block receptor activation in vitro, in situ or in vivo has been studied.

The above studies when taken together, provide information concerning (1) the contact points between hormone and receptor; (2) the amount of energy of binding involved in these contact points; (3) amino acids outside of the receptor:ligand contact points essential for global receptor/ligand stability or dimer stability, or receptor signalling activity (i.e. tyrosine kinase, binding of other intracellular regulatory factors, internalization, uncoupling for effector system).

Critical for identifying small organic molecules which are active at hormone receptors are the data from the above indicating (1) number of units/active complex; (2) amino acids of the target specifically involved in the binding domain with the endogenous ligand; and 3) amino acids of the ligand specifically involved in binding and/or activating the target. Of all of the above information, clearly the rate limiting event today is obtaining sufficiently resolved crystallography data of hormone/receptor complexes. However, complexes of receptor and ligand are often difficult to identify and crystalize thus preventing one from obtaining the structural information. It is also recognized that the various molecular, biological, immunological studies, biochemical and pharmacological studies noted above, also take considerable time and effort. Accordingly, prior art approaches to identifying active small organic molecules are long and arduous with unpredictable results.

In the approach outlined above, it is important that both structural and biological data be obtained as each has its own limitations and artifacts. Also, contact points could reflect specific aspects of crystal formation which do not reflect the structure at the protein in situ, or the crystal may contain an inappropriate number of subunits. On the other hand, the biological data generates both false positives and negatives. Furthermore, if antibodies are used to probe the binding site of the target, not all receptor or ligand surfaces may be immunogenetic accessible to Fab2 or Fab1 antibody. Another problem is the difficulty studying allosteric sites which do not interact directly with the signal ligand.

Despite considerable effort, a major problem in drug discovery has been the identification of small organic molecules capable of activating peptide hormone/growth factor receptors. This is likely the result of the multivalent nature of endogenous ligands for these receptors and the requirement to dimerize or simultaneously activate multiple attachment sites on a single receptor (receptor subunits) for receptor activation. Even for receptors which are homodimers, such as GH receptor (GHR), a single small organic molecular monovalent attachment to the GHR site I is not sufficient to cause activation, nor displacement of growth hormone from its active divalent dimer receptor complex.

Failure to find single small organic molecules in conventional binding assays stems from the fact that the labelled hormone is bivalent, and its displacement from two receptor units by a single monovalent small organic molecule (i.e. compounds which attach to only one receptor target at a time) is thermodynamically unfavorable in the present day binding assay. Furthermore, in the large majority of cases the receptor for a given hormone is a heterodimer. Thus, for a given hormone/growth factor-receptor binding pair, there may exist at least two different binding sites on the target which may be due to the multimeric nature of the target or a target consisting of allosteric sites on a monomeric unit. In all of these cases, the endogenous ligand must therefore comprise at least a sufficient number of binding sites which are properly spaced to bind to the multiple sites on the target necessary for activation. Obviously, one would then require a multimeric or a multivalent small organic molecule for displacement of these hormones from their targets.

Given the complexity required of each small organic molecule to bind the receptor at the multiple sites necessary for activity, or to displace the endogenous ligand, one could expect that the occurrence of a single small organic molecule with two unrelated yet active binding domains would be equal to the chance of finding one multiplied by the chance of finding the other independently. As active small organic molecules are found by random robotic assays at a frequency of between $1/1000$ to $1/10,000$ on most screens for ligands requiring only one binding site on the ligand, and which have correspondingly a single binding site on the receptor, one would expect to screen an organic chemical libraries containing from $10^6$ to $10^8$ compounds in order to identify an active molecule. Such libraries exceed those which could be screened in some reasonable assay format and actually exceed most made by even the largest pharmaceutical companies.

Therefore, a different approach to screening for small organic molecules which can activate hormone receptors is needed.

A number of libraries now exist for screening such large numbers. Two have been noted already, the oligonucleotide and peptide library. Another such file contains natural products.

Classical chemical libraries consisting of synthetically derived small organic molecules are routinely available from commercial sources (e.g. Alldrich, and Kodak) and consist of upwards of a 1–200,000 entities. Recently a survey of the chemical entities within such libraries uncovered 100,000 or so chemical structures as being the cores upon which most of the individual entities were crafted. The average molecular weight of the entity within such files ranges between 200–400 Daltons which would account for no more than one such contact site per target.

Screening of small chemical compound libraries is limited only by their availability, which most often is <100,000.

With the advent of molecular biology and gene cloning and sequencing, it has been discovered that most pharmaceutical targets are not unique entities unto themselves, but in fact belong to families of sometimes rather large size and close relatedness. Recognition of this fact has mandated a much more serious look at all of the members of the family to which the target under investigation belongs so as to identify lead compounds which can distinguish among its family members. If one used only binding assays as a primary screen for potency, activity, selectivity and specificity, one would require affinity labelled standards for each of the family members. Although this is potentially possible when the endogenous ligand signal are proteins due to their native affinity and ease of labelling, it is not presently feasible where small organics are the only known signals. This approach is also unsuitable for targets with unidentified signal ligands. Any discovery of how to include such widespread specificity testing into primary binding screen assays would greatly increase the probability of drug discovery success.

SUMMARY OF THE INVENTION

This invention provides compositions and methods for identifying active surfaces of biologically active sites of pharmaceutical targets. Identification of these sites is useful for preparing reagents suitable for use in screening assays of small organic molecules to identify those as candidate lead compounds possessing desired attributes of biological activity, specificity, selectivity and affinity.

Reagents are provided by this invention which are suitable for identifying active sites on pharmaceutical targets. The reagents comprise libraries of variable regions of antibodies obtained and modified by molecular biology techniques which are used to prepare recombinant Fab fragments (rVab) useful for scanning the surface of a target in a manner so as to identify those rVab's having desired potency, activity, specificity and selectivity. The attributes of potency, activity, specificity and selectivity are collectively referred to as a "composite activity profile" (CAP). The rVab's which are made and identified by this invention as possessing the desired CAP attributes specifically bind the target (i.e. are $T^+$), are selective for the target ($S^+$) and activate the target or are capable of activating the target when combined with another ligand ($A^+$).

By combining structural features of various members of the recombinant antibody library which possess activity at a defined pharmaceutical target, this invention provides a method of determining a composite structure possessing the desired composite activity profile. This composite structure may then be used to identify small organic molecules capable of acting at the target surface with either agonist or antagonist activity with the sufficient specificity and electivity.

The method according to this invention of identifying ligands capable of binding to active sites and possessing a composite activity profile for a given pharmaceutical target comprises combining members of a recombinant antibody library with a pharmaceutical target coupled to a reporter which reporter is capable of signaling activation or inhibition of the pharmaceutical target. Reporters of pharmaceutical activity may include but are not limited to, for example, receptor coupling to modulators such as the G protein; oligomerization of receptor subunits; changes in enzymatic activity such as kinase activity; or changes in ion flux. According to this method, individual members of the library possessing desired activity as demonstrated by the reporter, are useful individually or collectively in subsequent assays to identify small organic molecules capable of possessing the desired activity at the pharmaceutical target. By combining structural features in common between multiple members of the library possessing the desired activity, a composite structure for activity may be derived which may then be used to create a model for a compound possessing the desired activity attributes.

This invention also provides a method of identifying small organic molecules which are active at the target sites comprising screening potential drug candidates in a binding assay for their ability to displace labelled, rVab members possessing a desired composite activity profile consisting of potency activity, selectivity and specificity for the pharmaceutical target.

Small organic molecules as candidates for drugs may also be identified by analyzing the structure of the model derived from the structure of at least two active members of the rVab library and determining common characteristics including, but not limited to charge and spacial orientations which participate in binding to the active sites of the pharmaceutical target. Using the model, small organic molecules may be obtained by synthesizing compounds possessing the common structural features identified in the model, or screening a chemical file data base for members possessing features in common with the model.

This invention also provides means of identifying structural requirements of ligands capable of binding to pharmacological targets comprising multiple binding sites existing on one or more molecular entities which when bound by a single ligand are capable of activating the pharmacological target. Similarly, this invention provides a means of identifying structural requirements of multivalent ligands capable of activating pharmacological targets comprising binding sites too large to be occupied by a monovalent small organic molecule or requiring concurrent binding of a multivalent ligand to effect oligomerization of separate molecular entities to form an active pharmacological target.

This invention also provides reagents comprising recombinant antibody libraries (rVab's) which have been constructed to encode CSR and CDR regions with specific variations and in which the CDR and CSR regions are expressed on a specific identifiable framework structures.

The recombinant libraries of the invention may be packaged in various forms including bacterial phage which express the recombinant antibodies on their surface.

It is therefore an object or the present invention to provide a process for the identification of small organic molecular replacements capable of modifying a pharmaceutical target with a desired composite activity profile comprising sufficient potency, activity, specificity and selectivity to be considered as an initial drug discovery lead.

It is a particular object of this process to identify surfaces of a pharmaceutical targets capable of discriminating among members of a family of related targets which are activated by the same or similar endogenous ligand or utilize similar signal transduction mechanisms.

It is a particular object of this process to identify active or regulatory surfaces of a pharmaceutical target which may or may not be used by an endogenous ligand for the target of interest, and which is nevertheless capable of modifying the pharmaceutical target in some pharmaceutically useful manner.

It is a particular object of this process to identify allosteric sites on the pharmaceutical target which are not used by endogenous signals nor have activity on their own, as well as active allosteric sites which are used by endogenous signals other than the pharmaceutical target activating signal and which have some type of activity on their own.

It is a particular object of this process to provide a repertoire of surface recognition libraries which together recognize diverse pharmaceutical target surfaces by constructing a small number of combinatorial antibody libraries.

It is a particular object of this process to convert by a single simple and rapid process any unlabelled recombinant variable antibody fragment (rVab) isolated from a library to a labelled one to act as a reagent capable of identifying small organic molecules which possess any one, or combination thereof, of the attributes of potency, activity, specificity or selectivity simultaneously when screening random chemical libraries.

It is an object of this process to identify the specific binding regions of pharmaceutical targets requiring binding to sites in at least two different regions to cause a response of the target. Such regions may be present on monomeric or oligomeric pharmaceutical targets. The endogenous ligands for such sites generally are multivalent monomeric or oligomeric proteins which bind to the multiple regions which define the active surface of the pharmaceutical target.

This invention provides a method for identifying the structural requirements for ligands to bind at the separate regions and identifying such ligands. By combining the ligands capable of individually binding to the separate regions into a single molecule, fully active ligands are provided.

It is another object of this invention to identify the monovalent determinants making up the active surfaces on the targets for large protein signals such as hormones and growth and differentiation factors consisting of oligomeric receptors. Such receptors may contain homologous or heterologous components with one or more of these units obtaining a part of the signal recognition determinant. It is a particular object of this process to use chemical oligomerization of small organic molecules for each of multiple binding sites to derive an active oligomer for large proteins such as growth factors and hormones which contain multiple binding sites within their active binding domains.

Accordingly, another object of this invention is to identify small organic molecule replacements for large protein signals such as growth factors and protein hormones be they allosteric or competitive modifiers and whether they be monovalent or multivalent.

It is a particular object of this invention to identify small organic molecule replacements for pharmaceutical targets which have no bioorganic endogenous ligand signals, such ascertain ion channels, pumps, and exchangers.

It is a particular object of this invention to provide high volume binding assays which discriminate agonist from antagonist small organic molecule replacements.

It is a particular object of this process to be able to identity from large antibody variable region libraries, individual variable regions which distinguish from one another binding sites which confer selectivity of pharmaceutical targets for specific members of a gene family.

It is a particular object of this process to provide labelled antibody variable regions which interact with and modify the activity of targets which have no identified endogenous ligand, nor exogenous natural signals, and which labelled ligands have sufficient affinity for the pharmaceutical target to be used in competing binding assays in which small organic molecules may compete for binding with the labelled ligands.

It is another object of this invention to provide a plurality of different recombinant antibody variable regions which recognize at least one common binding site of a pharmaceutical target and which collectively provide structural information useful for designing active small organic molecules which are active at the pharmaceutical target.

It is another object of this process to provide a general method to rapidly obtain peptide structures which are useful as 3D models comprising the minimum characteristics of small organic molecule replacements which have sufficient potency, activity, selectivity and specificity to classify as viable discovery leads.

It is a particular object of this process to provide molecular models for active ligands wherein the pharmaceutical target necessary to be occupied by active ligand comprises one or more binding sites on one or more molecular entities.

It is a particular object of this process to be able to solve the canonical structures of the CDR VH3 of recombinant antibodies which have been identified as possessing the desired properties of potency, activity, selectivity and specificity.

It is a particular object of this process to be able to use composite structural characteristics to direct a synthetic effort capable of directly synthesizing active small organic molecules.

BRIEF DESCRIPTION OF THE FIGURES

FIG. 1. Stages of the Topographic System Assay (TSA). FIG. 1 shows the activities and products of the three main stages of the TSA. When combined together, Stage I and II, or Stage I and III, allow the identification of small organic molecules (SOMERS) which are active at pharmacological targets (T). A MULTIMER is at least two SOMERs covalently linked together to produce an active molecule. A BEEP is a biologically enhanced ensembled pharmacophore, and Tn is subunit n of pharmacological target.

FIG. 2. Related Antibody Structures and Variable Region Domains. A. Shows various forms of antibody structures including the variable (V) and constant (C) regions of immunoglobulin (Ig) heavy (H) and light(L) chains. Antibodies constructed in this invention by molecular biology technology have a r prefix. B. Shows details of the antigen recognition Variable region (V) domains of the VL and VH. FW is the 'constant' framework regions; "CDR" refers to the complementary determining regions as defined by Kabat (Kabat 1991); CSR refers to canonical structures found in CDRs as originally defined by Chothia (Chothia and Lesk, 1987); V (with leader sequence), D (diversity) and J (V/C junction) are the genes which are combined to create the mature VH and VL genes. V Regions are attached via genetic recombination for VL to either a kappa or lambda Constant region. VH are recombined with three Constant regions in sequence with CH1 being attached to VH. The V regions of the invention can used either without C regions, or with kappa or lambda for CL, and up to three C regions for CH.

FIG. 3. Potential Planar, Cavity and Grove Antibodies of Known Crystalline Structure for rVab Library Construction.

FIG. 3 lists a number of antibodies for which there data is known concerning their crystalline structure and which are potential parental antibody structures for construction of the rVab library as described in this invention. The antibodies are grouped according to their type of antibody combining site: i.e., planar, grove or cavity-type structure.

Figure 4A:
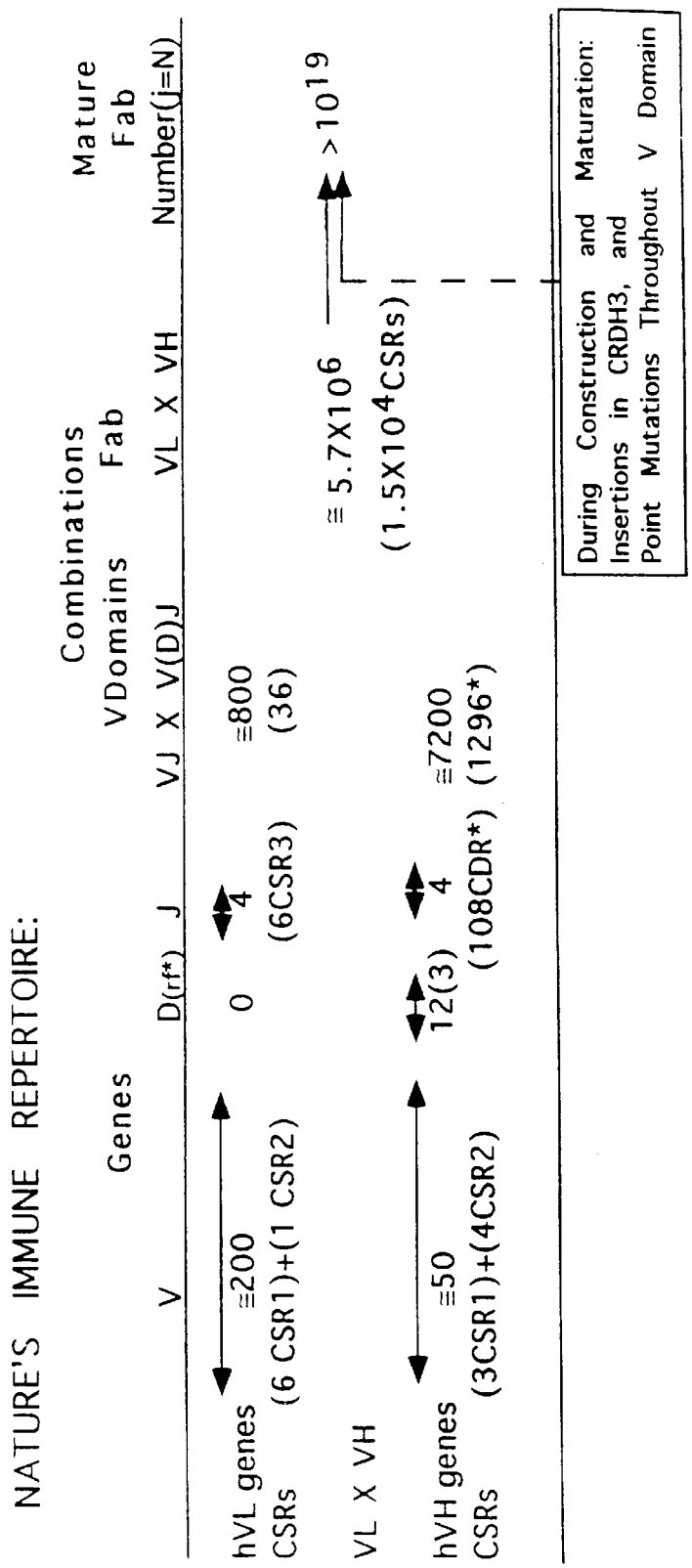
FIGS. 4A and B. Comparison of Natural Fab and rVab Library Diversification. A Nature's Immune Repertoire. V, D and J are the genes recombined to make the mature V gene; rf* are the reading frames of the D gene which can be used to make sense protein sequences upon recombination with V and J. CDR* are there are no CSRs for the VH3 region. The number of known CSR for each CDR is given in parentheses. B. The rVab Repertoire: Diversification arises by using all permutations of the known CSRs, 3 different length CDRH3 and randomization of amino acids at two positions within each CSR (or CDRH3) within a single VH and VL parental framework structure. Primary randomizations are made during construction of the rVH and rVL (see FIGS. 7, 8) and allows all 20 essential amino acids to appear at given positions within V regions among members of the rVH and rVL libraries. CDRH3 are three known CRDH3s of different sequence and three different lengths covering VH amino acid positions 95–102 (see text for details). rVab is encoded by one rVHCH1 and one rVLCL gene on the same piece of DNA. Totals of CSR include CSR and CDRH3 combinations.

FIG. 5. Type and Diversification of Amino Acids at various positions within V region. Numbering of the amino acid (AA) positions as per Kabat (Kabat, 1991). Library Diversification identifies the high priority candidate amino acid position for primary library diversification during construction of rVH.lib and rVL.lib as described in this invention.

FIG. 6. CDR and Canonical Structures (CSR) of V Regions. Particular amino acid (single letter code) at V gene positions critical for particular CSRs are given as defined by Chothia (Chothia and Lesk, 1987). * represents amino acids not within CSR or CDR which participate in defining the CSR. The diversity position is the amino acid position used for primary library randomization as described in this invention.

FIG. 7. Construction of the rVLCL Lib. of Diversified Canonical CSRs: rVLCL.Lib. A–F are sequential steps of the process constructing rVL.Lib. G is the final step of recombination of rVL.Lib with a rCL to form rVLCL.Lib. Amino acid positions occur in brackets; nucleotide positions are given left to right as 5'-3' in parenthesis; restriction sites (rs) also appear in brackets and have a "p" prefix to denote when they are located within the plasmid and not the V region. Restriction sites are denoted by combinations of letters and numbers. Primer direction is denoted by arrows (left is forward (FWD)), and right is a reverse (BCK) primer). * denotes more than one amino acid at a CSR position which is critical for a particular CSR; Δ denotes that diversification by randomization of amino acids with CSR or CDR has occurred. Lib suffixes indicate a library of many individual members. Heavy line indicates that the product (single entity or library) has been cloned in to plasmid pCLONALL (pC).

FIG. 8. Construction of the CSR and CDRH3 Diversified rVHCH1.Lib. Construction of CSRH1 and H2 and three CDRH3 of different lengths (i.e., 5, 7, or 10 amino acid insertions); diversification by amino acid randomization and combination of CSR and CDRH3 in all possible permutations is as illustrated in a manner analogous to that described for rVLCL.Lib (see legend to FIG. 7).

FIG. 9. General Usage Plasmids. A. Illustrates the sequence of restriction sites (rs) which occurs in the cloning site of pCLONALL. Use of each in rVH.Lib and rVL.Lib construction is noted wherein "- - - " denotes a restriction site used and defined by parental AB sequence; wherein X denotes a restriction site not used in that particular rV.lib construction. General positions of restriction sites within the rV and rC regions under construction are shown. JCH and JJCL are the natural J/C gene recombination region with included amino acid positions given in brackets. JCLINK is the position of the J/C recombination restriction site, also referred to as rs3. B. Events used in constructing the plasmids carrying rC regions and in the final step of rVab.Lib construction wherein rV regions are appended to rC regions. The two plasmids needed for this are listed as pVxACCEPTORs. C. Plasmids used in creating expression vectors for the rVHCH1 and rVLCL chains of the rVab when not attached to phage coat protein gpIII. EK is the enterokinase cleavage site. ISOTAG is the additional amino acid sequence useful in isolation and labelling rVab as rVab-REPORTER constructs.

FIG. 10. General Primer Table. Primers are written as 5'-3'. Numbers and single letters designate individual amino acid positions which in the primers would be corresponding triplet codon sequences for the amino acid at these positions. The letter N within parenthesis denotes the random appearance of the nucleotides A,T,U,C used to randomize the amino acid at this position. Letters, without parenthesis are used for sequences necessary for a desired CSR or CDRH3 structure; numbers are used for sequences which are not critical to CSR or CDRH3 structure. rs is a restriction site sequence. Sequences for all FWD primers are complementary to the sense sequence. Approximate primer sizes in nucleotides are listed as #mer. The right hand column signifies general use of primer with amino acid randomization; and SEQ. is sequencing.

FIG. 11. Constructs for CRE-LOX recombinatorial formation of rVab.lib: PartI. Expression of rVab with or without one attached random octamer peptide (Pep 8) library. FIG. 11 illustrates the steps generating the necessary phagmid and plasmid constructs to allow in vivo recombination of individual rVHCH1.lib and rVLCL.lib members, by the Cre recombinase, and the construction of a single phagmid containing an rVHCH1 and rVLCL member on one piece of DNA (i.e., an rVab). This procedure is used for rVab.Lib construction where there is no need in the TSA discovery process for subsequent addition to rVab of more than one random octamer peptide (PEp8.Lib). Wild type (wt) and mutant (511) loxP sites are as defined in legend to FIG. 12. LpelB and LgpIII are leader sequences for pelB and gpIII.

FIG. 12. CRE-LOX Plasmid and Phagmid Sequences used for rVab.lib Construction. For use in rVab.lib construction by in vivo Cre-recombinase directed recombination of rVHCH1 and rVLCL onto single phagmids where there is a subsequent need in the TSA process for attachment to rVab of no more than one random peptide library.

FIG. 13. Constructs for CRE-LOX Recombinatorial Formation of rVab.Lib: Part II. Expression of rVab with or without one or two attached random octamer (PEp8) peptide libraries. Steps involved in adding Pep8.Lib; i) illustrates expressing one peptide ($PEP^{1at}$) at the amino terminus of VH ($Pap8^{1at}$); ii) illustrates expressing one peptide at the carboxyterminus of CL ($Pep^{1ct}$); and iii) illustrates expressing one peptide at the aminoterminus of VH ($Pep^{1at}$ and one peptide at the carboxyterminus of VL ($Pep^{2ct}$). Step E illustrates use of two primers required to append Pep8.Lib to either VH or CL.

FIG. 14. In vivo, Generation and Expression of rVab.Lib members. The generation of rVL and rVH gene pairs (rVab) as one DNA molecule, as well as the expression and phage display of rVab attached to coat proteins of fd is illustrated. Synthesis of rVHCH1- and rVLCL proteins and their complexation to form gpIII attached rVab for phage display is illustrated showing cells, such as bacteria, infection of bacteria with phage carrying rVLCL and transformation with DNA plasmids carrying the rVHCH1-construct; and in vivo recombination of rVHCH1 and rVLCL onto a single fd via the LOX sequences and the P1 provided CRE-recombinase. Following recombination and replication, a combined single expressible pair of rVab genes is packaged per phage. When induced, rVLCL is made and introduced via its leader into the periplasmic space were its complexes under reduced conditions with synthesized rVHCH1-gpIII coat protein to create the desired rVab complex attached to the gpIII phage coat: protein (see text for details).

FIG. 15 Flow Diagram of Diversification and Simplification Paths of the TSA. Steps are outlined for optimizing TSA+ attributes of rVabs for a given pharmacological target. The library attributes are potency of binding to Target (T), specificity and selectivity for Target (S) and regulation of target Activity (A). "+" denotes that the attribute is present in the rVab member.

FIG. 16. Isolation of Target (T+) Specific/Selective (S+) rVab. A. Isolation by panning for Target recognition (binding) (T+). B. Isolation by panning for Target Specificity and/or Selectivity (S+). Isolation of T+ and S+ rVab can be done in any order, and when used together isolate rVabTS+ members. T denotes the pharmacological target; ϕ phage displayed rVab; com-T-pep represents the entity, holotarget, subunit or peptide fragment, which is to be distinguished from the Target. Binding to the com-T-pep prevents rVabS binding to matrix attached T.

FIG. 17. Selection of rVab Scanners for Active Target Surfaces Used by Signals with Single Attachment Sites. FIG. 17 presents a ilow diagram of the TSA process isolating rVabTSA+ members from a rVab library previously identified as T+S+. T, S and A are defined in legend to FIG. 15. Native signal is the endogenous or previously identified agonist entity (e.g., protein, peptide, neurotransmitter) which activates Target by interaction at a single attachment site (see Text for details). Allosteric Effector is an endogenous or previously identified entity which binds to a single attachment site on Target which modifies agonist activity but has no activity on its own. rVabA+ are isolated by competition by native signal or allosteric change in T by allosteric effector which prevents normal rVabTS+ binding to T. The binding of rVabTS+A-members is unaffected by the presence of the allosteric effector or native signal and therefore is not isolated free in the supernatant during this process.

FIG. 18. Discovery of SOMERs for a Target with a Single Univalent Active Site. FIG. 18 illustrates the steps of the TSA process of rVab-Scanner to Reporter conversion and Reporter use in competitive binding assays to identify active SOMERs for the pharmacological Target. Both competitive and allosteric active SOMERs are identified in this process.

FIG. 19. Identification and Isolation of Active rVabTSA$^+$ for the Muscarinic Acetylcholine Receptor subtype m1 ($AChR_{m1}$). (s)—denotes matrix attached Wheat Germ Agglutinin; T, S and A are as defined in the legend to FIG. 15; R denotes receptor target; G denotes guanine nucleotide binding protein; RG denotes RG noncovalent complex; ϕ denotes phage displaying rVab. The TSA process isolating rVab based on specificity/selectivity (see FIG. 16) is illustrated for the isolation of $AChR_{m1}$ $rVabS_{m1}$+ using Agonist-Like rVabT+A+ (type 1 rVabTA+). The same process is used Nor isolating Partial-Agonist-Like, Allosteric-Agonist-Like and Competitive Antagonist-Like S+ rVabTA+ (i.e., respectively type 2, 3 and 4 rVabTA+)

FIG. 20. Isolation of Active rVabTSA$^+$ for Complex Active Sites on Dimeric Receptor Targets ($T_{1-2}$). FIG. 20 illustrates the TSA process by which the rVab pair for each part of the active site on each of two receptor target subunits (T1 or T2) is isolated. The process is shown in full for one member of the pair; that for the active site region on T1, and is duplicated for the active site region on T2. m-T denotes matrix attached Target; comp-T-receptor denotes comp-T-pep as described in FIG. 16. ϕ denotes phage displayed. Pep8.Lib is the random octapeptide library displayed as a fusion protein with phage coat protein gpIII. $Pep8T_2$+ is the library of peptides which bind to T2. rVabT1-Pep8T2.Lib is the rVabT1S+.Lib to which the PEp8T2+ Lib has been appended (see FIGS. 12 and 13 for details of rVab-Pep.Lib construction). Preselection of the T2+ Pep8.lib is not required and a random Pep8 Lib can be used in this process. Testing for rVabS+ is optional and can be done at any step along the process. The related rVabT2m+S+A+-Pep8T1+ member of the active domain pair is obtained in parallel analogous manner.

FIG. 21. Using Active Bivalent rVabT1-Pep8T2 to Screen for Disomer Replacements of a Multivalent Signal. FIG. 21 presents a flow diagram of the steps of the TSA in which each rVab member of the active pair of rVab-Pep8 for both domains of the active site, which occur on separate T subunits are used to find a DISOMER replacement for the native signal and which regulates Target activity. [A+] denotes that the rVab-Pep entity is active in regulating the T1-2 dimeric Target. A* denotes that the rVabTS+ member is derived from a rVab-Pep entity which is [A+]. DISOMERmn denotes covalent linked SOMERs for the pair of active site domains identified by the paired rVabTSA* members.

FIG. 22 Summary of the Discovery of DISOMERs for a Bivalent Hormone.

FIG. 23. Flow Chart of TSA Steps Creating and Using a Biologically Enhanced Ensembled Pharmacophore (BEEP).

FIG. 24. The TSA Process of Finding and Relating Sets of Surface Attributes of rVabTSA+ to Create a BEEP.

FIG. 25. The TSA Process of Finding the Surface Common to All Active rVabTSA+ Scanners for an Active Site of a Target.

DETAILED DESCRIPTION OF THE INVENTION

This invention provides methods and compositions for identifying ligands capable of identifying active sites on pharmacological targets. This invention utilizes recombinant antibodies which possess the combined attributes of potency (affinity), selectivity, specificity, and activity as reagents useful for modelling active ligands and identifying small organic molecules which also possess these attributes and therefore utility as drug leads or therapeutic compounds.

I. Pharmacological Tar gets Identified by this Invention.

Pharmacological targets may be receptors for endogenous or other ligands which evoke a physiological response by the cells on which the receptors are present. Besides receptors, the pharmacological target may be ion channels, transport proteins, adhesion proteins such as N-CAM, or any other physiological regulatory surface which is excessible to being identified by the recombinant antibodies and which is activated by a specific ligand. A non-limiting list of exemplary physiological ligands for which active surfaces may be identified by using the methods and compositions of this invention are listed in Example 4.

Receptors may include those for neurotransmitters, hormones, growth or trophic factors, modulatory peptides, ions or other moieties which act as signal ligands for the pharmacological target. Preferred nonlimiting examples of neurotransmitter and peptide receptors for which active surfaces may be identified include those for acetylcholine, i.e., nicotinic, and the various forms of the muscarinic m1-5 receptor subtypes; adrenergic receptors including $\alpha_1$, $\alpha_2$, $\beta_1$, $\beta_2$,; dopaminergic receptors including $D_1$, $D_{2a}$, $D_{2b}$, $D_3$ and $D_4$, and $D_5$; serotonin receptors including $5\text{-HT}_1$, $5\text{-HT}_{1\text{-}A\text{-}D}$, $5\text{-HT}_2$, $5\text{-HT}_3$, and $5\text{-HT}_4$; benzodiazepine receptors; opiod receptors including $\acute{o}$, $\kappa$, and $\mu$; and others. Also preferred are receptors for hormones and growth factors which may, for example, include those for insulin; growth hormone; erythropoetin; neurotrophic factors, including but not limited to nerve growth factor, ciliary neurotrophic factor, brain derived neurotrophic factor, NT-3 and NT-4. Receptors for cytokines such as interferons, and the interleukins are also preferred as are receptors for nonpeptide hormones such as thyroid hormone, and glucocorticoids. The methods and compositions of this invention described herein may be adapted by methods known in the art and applied generally to identifying the specific binding surfaces of other pharmacological targets as well.

Other target surfaces for which active ligands may be identified include extracellular, intracellular, nuclear or mitochondrial located soluble or membrane associated proteins, carbohydrates, lipids nucleic acids or complexes thereof which play a role in a physiological or pathophysiological process involving a predictable indication for which one would like to have a drug based therapy.

The pharmacological targets according to this invention, are physiological molecules, or combinations of molecules associated through covalent or non-covalent forces, which alone or in combination with other molecules, evoke a physiological or therapeutic response when activated by a ligand which binds the "active surface" of the pharmacological target. By "active surface" is meant the region of the pharmacological target which can bind a ligand, whether or not there are native endogenous ligands for these sites, and translate that binding into a physiological meaningful response characteristic of the target. Where the response requires oligomerization of at least two separate molecular entities by a ligand, binding to the active surface on only one of the molecular entities is insufficient to evoke the physiological response.

The active surface is comprised of specific atoms or other chemical moieties which participate in the binding of the ligand to the pharmacological target, for example by contributing to changes in enthalpy or entropy. The active surface of the pharmacological target may be small, capable of being bound by a single monovalent ligand having a molecular weight of less than about 1000 daltons; or large, requiring a multivalent ligand for binding to a plurality of binding sites which contribute to the active surface. Multiple binding sites may be present in a larger binding domain in a single region of the pharmacological target. Alternatively, multiple binding sites may be present as separate non-contiguous regions which may be bound by a ligand capable of spanning the pharmacological target to simultaneously bind the different binding sites of the target. In addition, binding sites may be present on two or more molecular entities, which may be the same or different, and which require oligomerization by binding to a multivalent ligand.

Growth Factors (GF), including NGF, EGF, FGF, interleukin (e.g. IL2, 4, 6) interferons, insulins and many other extracellular biosignals along with their respective receptor targets apparently contain multiple target binding sites. Such protein signals are in the order of 20–1000 K Daltons and exist as monomers or homo- or heterodimers or more complex multimers, which encompass surface areas of tens of thousands of $\text{Å}^2$. Estimates of the surface area of such endogenous ligands and receptors which are occluded by their association ranges from 500–1600 $\text{Å}^2$. By the above definition, each ligand has $\geq 2$ binding sites and each receptor has $\geq 2$ corresponding binding site which are discontinuous and non-overlapping with each other.

II. Use of Recombinant Antibodies rVab's as Scanners to Identify Active Surfaces This invention identifies and characterizes active surfaces by constructing and using a sufficiently large repertoire of diverse ligands capable of "scanning" the surface of pharmacological targets and binding to their active surfaces. Confirmation of binding to active surfaces is accomplished according to this invention by monitoring a change in function of the pharmacological target or by monitoring a biochemical or biophysical change which reports binding and/or activation of the pharmacological target or receptor on the target.

Antibodies have most of the above required attributes and can be recombinantly engineered so as to acquire unique attributes required for use in this invention. It is well known that antibodies occur which are neutralizing and therefore by definition antagonistic in that they prevent, competitively or allosterically, the binding of signal to receptor, or receptor activity.

Antibody epitopes in protein targets range from a few amino acids to about 20 amino acids and cover from hundreds to thousands $\text{Å}^2$ of target surface. In addition, epitopes can comprise sequential or noncontiguous groups of amino acids. However, it is equally clear that antibodies can recognize organic epitopes which are relegated to much smaller volumes, (i.e., <50–200 $\text{Å}^2$) as are those associated most frequently with small organic haptins (i.e., clinitrophenol or morphine). As antibody affinity and selectivity can be equal with both large and small epitopes, it is assumed that anti-target rVab antibodies will have landscape recognition surfaces which range over all of these dimensions.

A. Use of rVab Libraries

The repertoire of different ligands for scanning the pharmacological target according to this invention is provided by an antibody library comprising recombinant Fab fragments, or portions thereof, constructed to present a sufficiently large repertoire of different identifiable structures, some of which will be expected to bind and, depending on whether concurrent binding to multiple sites is required, activate the pharmacological target. These active antibodies are identified as specific members of a library which may be considered to scan the entire surface of the pharmacological target and possess the desired composite activity profile for the binding site. According to this invention, the recombinant antibodies used with this invention are referred to as "rVab" to indicate that they are constructed using recombinant techniques and are made as libraries which incorporate diversified amino acid sequences in one or more regions of the antibody associated with target recognition or binding.

Where the pharmacological target comprises multiple binding sites on one molecular entity, or requires oligomerization of at least two molecules to form a single binding site with contributions from the individual subunits, or requires oligomerization of two or more molecular entities which each bind to the ligand at a different site, activity will only be observed using antibodies modified according to this invention to contain at least one additional separate binding entity. In the preferred embodiment of this invention, the separate binding entity comprises at least one random sequence of amino acids having a structure appropriate to bind a binding site not bound by the antibody's variable region. In some cases two such random sequences of amino acids would be required although it is contemplated that additional sequences may also be required. Additional binding sites on rVab can also be provided by more or less complicated protein based structures including smaller peptides, larger proteins including intact enzymes or even another antibody, in structures described in the literature such as diabodies (Winter et al. 1994). Additional peptide sequences which may be used to add additional binding sites preferably are between about 5 and 30 amino acids in length. More preferably such sequences are between about 6 and 12 amino acids in length. Most preferably, such sequences contain 8 amino acids.

An antibody identified as recognizing the binding site is simultaneously or sequentially further characterized by determining its selectively and activity for the pharmacological target. To streamline an rVab selection process for more than one target attribute, target specificity (T) and some of the activity (A) testing may be simultaneously characterized.

The order of isolating Vab for $A^+$ and $S^+$ can be varied, most often depending upon which is the more difficult attribute to find among entities which modify the target of interest. For example, if selectivity among highly homogeneous target members of a single family is the critical missing attribute of existing agents, $S^+$ could be determined first, or after isolation of the population which is $A^+$.

Although antibodies which recognize (i.e. bind) the target's landscape in such a way as to modify its function make up a small percentage of those capable of passively recognizing the target (i.e. not modifying its activity), their presence is likely because of the size and diversity of the rVab library of the invention. In addition, active antibodies would also be expected to be present which have the additional desired attribute of specificity for that target. Furthermore an embodiment of this invention includes that the biological suitcases (i.e, phage or bacteria) used to individually package each rVab library member allows their recoverability after a biological replicative cycle even if present in the original library in rare copies.

This invention utilizes recent advances in molecular biology which allow the generation and manipulation of sufficiently large and diverse V (VH and/or VL) region libraries, along with both minimization and directed secondary diversification of their CDRs and CSRs to allow selected rVabs, when labelled, to act as reporters and affinity selectors in assays which identify potential active ligands. Such active ligands are preferably small organic molecules which are useful as drug leads or as therapeutics themselves.

B. Use Of rVAB Members To Identify Small Organic Molecule Replacements (SOMERS)

At least two methods are provided for identifying SOMERS based on the identification of the recombinant antibodies (rVab's) possessing the attributes of T (specificity/potency) S (selectively) and A (activity). According to one method of the invention, these [rVab T+ S+ A+] scanners are converted to reagents for reporting the presence of other ligands capable of binding to the active site on the pharmacological target. Conversion to reporters is accomplished by labelling the active scanners with a detectable label. The reporter rVab fragments may then be used in classical competitive binding assays to identify SOMERS. For simple active surfaces, single SOMERS represent active small organic molecules, while for complex active surfaces containing more than one ligand binding site, corresponding numbers of SOMERS, found in the fashion disclosed by this invention, are covalently coupled together to represent the active small organic molecules.

In another embodiment of this invention, SOMERS are identified based on the collective attributes of an ensemble of active rVab scanners which have been characterized as T+, S+ and A+. By providing a sufficiently large repertoire of antibodies, multiple antibodies possessing these desired binding attributes are expected to be identified. Common structural features of this ensemble of scanners possessing the desired CAP attributes are then used to construct a model ligand for binding to the active surface of pharmacological target. By combining structural features of multiple antibodies identified as being active for a specific pharmacological target, biologically enhanced ensemble pharmacophores ("BEEPS"), i.e., drug models, may be derived which may then be used to identify small organic molecules as drug leads or therapeutics. This molecular model, BEEP, then serves to provide a basis for screening chemical databases to identify SOMERS either by electronic screening of available chemical data bases, or as a basis for rational drug design to synthesize SOMERS expected to possess the combined attributes of specificity/potency, selectively and activity. This solves the prior art problem of access to all compounds within a chemical data base, decreases the time needed for screening and amount of manpower necessary, and could eliminate screening if used to direct a synthetic chemistry effort to create SOMERS.

III. Recombinant Antibody Libraries Provide Sufficiently Large Repertoires of Different Ligands to Identify Active Surfaces A. Function Of Recombinant Library The objects of the invention are provided by a process which makes and then uses separately and/or in batch mode, combinatorial repertoire libraries of variable regions (VH and/or VL) of recombinant antibodies (rVab) to scan the surface of a pharmacological target so as to identify and select those which have a desired potency, specificity, selectivity and activity profile. These four attributes are collectively defined herein as the compound activity profile (CAP). Members of the library possessing the desired attributes are then grouped according to the local surface domain recognized. By using a sufficiently large and diverse library as described herein it is expected that essentially most if not all relevant active surface of pharmacological targets should be identifiable using the method, of this invention. In addition, because the library is recombinantly made in a random fashion and selected in vitro, recognition of sites which would not otherwise be detected as non-self, or antigenic, or immunogenic, should occur using the rVab library described in this invention.

In addition, the objects of the invention relating to discovery of three dimensional shapes of surface areas are provided by use of the active rVab's of this invention as reporters of target structure. As described below, these rVab reporters are constructed using VH and VL domains wherein the CDR regions which may be diversified are contained in a framework of an Ig (or Fab) having a three dimensional structure which has been determined by crystallography has CDRs which contain the known canonical structures (CSRs). Such structural information about rVabs for a given delimited active target surface domain allows for the molecular resolution and deduction of the essential elements of the rigid organic structure of the constellation of critical amino acids constituting the active target surface recognition portions of the ensemble of active rVabs and thereby provide the essential elements of the rigid organic structure of active SOMERS which can bind with specificity to and modify that target.

Construction of the BEEP requires PCR determination of the amino acid sequences of rVab CDR, CSR and some framework residues in these active surface scanners through a process which uses computers and genetic algorithms. It is also possible that with sufficiently large enough active rVabs, the information obtained in the above manner will enable resolution of the active surface of the targets. This process provides the objects of the invention related to electronic screening for SOMERS by combining common structural elements in computational packages called biologically enhanced ensemble pharmacophores (i.e., BEEPS).

The recombinant antibodies used in accordance with this invention also provide an improvement over the prior art of typical labelled target-reporter binding assay screens. One improvement comprises obtaining via recombinant molecular biology technology, antibody variable regions (V) in sufficient numbers, with sufficient affinity and desired activity so as to identify those members of the library which function as surface reporters capable of recognizing active target surfaces, modulating the target through these recognition sites and distinguishing its target from among closely related targets (selectivity).

B. Size Of Recombinant Library

In order to have a sufficient likelihood of identifying the active surface of a pharmacological target, the recombinant library preferably contains at least between about $10^9$ and $10^{14}$ entities. Preferably the library contains between about $10^{10}$ and $10^{13}$ entities. Most preferably, the library contains about $10^{12}$ entities. The specific size of the library required to provide a reasonable likelihood of identifying the active site will depend on the overall surface area of the target surface and the surface area of the binding domain to be identified. The surface of most targets is of the order of 50,000–100,000 $Å_2$, with each ligand binding domain encompassing from about 100–200 $Å^2$ to about 1,000–2,000 $Å^2$. As each rVab covers only about 20–40 $Å^2$ of surface area, one requires about 2,000 rVab's to cover the target landscape, and at least 10 times that ($2\times10^4$) allowing for overlapping recognition domains. Another increase of two orders of magnitude ($2\times10^6$) allows for appropriate surface interactions which produce specific agonist or antagonist action. Another 100 fold increase allows for such rVabs to be recoverable from the library upon batch analysis. An additional $10^4$—$10^4$ fold increase allows nanomolar affinities and agonistic activity. Accordingly, the preferred useful surface scanning libraries have on the order of about $10^{12}$ entities.

It is recognized that antibodies have the ability to distinguish among closely related targets. Accordingly, recombinant libraries possessing sufficient numbers of entities are reached according to this invention by constructing recombinant libraries comprising variable regions of either, or both light (L) or heavy (H) chains which are modified or unmodified and which may or may not be expressed in combination with a constant region. These libraries may be selectively varied not only during their original construction, but also after the initial round of selection for any one or all of the three composite profile activities of target binding, selectivity and activity. Such secondary additional diversification as well as secondary simplification may be carried out by combinations of primer based PCR or oligonucleotide insertion at convenient restriction sites. Furthermore, the secondary variations may be localized to each of the 6 CDRs (i.e. the three in VL and the three in VH) or any particular combination or singular location. Variability is introduced in the CDR's by modifying the CDRs to contain random amino acid substitutions of positions involved in contact with the target. The positions of variation, including further diversification or simplification, are preferentially those within the CDR which do not alter the CSR structure of that region and are known to those skilled in the art. The number of amino acid positions to be diversified is dependent on the number of active rVab members desired to be obtained. Thus, if an insufficient number of members are identified, the library diversification can be increased by diversifying additional amino acid positions in a CDR as described below.

Given that there are twenty naturally occurring amino acids, diversification at a single amino acid position results in about 20 different potential antigen binding (touch) sites. By diversifying at two amino acid positions in each of the 3 VL CSR, 2 VH CSR, and the one VH CDRH3 which are randomly combined into VH:VL pairs by the invention, one obtains a diversity in the rVab library of $\geqq10^{18}$ members (see FIG. 4). Since a given phage library can package about $1\times10^{14}$ members, several libraries are preferably constructed and packaged in phage to contain the entire population of diversified members. Although, it is preferable to diversify two amino acids in each CDR as shown in FIG. 6, other combinations are possible. Randomization in only some of the CSRs and one CDR allows for library sizes approximating $10^{12}$ such that one phage rVab library could contain multiple copies of each diversified member. In addition, three or more non-essential amino acids in a given CDR may be diversified (see, FIG. 5 for non-essential amino acids) preferably with a corresponding decrease in diversification of amino acids in other CDRs so as to maintain the total size of the library within an attainable number. Resultant libraries of $4\times10^{12}$ members can be approached using, for example, bacteriophage as vectors. A single rVab library of this invention of at least about $10^{12}$ members, independently of how diversity is obtained, provides enough surface probes with the minimum CAP at the target to allow identification of most active surfaces of interest.

An advantage of this invention over prior art screening methods is that it scans the entire available surface of the target for active surfaces and provides active surface reporters. This allows for identification of active sites and SOMERS for targets without endogenous signals (endogenous ligand) and at target surfaces not used by natural endogenous ligands but which result in modulation of that target. The latter surfaces, referred to as allosteric surfaces, are of two types: those without activity in the absence of endogenous ligand binding to target (i.e., cryptic allosteric sites); and those having activity on their own and yet are still able to modify the action of an endogenous ligand (i.e., active allosteric sites). Obviously, the larger the target surface under scrutiny, the greater the opportunity of finding appropriate active surfaces. As endogenous ligand contact surfaces probably represent some 10% of total target surface area, including allosteric surfaces greatly increases the surface area under investigation.

The use of recombinant libraries also provides a means of reducing or increasing the number of complementary determining regions (CDR) within the variable domain of the rVab necessary to confer desired CAP attributes to the rVab. Thus, one can attain a minimal active CDR complement.

Alternatively, large scale randomization of up to most of the amino acids within the rVab CDRH3 domain may be used to increase the population of active rVab from which to identify the best rVab reporter. For example, if the initial library screened does not possess members with the sufficient constellation of CAP attributes, secondary diversification of the best candidates, by a number of procedures including PCR and various in vivo and in vitro mutagenesis systems known to those skilled in the art, and then recycling through the original identification and selection procedures described below, may be used to recover an antitarget rVab with a full complement of the desired CAP which might have been too rare to be found among the original antitarget rVab library. In addition, by identifying and sequencing active rVab CDR complements one may also obtain accurate and detailed structural information useful for modeling the essential elements of active SOMERS, i.e., as in BEEPS.

C. Affinity of Recombinant Antibodies

The rVab of the invention are used to detect and characterize active sites by providing information related to their structure, and/or to function as reporters in competition assays to identify SOMERS. Accordingly, the affinity of the rVab's useful in this invention should allow for one or both of these functions. If the rVab is used only to detect and characterize the active binding site or to contribute in developing a BEEP, its affinity may be high and a slow dissociation rate (i.e., half time of dissociation, preferably between about 5 and 30) would be suitable. However, the affinity of the rVab's useful to identify SOMERS for a pharmacological target should not be so high as to prevent dissociation and competition for use in competition assays. Preferably, this affinity will be in the range of from about 0.01 to about 100 nM. More preferable the affinity will be between about 0.1 to about 30 nM. Even more preferably the affinity will be about 0.5–10 nM. Most preferably, the affinity will be between about 1–5 nM.

D. Characterization of Ligand And Target Binding Sites

Binding domains on a signal are referred to as ligand attachment sites (LIGATTS) and those on the target as target attachment sites (TARGATTS). Where each is protein in nature, both can be defined as the surface area of the entity made up of contiguous (e.g., amino acids n and n±1) or discontiguous (e.g., amino acids n and i where i is not n±1) elements so confined in space as to be accessible and in contact at the same time with the surface of the other partner in the complex so as to contribute to the binding energy of that interaction. Where there are multiple binding sites, by our definition, each TARGATT domain forms contact points with amino acids on the signal and one SOMER would not be expected to encompass two LIGATTS. Where endogenous ligands are nonproteinaceous, other compound building blocks would replace the amino acid as the unit entity.

The sizes of LIGATTS and TARGATTS are quite variable. We have arbitrarily confined TARGATTS to the volume which can be encompassed by a synthetic small organic molecule replacement (i.e., SOMER) of less than about 1 kD. This TARGATT size, is practical and modeled by the opiate receptors' attachment site for its 30 amino acid endogenous ligand, endorphin, which easily binds morphine (<600 D) and all of the pharmaceutically known opiate analgesics, with nM affinity and is fully activated by their attachment. Identification and characterization of larger TARGATTS is considered within the scope of this invention as such sites should also be recognized by members of rVab libraries of this invention.

E. Association of Activity $A^+$ With Binding of rVab

An important feature of this invention is that the rVab's which are identified as possessing the desired CAP attributes and in particular, activity at a target, function to create a linkage between binding to a target and activity at that target. Accordingly, once an rVab is identified which is both $T^+$ and $A^+$, that rVab may then be used to identify other ligands which are also $T^+$ and $A^+$ based on competition binding assays alone.

Several methods are available to initially provide a connection between binding and activity of a rVab. In a preferred method, an active surface for a target is associated with a secondary biochemical response which may be detected upon binding of an active ligand at the active surface. Such biochemical responses may include changes in affinity of the ligand or allosteric ligands, oligomerization with other subunits, phosphorylation state, ion flux, etc. For example, and as discussed more fully below, the changes in agonist affinity of a receptor coupled to G protein based on the presence of a guanine nucleotide can provide the necessary linkage between binding and activity.

Also, as discussed in U.S. Pat. No. 4,859,609, which is incorporated herein by reference, receptors may be expressed as fusion proteins comprising the ligand binding domain of the receptor fused to a "reporter" polypeptide which undergoes an assayable change in conformation or function when the active ligand binding domain of the receptor binds to an agonist or antagonist.

IV. Method of Identifying SOMERS

The method of obtaining small organic molecules (SOMERS) which are active at pharmacologic targets is summarized as comprising the following (See FIG. 1):

Stage I (a): Construction of the scanning rVab library.

Starg I (b,c): Identification of rVab's which bind and activate target. If target is a multivalent site requiring attachment at two sites, pairs of rVab's are identified using rVab-peptide scanners to detect activity.

Stage II: Use labelled rVab's as reporters to detect SOMERS or MULTIMERS (i.e., DISOMERS).

Stage III: Create BEEPS from composite of structural information derived from rVabTSA+ for screening or synthesizing SOMERS or MULTIMERS.

A. Construction of Scanning rVab Library (Stage 1a)

Molecular biology technology is used to construct a limited number of large combinatorial libraries of recombinant antibodies (rVab libraries) wherein the VL and VH CSRs and CDRH3 occur within each library within a single Ig VH and VL framework, respectively, and optionally attached to their respective constant region (CH1 and CL). An antibody whose structure has been determined by crystallography is preferably used to provide the framework for construction for these rVab libraries. Antibodies of undetermined structure can also be used for library construction and identification of active rVabs (i.e., Stage 1 abc, FIG. 1) useful as reporter rVabs to detect SOMERS and other MULTIMERS (Stage II FIG. 1) according to the process of the invention, but only antibodies of determined structure can be used in creation of BEEPS, (Stage III, FIG. 1).

In the preferred embodiment of the invention, antibodies of solved structure are used to create the original rVab library. In another embodiment, one or two of the isolated active rVabs for a given target are subsequently crystallized and the structure determined to allow their use in Stage III. The later is useful as it allows use of the newly published sequences of the human VH and VL genes [Tomlinson et al. 1992; Williams and Winter 1993; Cox, Tomlinson and Winter 1994; Nissim et al. 1994; Tomlinson et al. 1994] for Stage III work.

In all cases, the rVab libraries constructed by the process of the invention have a sufficient number of diverse members to encompass an immunological antigenic repertoire approaching man's natural one or are made from human VH and VL genes [Roitt, 1991; Nossal 1993; Griffiths et al., 1994] which are capable of recognizing an enormous diversity of surfaces including but not restricted to proteins, nucleic acids, carbohydrates, lipids and organic haptens.

There are basically three sources of genes to be used as the starting material for construction the rVab libraries.

a) the published data on cloned and sequenced antibodies;

b) the antibody clones themselves, carried in various cell types, including hybridomas, spleen cells, bacterial plant cells, yeast and viruses, on various DNAs including Plasmids, phagmids and chromosomes; and most recently c) the published sequences of a human repertoire of VH and VL genes [Roitt, 1991; Tomlinson et al. 1992; Nossal 1993; Williams and Winter 1993; Cox, Tomlinson and Winter 1994; Griffiths et al., 1994; Nissim et al. 1994; Tomlinson et al. 1994].

Most of the sequence information is available in at least two data bases, i.e., the Brookhaven Protein data base and that of Kabat at NIH (which is also available in text form) [Kaba et al. 1991]. The structure of the majority of the crystallized antibodies is also available from the Brookhaven Protein data base. Listings of such crystallized antibodies are presented in Example 1. An example of an antibody which has been crystallized to determine its structure is described in (Tulip et al. *J. Mol. Bio.*, (1992) 227:149–150).

In the preferred embodiment, the antibody sequence is obtained first and is the starting point of rVab library construction using the following steps to construct the rVab library. The order of steps may be varied to suit particular circumstances.

I. Selection of Parental Fabs of Known Crystalline Structure as rVab Library Framework Templates II. Creating the Nucleic Acids Encoding the Heavy and Light Chains (rVHCH1 and rVLCL) for ABXXX rVab.lib.

Figures 11A, 11B:
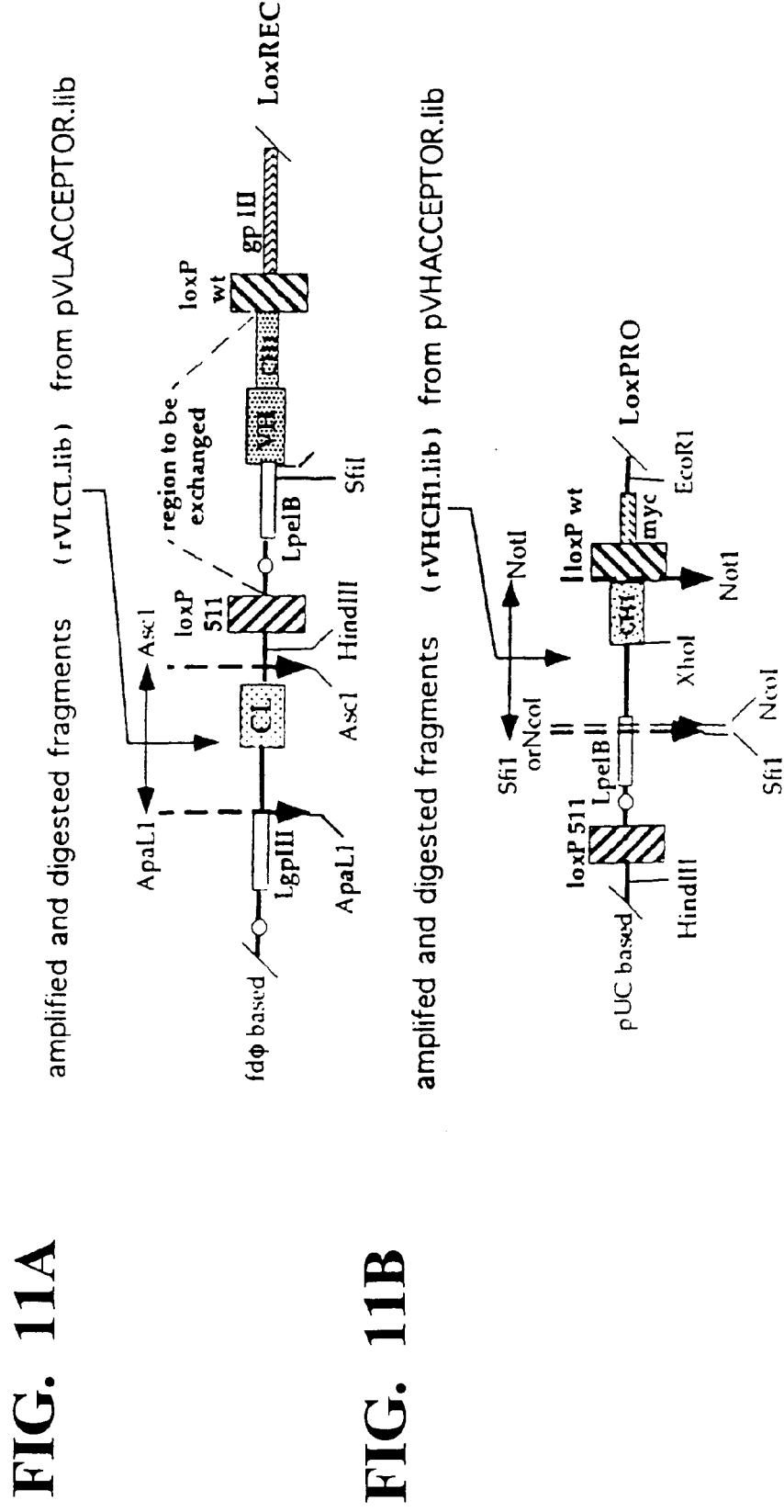
Figure 12:
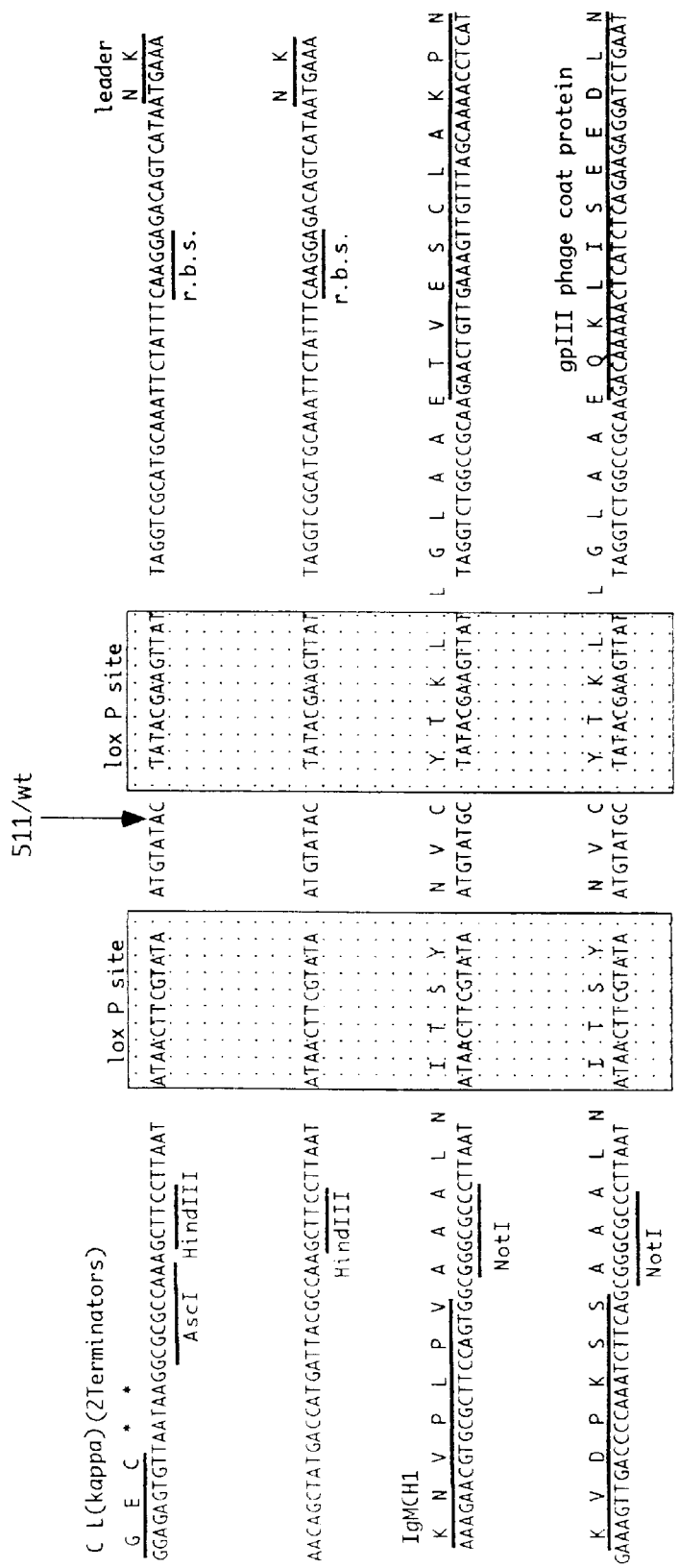
Figure 14:
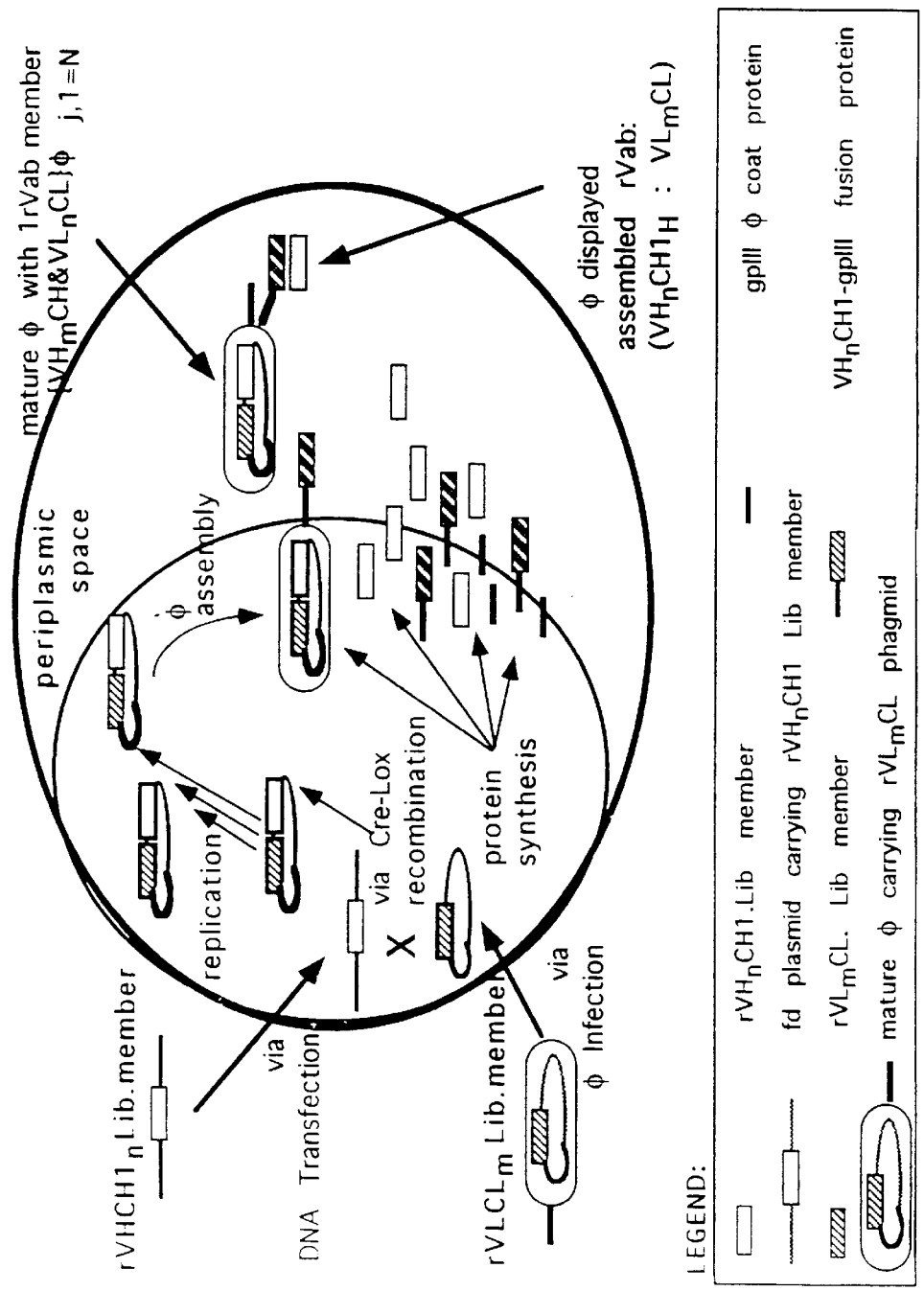

Step 1a): Construction of 5'VL Section
Step 2: Diversification By PCR
Step 1(b): Construction of the MIDVL section
Step 1(c): Construction of the 3'VL section of rVL
Step 3: Ligation III. Construction of the Constant Regions of ABxxx IV. Construction of rVHCH1.lib (FIG. 8) Construction of 5' Half of the VH Region Construction of the 3' Half of the VH Region V. VH and VL Library Sizes:

VI. Construction of the rVab.lib (the VHCH1lib×VLCLlib Combinatorial lib.) (FIGS. 11,12,14)

Step 4: In vivo recombination of VHCH1 and VLCL genes

Details of the Individual Steps for Expressing the rVLCL.1.6 and rVHCH1.L.b by CRE-LOX RECOMBINATORIAL FORMATION VI. Step 5—Generating Phage and Displaying the rVab.lib on Phage Surfaces (FIG. 14)

The critical steps are shown in FIGS. 7, 8, 11 and 14 which describe respectively the construction of rVLCL and rVHCH1 libraries, their pairing in the rVab library, and finally their expression attached to the surface of phage as functional complexes.

Both construction of the rVLCL and rVHCH1 libraries follow a similar outline wherein:

a. a limited number of oligonucleotides are synthesized containing convenient restriction sites and which cover both ends, and in one case the middle domain, of the V region, b. the oligonucleotides are ligated together, c. PCR is used to append missing and junctional regions as well as provide the means of randomization of amino acids at defined positions, d. the completed rVH and rVL libraries are ligated to appropriate constant domains wherein one library is placed within a plasmid and the other phagmid, and e. the rVH and rVL libraries are combined in vivo by the CRE-LOX recombinase provided by coinfection by P1.

Following this outline, rVab libraries of about $10^{12}$ members are constructed.

In other embodiments, a. the VH and VL genes, without constant regions, encoding an antibody of known structure are cloned via PCR to obtain the sequences encoding the VHCH1 and VLCL sections of the Igs using methods known to those in skilled in the art, and b. the Vs may then be altered via PCR to remove unwanted restriction sites, and develop convenient restriction sites bording the CSR and CDR domains.

c. selectively randomized oligonucleotides with appropriate end positional restriction sites may be used to replace each of the 6 CDR regions having appropriate matching restriction sites in the basic V framework to allow directional cloning. These oligonucleotides vary in length (i.e., n, n+1 and n+2) to match the known CSR and some length changes in CDRH3 and contain all of the amino acids at one or two positions within each CDR most often involved in antigen contact.

Figure 4B:
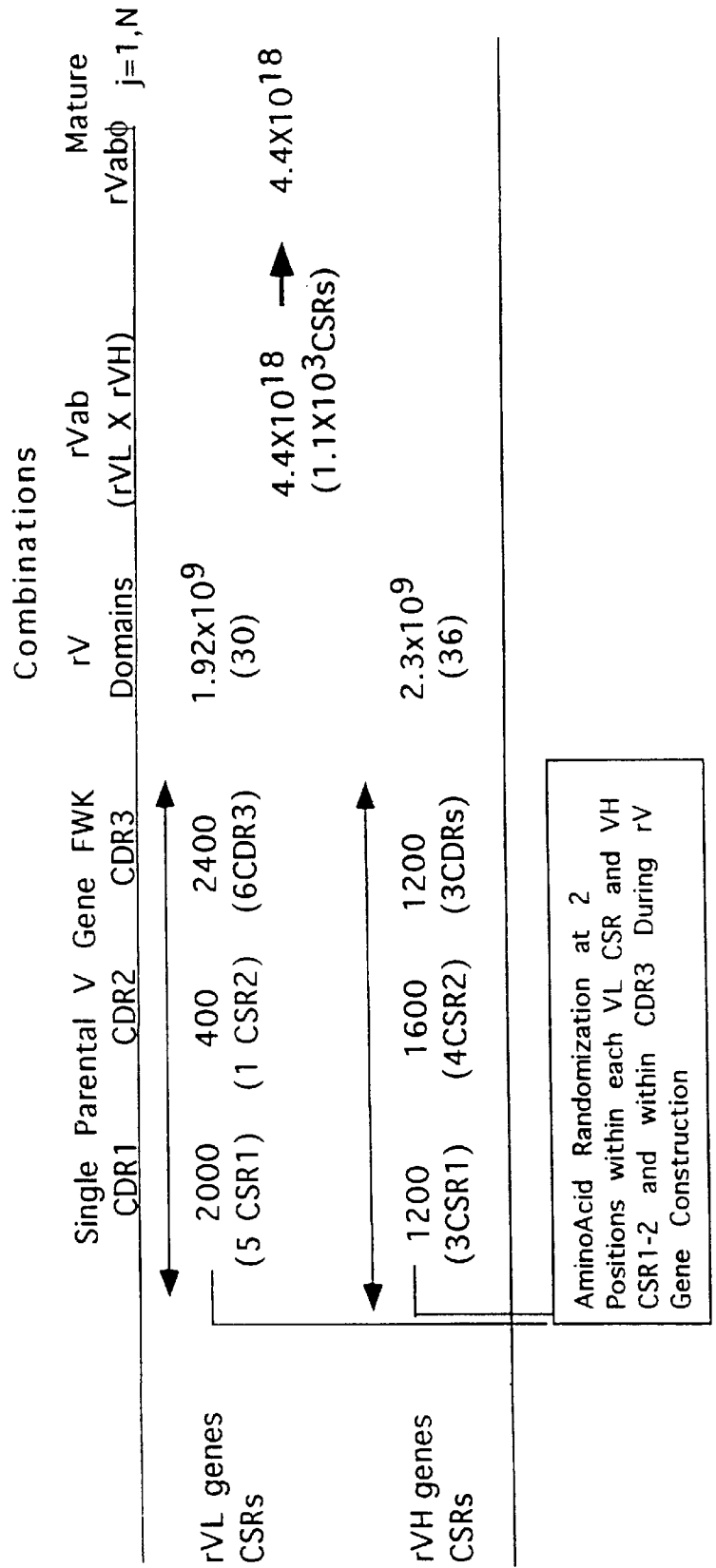

In the preferred and other embodiment, with 2 amino acid randomizations within each CSR and CDRH3 and three different lengths of CDRH3 used, the numbers of diverse members in the final rVab LIB (i.e., rVHCH1×rVLCL) reach $10^{18}$ (see FIG. 4 for details).

1. Sources of Frameworks

Frameworks in which the optimally diversified CSRs and CDRH3 are cloned into may be derived from antibodies of known structure.

Frameworks may be chosen from antibodies which present the canonical regions in different orientations with respect to the C region. Thus, it may be desirable to prepare multiple rVab libraries on different frameworks to maximize different special orientations of the CDR's.

Frameworks may be chosen which will favor binding over small to large surface areas. As discussed above, a small surface area would cover an area of about 200 $Å^2$, a medium surface area about 750 $Å^2$ and a large surface area about 1500 $Å^2$. Examples of antibodies which can provide frameworks for these three different size targets are found among the planar, cavity and grooved type antigen recognition domain present in various antibodies of known structure (FIG. 3 respectively). Frameworks may be chosen simply based on the shapes of the antigen recognition domain or in combination with other structural factors.

2. The Expressible Vab Region Construct

Preferentially, construction may be done in one of two general type vectors, a. fd and M13 (Pharmacia, USA [Smith, 1985; Scott and Smith, 1988; Parmley and Smith 1988; Cwirla, et al., 1990, McCafferty, et al. 1990; Winter and Milstein 1991; Waterhouse, et al. 1993, Recombinant Phage Antibody System Instruction Manual, Pharmacia P-L Biochemicals, USA].

i. the inserted V(H and L) with CH1 at the carboxy terminus preceded by the lac promoter and a ribosomal binding site [RBS], an export leader sequence in front of gpIII phage coat protein or PelB, a cloning site followed by either an in frame linker and then gpIII, or a double set of suppressible termination codons.

ii. the VH or VL without CH1 or CL or with partial NH2 terminal constant region amino acids may be preceded by the lac promoter -RBS-PelB- with internal cloning sites allowing in frame ligation of VH at both 5' and 3' ends and followed by -C(H or L) and either an in frame linkage to gpIII or two suppressible termination codons.

b. immunozapII (lambda) Stratacycte, CA, [Skerra, and Pluckthun 1988; Mulinax, et al. 1990, ImmunoZap Cloning Kit, Instruction Manual Stratacyte Corp. CA USA; Kang, et al. 1991; and Barbas, et al., 1991].

i. as above for V region, with and without intact CH1.

ii. as above for V region, with and without intact CH1.
Expression of Single V(H, L) -C(H or L).

Expression of single V(H or L) -C peptides may be used to confirm proper construction of the V regions, or rVHCH and rVLCL libraries, before either expression as mature VC (rVHCH or rVLCL) or CRE-LOX recombination and phage expression. fd (M13) or Lambda expression is induced with glucose as described in Pharmacia (USA) Kits or the Stratacyte (CA) system Lerner. The product may be identified with CH1 antibody (standard Elisa technology known to those skilled in the art) either with fd as phage displayed molecules, or with lambda after expression induction, and generation of periplasmic located molecules. When using phage, the induction of the lytic cycle may also be used to determine the ratio of lambda to intact rV as an indication of size of library. With fd, one can assay antibiotic (e.g. ampicillin) resistance colony forming units (cpu) transfer from within fd genome vs. the number of phage with rV display attached to the viral surface. Dishes coated with viral or rV antigen may be used to provide information on the size of the rV library.

In another embodiment, only the rVH and rVL domains are expressed and connected through a flexible linker to form a single chain V region antibody (termed scFv by Winter [Huston, et al. 1988; Bird, et al. 1988; McCafferty, et al. 1990; Hoggenboom, et al. 1991; Barbas, et al. 1991; Garrard, et al. 1991; Breitling, et al. 1991] which may be expressed using phage display. The expressed V antibodies are fused to gIII on M13 using a Recombinant Phage Antibody System Kits (Pharacia, USA), according to instructions provided the manufacturerer for construction, expression and detection.

c. General information on primer use and PCR.

To allow the library construction of various domains of rVH and rVL, and CH and CL as well, each primer includes a sequence encoding a restriction endonuclease recognition site. The sequence of the primer which contains the restriction site may be located within, partially within, and sometimes precedes the section of the primer annealing to the target Vab sequence. When it is present as an extension to the sequence homologous to the rV section under construction, it will not participate in annealing during first strand forward and second strand reverse synthesis but will participate in annealing subsequent PCR amplification cycles. Although not essential, the restriction sites (at either or both ends) are such as to generate 3' or 5' overhangs to aid in subsequent ligation utilizing restriction enzymes which maintain the appropriate reading frames. Products of PCR may be isolated from the reaction mixtures by a variety of techniques known to those skilled in the art. A number of restriction sites which have been successfully encoded within rVH and rVL gene constructs for insertion in the available expression vectors are known to those skilled in the art and are available from manufacturers of IG expression systems and Ig primers such as Pharmacia (USA), Stratacyte (CA), and 5'-3' Prime (USA).

Insertion in frame can be into vectors containing sequences encoding other proteins to produce fusion proteins not only containing one or more C constant regions, but also the coat protein gpIII and VIII of fd filamentous phage, or transmembrane proteins to provide rVHCH or rCLVL anchoring for appropriate extracellular or phage displays.

3. Preparation Of rVabs With Multiple Attachment Sites

The grouping of active rVabs based on recognition of different target surface domains is simplified by using small peptides which cover in an overlapping fashion, the liner amino acid sequence of the target. Such grouping simplifies the pairing of active rVab for a MULTIMER (e.g. DISOMER or TRISOMER) obtained from multivalent rVab-PEP libraries (example 3 and 4) as well as forms the basis of selection of active rVab for conversion to reporters for simple SOMER identification.

Given that many antigenic sites are less than 12 amino acids, peptides of 10–20 amino acids, made in overlapping fashion (i.e. amino acids 1–15, 5–20 10–25 etc.) would provide most of the sequential target epitopes. This would mean that for an average protein of 50,000 Kd, i.e., some 90 would be needed to cover the entire surface. For many pharmaceutical targets, mutagenesis and alanine scanning has provided information, known to those skilled in the art, of particular amino acids, and small groups of amino acids which are involved in signal binding and receptor activation. Such information is used here to reduce to a much smaller number the peptides needed to provide most of the desired surface epitope information. Another possibility for target fragmentation is the use of synthetic polypeptides, bought commercially or produced by biotechnology means, using commercially available expression vectors harboring specific sites for cloning and expression of peptides in fusion with easily and quantitatively recoverable proteins.

4. CSR and CDR Diversification and Reduction

CSR and CDR Randomization: A preferred embodiment will be to use synthetic oligonucleotides which vary at increasing number of amino acid positions within each CSR and CDRH3 but which do not alter the CSR. Minimal randomization of amino acids would be to have only 1 position within each CDR filled with all 20 amino acids. One could include up to about 24 amino acid positions within the CDR H3. As the number of positions randomized increases, the total possible different rVH and rVL rapidly exceeds the practical limitation of $10^{12-14}$ on phage library size, and one has to limit the number to fit within the library size that is attainable. Increased randomization at larger number of positions can be accomplished by putting amino acids into classes, i.e., basic, acid, hydrophobic, hydrophilic, etc., and then using only one or two amino acids of each group at each 'randomized' position. Secondly, since not every amino acid within a CDR is involved in contact, one can identify those which are most often involved in contact and focus amino acid randomization at those positions. Lastly, one does not need to use the same type or degree of randomization for all CSR and CDRH3 s. In one embodiment, one could use only CSRH1, H2 and H3 for randomization as VHs alone have been published to have nM antigen affinity [Ward, E. S. et al. 1989].

In the preferred embodiment, randomization may be accomplished during construction of the rVab library. In addition, secondary randomization after isolation of the initial active rVabs may also be utilized if desirable. Secondary randomization can be used to obtain a single, or pairs of missing attributes of the desired TSA CAP, or to increase or decrease one or more present CAP attributes.

CDR Reduction: To determine the smallest target binding domain it may be desirable to reduce the size of the potential rVab target binding domain. For CSR and CDR reduction there is the possibility of using only one VH or one VL, making PCR copies, cloning with primers which include only the first, first two, or last one or two CSR and CDRs within rVH and rVL, and subsequently ligating the constructs into parental frameworks wherein the missing CSR or CDR has been replaced with a string of glycines (Winter EP 0 368 684 A1). After alteration each library may be retested for its new CAP. In another approach, one can start with a preferred rVH:rVL pair and delete (again replacing each with a glycine heximer) a) one CSR or CDRH3 at a time (there being 5 such possibilities); b) two at a time (there being 14 such possibilities); c) three at time (there being 9 of these); and d) four at a time (there being 6 of these). With reduction in CSR and or CDRs, the potency of the altered rVab can be tolerated up to 30 nM, (that required for use of the rVab in subsequent binding screens for organic replacements). However, an affinity of 100 nM is tolerable in the minimal CSR/CDR combination if it is put through mutagenesis for potency improvements later on as such processes have been shown to produce increases in binding affinity of up to two orders of magnitude [Bass, Greene and Wells, 1990; Marks, et al. 1991]. The reduction in number places all of the critical contact atoms within the smallest number of semifixed domains making 3D modeling of critical atomic spacial relationships easier by means known to those skilled in the art.

5. Expression of rVabs a. Expression of rVab as a Phage Library.

In one embodiment of this invention, the rVab library is displayed on phage. This process best described recently by Griffiths et al. 1994). Methods for using phage display of antibodies have previously been published (see, Ladner et al., International patent application WO90/02809; Winter et al. WO92/20791 and Huse et al. WO92/06204 which are incorporated herein by reference) and some reagents are commercially available in kits.

In another embodiment, only the rVLCL is placed in a library for expression as a bacterial plasmid construct (VLCL.bact) with a leader which allows product release to the periplasmic space. This library is then expressed and product is combined with either one of a rVHCHL or rVLCL phage displayed library to derive the two phage and one soluble protein libraries. An anti-CL antibody attached to solid matrix may be used to harvest their VLCL protein library.

To identify members of the rVHCH1 phage library with one or more CAP attributes, the soluble rVLCL protein library is added to the above phage library and panned for target surface recognition with target protein attached to a matrix (plastic, chromatographic or magnetized beads) in the absence or presence of competing proteins (see example 2) to derive rVHCH1:rVLCL protein T+ (S+) members. The phage containing the rVHCH1 gene is harvested after allowing the phage to multiply with helper (using commercial kits). Isolation and enrichment steps may be repeated as required. This library may be referred to as T+S+ rVHCHhalfLIB. Assays for A+ may be then be done to obtain TSA+rVHCHhalfLIB.

The T+ (S+A+optional) rVHCHhalfLIB may then be cloned, in, for example, lambda and expressed as periplasm soluble entities. The library may then be mixed with the phage display rVLCL.LIB, and the above isolation steps repeated to obtain a T+ (S+A+)rVLCLhalfLIB. The specific methodology for this procedure has been published by Lerner and group [Cabilly, et al. 1984; Burton, et al. 1988; Huse, et al. 1989; Mullinax et al. 1990; Zebedee, et al. 1992; ImmunoZap Cloning Kit Stratacyte Corp. CA., and SurfZap Cloning Kit (instruction manual) Stratagene Corp, CA] and is herein included in entirety by reference. See below section on Functional VH and VL combinations for details. The active rVHCHhalf library is cloned into pVHACCEPTOR (see FIG. 11) and the active rVLCHhalf library into pVLACCEPTOR. The CRE-LOX recombination system may then be used to derive a rVab LIB combinatorial library which may be tested for the TSA+CAP.

b. Isolation Of rVab Library Of Target Binders And Phage Display

This step isolates all rVab existing within the original library which recognize some part of the target's surface and form a complex with sufficient stability for isolation (i.e, target affinity <30 nM). Those with this recognition ability are termed $T^+$. In the preferred method, the rVab genes are mixed and packaged in and displayed functionally on phage surfaces. Accordingly, rVab are displayed on the surface of phage and the phage are incubated with target surfaces. In other embodiments, the library number can be reduced by prior selection of active rVHCHhalfLIB and rVLCLhalfLIB which allows packaging and expression in bacteria, either as soluble or membrane anchored rVabs by methods known to those skilled in the art using commercially available kits (e.g. Stratacyte USA) following manufactures directions.

As discussed above, the target can be any surface one desires to scan for recognition by members of the rVab phage library. Permissible incubation conditions, of which there are many known to those skilled in the art, would include those which do not disrupt the vehicle packaging the rVab, or inactivate rVab recognition of the target, nor prevent display of its target epitopes. In addition, in all cases the rVab:target complex preferably is one which is quantitatively separable from free Tr-rVab phage packages.

After incubation of target and the rVab phage, there are many published methods for separation of complexes known to those skilled in the art which are all based on the principle of having the target tagged (denoted $Tr^{tagg}$) in such a form as to allow its convenient quantitative separation from all reaction solutes. Preferably such tags are inseparable or act as labels to follow the target:rVab complexes through separation procedures. Among such preferred tags are matrixes such as agarose, magnetic beads and the surface of culture dishes. In these cases attachment of the target to the tag would have been made prior to incubation with the rVab library. There are also non-matrix target-tags which allow target:rVab complex separation from solute and unbound rVab. Among such tags are fluorescent compounds, (for use in fluorescent activated sorting), biotin, (for avidin directed sorting) and polyhistine containing 6 residues [his 6] (for metal chelate column chromatography) and very small antibody epitopes which are known to those skilled in the art.

Incubation conditions can be varied extensively. Variations in temperature, time, pH, buffer and media additives are all to be considered as those attributes which influence target:rVab complex formation and stability in manners known to those skilled in the art. The preferred conditions here are phosphate, MOPS, Hepes or Tris buffer at about neutral pH (6.8–7.2) with 1% BSA at room temp. for about 4–6, up to about 6–12 hrs.

After formation of target:rVab complexes, any matrix bound rVab is separated from unbound free rVab. In the preferred embodiment, the target is attached to plastic culture dish surfaces, and one of any number of rapid procedures, such as panning, is used for separating free and target complexed rVab. The general approach of panning at different temperatures, pH and the presence of the antigen have been shown to allow isolation of rVab with controlled affinity.

After detachment from matrix or affinity associated tag, by procedures such as low pH or others known to those skilled in the art, the recovered $rVabT^{+}$ can be recycled through the selection procedure or any variant thereof any number of times. Published panning and affinity chromatographic procedures have shown single step enrichments of $5\times10^{2}$–$10^{3}$ per cycle. Although, the number of cycles can be varied, depending upon the enrichment found per cycle, the abundance of a particular $rVabT^{+}$, the total size and diversity of $rVabT^{+}$ recovered, 3 cycles is preferred. Other number of cycles may be chosen based on recovered $rVabT^{+}$ characteristics such as S or A.

Isolation $rVabT^{30}$ members can be done with different types of packaged rVab expressing functional rVab, including phage packages or soluble entities as discussed earlier.

In this preferred isolation step, the rVab can have one of the following functional forms Fv(rVCvh or vl only), Fab, or scFv as described below:

a. Single functional VH or VL without (Fv) or with associated constant regions (Fvc) for the V heavy (CHn) and Vlight (CL or k) genes or parts thereof. Both types of F can recognize targets using only three of the six V region CDRs present in a natural Fab. In the preferred case, these Fvc genes are first packaged in fd phage and expressed with the C region (or some part thereof) attached, and in frame, being respectively a CHn, CL kappa or CL lambda) in which in all cases the constant regions, are devoid of their C terminal cysteine. There are a number of CH regions available including CH gamma, or delta, selected based on the required solubility and known to those skilled in the art. These V(or VC) genes can be expressed as soluble entities with or without tags or, as in the preferred case, fused, in frame, to one of the phage's coat proteins (i.e., gpIII) for functional display. These Libraries comprising only V regions are termed rFv and may be expressed packaged in phage for phage display. rFv phage libraries may be screened for members possessing CAP attributes of T, S and A and may be further diversified as described above. Such libraries with entities containing a reduced number of CDR or CSRs may be derived as part of the secondary simplification process when there are a very large number of active rVabs or when simplification is desired to foster the development of a more accurate BEEP.

C. Functional VH and VL combinations (rVab):

These combinations have two V genes with, or without, partial or intact constant genes. Although they may contain like members, the preferred combination is one VH (or VHCH) and one VL, (or VLCL). In the preferred method, $rVabT^{+}$ with the particular VH and VL couple are co-packaged in a single phage, on a single piece of DNA, as two individual gene products. For each phage, either VH and VL, may be expressed as soluble protein and the other attached to gpIII to cause surface phage display of the Fab. This coupling and expression of VH and VL can be made with or without identifying separately the VH phage library and VL phage library which can recognize the target when in the presence of a library of soluble VLCL protein or VHCH1 protein respectively (see, supra).

In one embodiment, the sequential procedure to obtain functional rVabs is as follows: Three individual libraries are made. Two of $\geqq 10^{7}$ phage packages each expressing and containing only one V gene (VHCH or VLCL) attached to phage for surface display. The other is of the same size but is made of VL genes expressed in lambda as soluble VL proteins which can be harvested from periplasm of bacteria expressing the VL soluble library. First rVabs are then made by mixing the soluble protein library with the VH phage library in solution prior to testing for target recognition. This mixing allows all VL proteins present to complex with any one VH expressed on a single phage surface package to form a phage attached noncovalent (disulfide bonds excluded) functional rVab. This allows the formation of all possible rVab combinations. To this mixture is then added the matrix associated target under study and after incubation, and complex formation, all phage carrying a matrix associated target displayed as part of rVab displayed on the surface of phage are isolated, preferably by one of the above noted panning procedures. Subsequent isolation of phage DNA gives an expressible library of functional rVHCH1 phage which can be $T^{+}$ (i.e., the $T^{+}$rVHCHhalfLIB).

All the VH phage library inserts, before or after phage amplification as needed, are next excised via simple endonuclease restriction digestion, and directionally cloned into a lambda able to express inserts as soluble periplasm proteins. After induction as noted above, the protein from the $T^{+}$rVHCHhalfLIB is harvested from the periplasmic space to give a protein library with the potential to form complexes with the entities within the other original phage library, i.e., the rVLCL library. After mixing the soluble protein library and this phage library, as above, the $T^{+}$rVLCLhalfLIB is isolated, as noted above.

In the final step of this embodiment, a combinatorial library of packaged pairs of $T^{+}$rVab is produced in which individual packages contain one VH and one VL pair of genes co-expressed as separate entities but associated together in functional rVab complexes. In the preferred embodiment of this procedure, these two genes are combined via the CRE-LOX recombinase system reported originally by Hoess [Hoess, et al. 1982, Hoess and Abremski, 1985; Hoess, et al. 1986] and recently by Griffiths et al. 1994, which are included herein by reference. In another embodiment, the package is also a phage, and expression is similar to the preferred embodiment but in this procedure, the combinations of rVHCH and rVLCL are made by excising and ligating in vitro the DNA in a fashion which allows randomization of VH and VL pairs but only one pair per DNA construct. These constructs can be phagmid or phage to allow either bacterial or phage expression of the rVab. In bacteria the rVab are isolated and tested by protein lifts, whereas in phage, the rVab is attached to a surface protein for display and assay. Both methods have been published [Hoogenboom, et al. 1991; Kang, et al. 1991; Waterhouse, et al. 1993; Figini, et al. 1994; Jespers, et al. 1994 ] and are commercially available in kit form (e.g. Stratacyte, CA). The preferred method is phage display of rVab.

The advantage of the embodiment in which active rVx-halfLIB are identified before combining them into rVabs, is that where combinations of VH and VL are made randomly from a preselected T+ active rVhalf library, the independent preselection of active VHCH T+ and VLT+ genes is likely to have reduced the number of active rVhalfLIB members to less than $10^{5-6}$. This reduction in number greatly increases the chances of deriving within a single phage library of $10^{12}$ members, which is attainable with the methodology disclosed herein, all possible active rVabs.

The procedure used to isolate single VH and single VL and pairs of VH/VL which recognize the target has the added benefit of being rapid, and controllable as to the strength and nature of Vab target binding that is desired. By the procedures outlined, a paired rVabT+ (containing $\geq$ about $10^{10}$ entities) can be generated.

The procedures discussed above result in the isolation of a) rVH or rVL, which alone do not need the other to recognize the target, and b) the recombinantly derived combinations of rVH and rVL termed rVabs and scFv which, in the later case, have rVH and rVL linked together by a short peptide chain and expressed as gpIII phage protein fusion products or even as soluble entities. Additionally, rVab in which both V domains are of one type, i.e., either $VH^2$ or $VL^2$ are possible by this invention. VHVH Fab have been reported with increased solubility. Altering CH1 for CH delta regions or changing specific and identifiable C amino acids, could also facilitate expression of novel rVabs.

The basic and preferred technology for cloning individual heavy and light chain variable regions either alone, or attached at their N terminus to leader sequences, or parts thereof, or at their C terminus attached to a constant region, or parts thereof, and placement into suitable expression vectors, transformation and expression in a compatible host cell in active form by recombinant DNA Technology are described in the art. See, Huse WO92/06204; Ladner WO90/02809; Winter WO92/20791, which are incorporated herein by reference.

To achieve high yield and faithful cloning of each active IgG, secretion of protein either as soluble extracellular protein or in the periplasmic space is suitable. In addition, protein may be expressed as an extracellular (or on the surface of phage) facing transmembrane or membrane-anchored functional protein which allows spontaneous dimerization of heavy and light chain intact IgG or V domains.

Methods of cloning from naive or immunized animals, entire spleen repertoires of Vab heavy (Vabh) and Vab light ($V_{AB}1$) in their natural or random pairings to derive enormously diverse combinatorial repertoire libraries are known in the art. [Huse, et al. 1989; Sastry, et al. 1989; Milstein 1990; Clackson, et al. 1991; Marks et al. 1991; Winter and Milstein 1991; Hawkins and Winter 1992; Hoogenboom, et al. 1992; Lerner, et al. 1992; Marks et al. 1992; Winter, et al. 1994].

B. Identification of rVab's Which Bind And Activate Targets (Stage 1b)

In a preferred embodiment of the invention, pairs of VH and VL antibody domains (rVab) are selected both as biological scanners of specific target surfaces and information reporters of activity related to the molecular 3D structure of the antibody site involved in surface interactions as well as the molecular 3D structure of the active elements of the binding site. This structural information is relevant to identifying the minimum structure of the LIGATT, which would need to be incorporated into a SOMER or DISOMER, to reconstitute the CAP of the active rVab and regulate the target in the desired fashion. This invention identifies the unique ability of rVab when used as libraries containing at least about $10^{10}$ members to identify those portions of a target's surface connected to function in such a manner as to immediately provide the tools necessary and sufficient for screening for organic replacements at the target with a desired CAP. In addition, an embodiment of the process uses genetic algorithms to construct 3D high resolution molecular models of the shapes of organic molecules which can fit into the active target and regulate activity so as to electronically screen for or synthesize via computer programs SOMERS or DISOMERS.

Active target landscapes are those surfaces connected to target function as defined as those able, when occupied by a ligand, of influencing target activity. It is known that antibodies, in a wide variety of forms, e.g. Ig, $Fab_2$, Fab, or sFv (i.e., VH or VL alone), have exceptional selectivity as well as high affinity for their targets. This invention uses rVab which are identified as possessing the desired CAP attributes in two ways. Structural characteristics of multiple rVab's identified as possessing the desired CAP attributes are combined to produce a composite structural map which is used to define a BEEP. In addition, individual rVab's which are identified as possessing the desired CAP may be labelled so that they may be used as reports in competitive binding assays to identify SOMERS, DISOMERS or other ligands active at the pharmacological target.

1. Identification of rVab's with TSA+ For Targets Having Endogenous Ligands

The approaches to isolation and identification of Vab for targets having endogenous ligands and rVab processing all TSA+ attributes, are divided based on two fundamental issues: first whether the rVab induced target modification is allosteric (alloA) or competitive (compA) with the native signal (endogenous ligand) and second, whether the active surface is a simple or complex landscape found one or more different submits of the target. Target modification is considered anything which alters target activation by any means including native signal recognition (i.e., signal binding) and/or the signal transduction process directed by the active target. For example, the binding of ACh to the muscarinic subtype 1 receptor and the interaction and activation of the Gi protein, respectively. In both cases, the process uses libraries already selected for, preferably by batch mode selection, target recognition i.e., rVabT+, Batch mode selection is preferably than used to identify and separate rVabT+A+ from those which are inactive under specified conditions. Libraries of $10^6$ to $10^{12}$ individuals are used and the process is therefore applicable to rVab libraries which have both) TH and VL chains, noncovalently (as Fab) or covalently attached (as scFv [Hoston, et al. 1988; Bird, et al. 1988; McCafferty, et al. 1990; Hoggenboom, et al. 1991; Barbas, et al. 1991; Garrard, et al. 1991; Breitling, et al. 1991] or diabodies [Holliger, Prespero, and Winter, 1993] as well as those with only one V chain. By methods known to those skilled in the art, individual rVabTSA+ within an active rVab A+ library (LIB) can be simply and rapidly isolated, assayed, tagged and used to screen various chemical libraries for SOMERS which compete with rVabA+ for binding to the target.

For allosteric Vab-modulators, the presence of allosteric activity within a rVabT+ library is indicated by the occurrence of an alteration in the association between rVabT+ and the target induced by the binding to the target of another entity. This entity could be the native signal or any known target effector entity. Examples of allosteric entities include such nucleotides as ATP for receptor containing kinases, or GTP for G-protein associated targets, or a protein which couples to the target during signal transduction such as G-proteins, or even other receptor subunits.

a. Identification of rVabTSA+ from rVabT+ using allosteric modifiers The isolation of rVabTA+ from rVabT+ is tied directly to the action of the signal at the target. In the preferred process, matrix-linked target (m-Tr) is mixed with the rVabT+ and incubated so as to allow m-Tr:rVabT+ complexes to form. In general these are the same conditions used to isolate rVabT+ in Step I (b). After sufficient time to allow appreciable complex formation, which may or may not be sufficient to allow the interaction to come to equilibrium, the temperature is lowered to about 4° C. so as to trap bound rVab in the m-Tr:rVab complex by slowing its dissociation rate. With the temperature at 4° C., free rVab is rapidly washed away and the complex is resuspended in original buffer. This process is done quickly and uses a matrix such as, for example beads or plastic surfaces, and takes <1 min. For this process, preferentially one first determines or estimates the normal dissociation rate of rVabT+ from the target. This may be determined by methods known to those skilled in the art. For example, in parallel reactions, the dissociation constant ($k_{-1}$) for target (Tr) and signal are determined using either a labeled target (T*) and monitoring the dissociation of T*-rVabT$^+$-matrix complexes, or unlabeled target and following its release from the rVabT$^+$-matrix complexes using anti-rVab constant region antibodies (or anti-phage antibodies) or by simply assaying phage in the supernatant if a rVab phage library is used. The half time ($t_{1/2}$) for $k_{-1}$ at 4° C. for rVabT$^+$ library from the target, for the entire population, is then determined.

With the $t_{1/2}$ for $k_{-1}$ known, a new population of washed rVabT$^+$-matrix complexes of the entire rVab library are formed at 4° C. and allosteric effectors are added in saturating concentrations. Half the population is centrifuged to isolate the free rVabT+ members from the library which remain in the supernatant within about the first minute (or $\leq 1/30$th) of the population's dissociation $t_{1/2}$. The remaining half is allowed to dissociate for about $10 \times t_{1/2}$, centrifuged and the pellet resuspended and allowed to dissociate for about another $10 \times t_{1/2}$ to isolate the second population of free rVabT+. In both cases, centrifugation is used to rapidly isolate the free rVabT+. In the first instance the free rVabT+ library is enriched for those rVab members induced to rapidly dissociate, referred to as rVabT+A+ allofast, while the second is enriched for those which have been induced to dissociate slowly, referred to as rVabT+A+ alloslow. Each is thoroughly washed. and then recycled through the above isolation procedure a second time. Such enrichment cycles are continued until a clear change in entire populations $t_{1/2}$ for dissociation is seen at which time the population is termed rVabT+A+ (fast or slow). Their numbers are then determined, if need be after amplification. If these populations are s mall, individual rVabT+A+ (fast or slow) can be isolated at this time and assayed directly in subsequent procedures. If large populations are obtained, they can be analyzed in subsequent steps to isolate subpopulations which have other desirable target attributes, e.g. specificity (S+) among one of a large number of target family members.

b. Identification of rVabT+A+ from rVab Library Using Competition Assays

The second approach to isolating rVab capable of target modification is used for the isolation of rVabT+, whether or not the S properties have yet been determined, which are target regulators which bind to targets at the same domain or at a domain overlapping with that used by the target's natural signal (nS) endogenous ligand. These are considered as competitors with nS for binding to the nS binding domain, and therefore are competitive modulators, not allosteric modulators. Both agonists and antagonist replacements for endogenous ligand will be found within this population.

This process requires the use of a high affinity nS which is labelled (nS*) and capable of rapid and quantitative isolation. There are many such labels possible, one is biotin, another, for example, is the small antibody epitopes for which high affinity sera (or monoclonal antibodies) exists commercially. Methods of making such a labelled nS and the available epitope/antibody combination for protein signals and organic molecules are known to those skilled in the art. Labelling is a relatively easy procedure for protein nS. For organic molecules it is much more difficult but in the preferred cases where labelling has not yet been done, non-neutralizing monoclonal antibodies or biotin will be used by methods known to those skilled in the art.

The preferred process of identification and isolation of competitive rVabT+ (S determined or undetermined) which is outlined here uses biotin as the nS label ("tag"). The process works similarly using other labelling tags such as iodination with $^{125}I$, or $[^{32}p]ATP$ phosphorylation.

The biotinylated high affinity signal, $nS^{tag}$, and the rVabT+ library to be tested (previously isolated and identified as T$^+$) are combined with a soluble active form of the target (Tr) and incubated so as to allow formation of significant numbers of $nS^{tag}$:Tr as well as rVab:Tr complexes. The incubation conditions used here are those previously used to allow binding of the rVab library to m-Tr as long as these conditions also allow $nS^{tag}$ binding to Tr. The temperature is then lowered to 4° C. and all $nS^{tag}$ and $nS^{tag}$:Tr complexes are removed from solution with strepavidin (or another tag recognizer coupled to some matrix). The supernatant, containing T:rVabT+ complexes and free rVabT+ is affinity separated to isolate only Tr:rVabT+ by either panning over anti-Tr antibody coated dishes or passed through anti-Tr antibodies coupled to agarose. The anti-Tr antibodies used in this step do not alter rVabT+ binding to Tr. Such antibodies are known to often be those which have epitopes at either the amino or carboxy termini of the Tr under study or some other non-modulatory (i.e., non-active) target domain. The population of rVabT+ bound to Tr in solution and obtained by association with anti-Tr antibody on their own matrix can be isolated and recycled through the above procedure any number of times for enrichment and amplification. This population contains all rVabT+ library members which bind to Tr at the binding site used by the target's nS. This population is therefore made up of rVab which bind to the nS binding site and will be labeled rVabT$^{+comp}$. Even though at this point these active rVabs are uncharacterized as to agonist or antagonist activity, their classification as active rVab is appropriate based on the definitions and disclosure of this invention.

Individual entities within these populations may be isolated, tested for agonist or antagonist activity using standard in vitro, cellular or in vivo assays known to those skilled in the art, and/or labeled by procedures known to those skilled in the art and used for screening for agonist and or antagonist SOMERS. Furthermore, where a labelled $nS^{tag}$ exists for Tr, individual rVabT+A+compt will be tested for competitive modification of $nS^{tag}$ binding to T by methods known to those skilled in the art.

c. Isolation of rVabT+ Which Are A+ By Allosterically Modifying Targets

The next process outlines the isolation of rVabT+ which allosterically modify Tr (i.e., are A$^+$) by binding to sites which do not alter nS binding but do alter the ability of the target to be active even for targets devoid of native signals.

In these cases, active rVab will be isolated by virtue of their ability to alter the association of T and some component of the signal transduction system used by the target. For G coupled receptors, that would be the GTP-G protein complex; for targets with catalytic or stoichiometric enzymatic activity that would be nonhydrolyzable substrate analogs; and for channels or transporters it would be ions, molecules transported, electrochemical gradients or other channel subunits. In these cases the isolation of this type of rVabT+A+ would occur either by a) testing in batch mode limited sized libraries i.e., rVabT+A+ for agonist or antagonist action in vitro; or b) isolating in batch mode those which altered Tr activation, i.e. phosphorylation, binding of ATP or GTP, or binding of other proteins involved in signal transduction as outlined above. Library members which are T+A+ may be diluted and retested until single entities are identified.

d. Identification of rVabT+A+ Pairs When Single rVabT+A+ Are Not Identical

If no single allosteric or competitive rVab is found in cases where an nS exists by one of the above approaches, the following procedures are capable of identifying pairs of entities which, are both required simultaneous as the necessary condition for modification of the target. In these procedures, the pairs of entities tested will be provided by two differentially identifiable rVab libraries or preferably one rVab library and another large and highly diverse library of identifiable molecules. For targets with large protein signals, such as growth factors cytokines, etc (i.e., >10,000 D) which may be expected to have more than one LIGATT this dual modifier assay will be the preferred approach in one of two general alternative forms.

The basic procedure will be described first using two differentially labelled rVab library as sources of the two paired modulatory entities. In addition to the rVab libraries there are both a labelled Tr (Tr*) and a labelled high affinity signal (haS) which are also recognizable independently and separably from each other as well as from the rVab by high affinity probes. In each case, recognition of target occurs whether or not these entities are part of any type of Tr complex but does not perturb the target's ability to bind haS* or rVab. For example, the labelling epitope contained within the Tr* could be one which is recognized by a high affinity Ig at sites commonly known to those skilled in the art as non-neutralizing epitopes. Large protein targets are known to encompass such sites within internal peptide sequences, N- or C-terminus or unmodified or modified amino acids. These epitopes need only be exposed during complex formation and non-active, i.e. unable to modulate target binding of nS when occupied by recognition antibody which can be easily established in each case.

For signal labels, either biotin or an integral Ig epitope, are the preferred label, allowing avidin- or Ig-agarose respectively, to be the quantitative recovery probe as long as the labels do not significantly reduce affinity for the target. Other possible labels include identifiable peptides or protein sequences, such as substance P, partial HSV viral coat protein sequences, and enkephalin. The antibodies for such small epitopes or peptides could be either polyclonal or monoclonal Ig, commercially available or rVab as procured by the recombinant methods referred to for targets disclosed herein. Biotinylation of various signals and testing for non-interference with native target signal binding to Tr is available by many methods known to those skilled in the art.

Using an Ig epitope labelled or tagged Tr (Tr*) and a biotin-labelled high affinity signal (haS), the identification and isolation of a pair of modulatory entities (in this example both are rVab) is initiated by combining sufficient numbers of two previously isolated large $rVabT^{+}$ populations, each with a specific Ig epitope (epitope 1 for rVab1 and epitope 2 for rVab2), with the $haS^{biotin}$ and the epitope tagged Target (Tr*) to allow formation of the trimeric rVab1:T:rVab2 complex which does not bind $haS^{biotin}$.

rVab1 and rVab2 may be added initially at a variety of about equal concentrations from $10\times1^{1}$ down to $10^{-4}$ M. The lowest concentration at which target activation occurs will be used for subsequent manipulations. The upper number is arbitrary but should theoretically exceed by about 30 fold the concentration needed for rVab1 or rVab2 to bind to Tr so as to saturate the site and prevent binding of haS*. The mixture is then allowed to incubate at room temp for at least approximately 6 hr, or overnight and then saturating amounts of avidin-agarose is added and the mixture centrifuged and the supernatant, devoid of any free $haS^{biot}$ or Tr:haSbiot complexes, is removed for subsequent use. The supernatant, containing dimers of Tr:$V_{AB}$1 and Tr:$V_{AB}$2 and the desired trimers of $V_{ab}$1:Tr:$V_{ab}$2 are then panned over anti-T Ig attached to a solid matrix or support such as for example, plastic culture dishes or agarose column matrixes.

Identification and isolation of Tr complexes having both rVab1 and rVab2 concurrently bound can be made by panning successively over matrixes coated with anti-rVab1 and then anti-rVab2 Igs. Phage displayed rVabs isolated by this procedure can be separated, amplified and then used for secondary cycling through the above isolation procedure. Finally, individually purified phage are tested in identified combinations for competition of hastag binding.

In the above case, the two rVabT libraries (i.e., rVabT1, $2^{+}$) can be easily distinguished for example by utilizing the CH1 domain of humans on one and the CH1 domain of mice on the other. Ig specific for human and mouse CH1 are available commercially. Use of other constant regions from one specie is also possible.

e. Use Of rVab-Peptide Libraries And Other Probes To Identify Multiple LIGATT Targets i. Identification of First Ligand for a Multiple LIGATT Target There are a number of variants to the above procedures in which the second entity of the pair needed to compete for $haS^{tag}$ binding would not be another rVab but instead would be a member of another library containing diverse small organic molecules, peptides, nucleic acids, carbohydrates or even natural products. Excluding the possibility of stearic hinderance, the frequency in the rVab library of entities which bind to a target in a modifying manner (given their paired entity is also present) should be no different than that for rVab which are able on their own to bind to Tr surfaces and modify signal binding. Accordingly, rVab libraries of the size generated by this invention may be used to identify both rVab members of the sought after pair. All of the libraries stated above having in excess of $10^{11}$ members/ml should be suitable for use with this invention provided the frequency for each binding event is not less than $10^{-5}$. A useful library or pair of libraries should contain sufficient members so that two binding events will occur simultaneously on the same Tr, the condition necessary for inhibition of haS* binding, at less than about $10^{-11}$ and therefore be present at least once per reaction. If the frequency of each event is greater, i.e., $10^{-4}$ or $10^{-3}$ then these modulatory complexes will occur as frequently as 10 to 100 times per assay. As the purification of an active phage displayed rVab per cycle is $10^{-2}$ to $10^{-3}$ then up to 4 cycles may be needed to purify the active entity. To obtain one member of the pair, one only has to purify from the final step, one of the two rVab entities. When other libraries are in use as the source of the second pair member, they need not be isolated at all.

ii. Identification of Second or Subsequent Ligands for Secondary LIGATTS of a Multiple LIGATT Target Once one member (primary member) of the pair is identified, which in the above case would be a rVab the isolation of the second is made straightforward by using the first member, at saturating concentration in all reactions. This simplifies to a search for a single entity, which for a rVab, would be done as outlined above. However, when one rVab of a pair is in hand, one can search through a chemical as well as a rVab library for the second member of the pair of Tr binders which regulate Tr activity when simultaneously bound to the target. Each member of the pair, particularly those which are identified as members of a chemical library, are potential candidates as one half of a pair of small organic molecules, one for each active surface domain required for target regulation, which when covalently linked together would provide a single active organic molecule referred to as a DISOMER. Such DISOMERs would be valid interesting drug discovery leads.

Another protocol for identifying an active pair, i.e., a pair which is necessary and sufficient to bind to Tr in such a manner as to displace $haS^{tag}$, is to perform the original incubation of tagged target (Tr*), high affinity target signal (haS) and target binding rVab (rVabTr1 or Tr2$^+$) in the presence of excess labelled Tr* to reduce to a minimum the presence of unbound rVabTr1 or Tr2$^+$. If these incubations are done in the presence of haS at about a 100 fold excess of the Tr-saturating dose, the only rVab in solution will be those which has been competed from binding by haS. Accordingly, those rVab prevented from binding to Tr by haS, should, with high probability, be those which can prevent haS binding to Tr and are expected to possess the desired activity. As bound rVab can be separated from free rVab via panning over anti-Tr Ig (or avidin with a biotinylated Tr), upon such removal of all rVab:Tr* complexes, the only rVab remaining in solution will be those pairs which when bound together, and possibly individually, prevent haS binding. Recycling of the supernatant additional times through such a paradigm will eventually result in identifying the rVab pair or at least one of its members if another type of ligand is used as the source of the other half of the active pair.

iii. Use of rVab-Peptide as Surface Scanners

For signals such as protein hormones and growth factors, where dimerization or timerization of identical (i.e., homoligomeric) or different (i.e., heteroligomeric) receptor units is required for receptor activation. This invention solves the problem in one embodiment by creating bivalent rVabs which allow for the isolation of bivalent active rVab surface reporters capable of identifying each receptor subunit endogenous ligand TARGATT attachment site. In this process, identification of bifunctional active surface reporters, proceeds by taking a plurality of rVabs which have previously been identified as recognizing either a particular limited surface of one of the target's subunits (i.e. are T$^+$), or a larger number of one or two selected groups of amino acids which are known to be involved with endogenous ligand binding. The genes encoding these rVabT$^+$ ligands are modified to encode for a flexible amino acid which attaches in frame to one end of either the heavy or light chain construct, a library of small random peptides to create a bifunctional scanner (rVabPEP). In one embodiment, the peptide is encoded by DNA used to that encoding the heavy or light constant domains. In another embodiment an rVab is expressed with at least two peptides for identification of trimeric receptors.

In a preferred embodiment, a bifunctional scanner library consisting of rVLCL and one rVHCH1 is constructed to identify rVab-PEPs which recognize an active surface consisting of two TARGATTS on the surface of the target. rVab-PEP are then isolated in batch mode and individual member are subsequently identified as active competitors for endogenous ligand binding. Such rVab-PEPs do not significantly bind the target in the presence of excess endogenous ligand. These bivalent rVab-PEPs will then prebound to target will prevent binding of the target endogenous ligand which has been immobilized on a solid matrix.

For homodimeric receptors where each target subunit has a TARGATT which binds to the ligand (as per Growth Hormone Receptor, GHR), rVab-PEP would be isolated. The rVab portion of a first active rVab-PEP is then labelled for use as a reporter to identify SOMER replacements for the LIGATT which resides within the rVab portion of the active rVab-PEP entity and recognizes one TARGATT on the surface of the receptor. To identify a second SOMER replacement for the second LIGATT of the rVab-PEP entity, which resides in the PEP portion of the rVab-PEP entity, a second rVab without peptide is identified from the library of active rVab-PEP which competes for binding with the peptide portion of the first rVab-PEP. The process of finding the two rVab which correspond to the two LIGATT residing within an active rVab-PEP entity is referred to as rVab Pairing. The second rVab is then labelled for conversion to a reporter for identification of SOMERS for the second LIGATT site.

Where the targets are heterodimers, the preferred approach is as follows. The rVabT$^+$ for receptor subunit surface I, are grouped based upon recognition of common domains and/or surfaces containing amino acid known to affect binding of endogenous ligand. These rVab's are then expressed as rVab-PEP as described above to generate a series of bivalent ligands. Members of this rVab-PEP library which are displaced from target by endogenous ligand and which also displace endogenous ligand from the target are selected as above for homodimer receptors. A limited number ($\leq$about 10) of rVab-PEPs with endogenous ligand displacing activity at the target are then selected for identifying a ligand for the second (II) binding site. An alternative selection method for identifying site I ligands is to select rVab-PEPs based on their ability to activate target. Activation may be detected as described above based on modification of an allosteric effector or on some other detectable change associated with receptor activation. For example, activation may be associated with self phosphorylation or dimerization. rVabs for the second TARGATT site on the second receptor subunit of the heterodimeric are identified in one embodiment, by expressing rVabs as a rVab-PEP library using rVabs previously identified as being competitive for the endogenous ligand at site II. The resulting rVab-PEP library for site II is then tested for activity as described above and active members are isolated.

V. Identification of rVab which are Selective (S$^+$)

In order to isolate those rVab which are selective for and distinguish among closely related members of a target family or any target of concern (i.e. selective), the following batch mode selection procedure may be used. The rVabT$^+$ under investigation is mixed with matrix immobilized target (m-T) and allowed to form complexes in the presences of soluble peptides, recombinantly obtained protein fragments or intact targets whose identical (or related) sequences or conformations are found in targets for which the investigator does not wish the rVab to bind. These sequences are typically between about 6 to 12 amino acids in length and are present in the targets for other endogenous ligands of the same gene family. After sufficient time for complex formation the rVabT⁺ still bound to matrix are isolated by panning and preferably recycled 2–3 times for enrichment as noted above to derive rVabT⁺S⁺. This procedure can be done before or after any of the above procedures related to isolating Active(A⁺) or Target recognition positive(T⁺) library members.

If all screens for T, S, and A are accomplished, the final library would be rVabT⁺A⁺S⁺ given that there was only one LIGATT and one TARGATT required for regulation of the target and thereby represent individual entities which describe target sites suitable for screening for SOMERS with all three attributes of a CAP. Where there are more than one LIGATT and one TARGATT required for target regulation, i.e., when the target is multimeric or even monomeric but contains multiple TARGATT domains, the full CAP, including activity (A+), can only be observed with a bivalent rVab, such as would be found in an active rVab-PEP. In such cases, the rVab portion of the active bivalent rVab would not be active on its own. Nevertheless, since it still can identify SOMERS we refer to it as A*.

Clearly, high affinity (less than or equal to about 30 nM) and selective target recognition do not require the antigen pocket of the Vab be made up of two V domains as found in native Ig molecules but can exist in single VH domains containing only 3 CDRs. Based on the information in the art, improvements in making useful single chain (rVvx; i.e., vh or vl) with $T^+$, $S^+$ and $A^+$ properties are expected by utilizing constant domains other than CH1, i.e., using gamma 2 or 3 or delta. This invention also recognizes the need for solubility of the recombinant proteins used to construct the members of the rVab, rVvx and rVab-PEP libraries. To be acceptable, changes in solubility would not adversely effect VH; VL structure in an rVab.

When using single chain libraries, select the rVvx entities which modify pharmacological target activity via binding to its surface. Refer to these as the active $rVvxT^+A^+$ libraries (LIB). Isolate actives based on:

i. those whose binding is modified by the presence of the endogenous ligand;

ii. those whose binding is modified by any allosteric regulator of the target iii. those whose binding alters target (i.e. target phosphorylation or association with G proteins).

In the case of i and ii, actives are isolated as soluble entities and in iii precipitated by anti $PO_4$-protein or G-protein antibodies. In i endogenous ligand is used ad 300× Kd. In all cases harvest positives, amplify, and reisolate.

Group as to common surface domain recognized by rescreening active $rVvxT^+A^+$. LIB against target in presence of small peptides (10–12 amino acids) or large peptides made recombinantly (20–50 amino acids) which define the target domain. In this assay, those soluble in presence of peptide are grouped together, and all data are used to construct an antibody surface map.

The members of the rVab library which are particularly useful in automated binding assays and screens for SOMERS at preidentified target sites possess preferably the following characteristics.

a. ≦30 nM affinity for target;

b. recognized target sites are smaller than those used by endogenous ligand signals;

c. possesses agonist or antagonist activity when bound to an active landscape whether it be those used by endogenous ligand or allosteric sites;

d. specificity for binding to only one among many related members of a target family;

e. little nonspecific binding to unrelated targets and substances related to the assay itself;

f. easy and homogeneous and single tagging with a label;

g. labelling which allows both rapid and sensitive quantitation of target binding and;

h. a framework of known structure which delineates the location in space of the contact points of the reporter with its target.

The latter attribute is critical to the solution of the 3D structure of active SOMERS as it allows the problem of deducing the 3D-shape of the LIGATT on the target surface scanners which are active and in contact with the target to be solved after obtaining the one dimensional linear amino acid sequence of the reporter with the use of genetic algorithms. The 3D landscape of the LIGATT on the active rVab is directly transformable into a 3D landscape of the sought after SOMERS.

VI. Identification of Biologically Enhanced Ensemble Pharmacophores (BEEP)

A. Combine structural information from identified members of library possessing desired attributes of potency, activity, selectivity, and specificity In trying to identify useful rVabs and to deduce the structure of the BEEP, the ability to genetically simplify (e.g., reduction in number or size) or further diversify (e.g., increased number of randomized amino acid positions, or increased size) of CDRs and CSRs within active rVab libraries or within one rVab is of critical significance. This is because not all contact amino acids contribute the same energy to antibody binding and sometimes one amino acid can account for >99% of binding energies. Just the 3 CDRs of one VH can provide 10–100 nM of Ig target affinity. rVab phage libraries of about $10^{12}$ members with secondary diversifications in any number of regions can be derived from a small number of active rVabs found initially by processes of the invention previously described, by PCR as used to construct the rVab library (see below) and or oligonucleotide insertion, known to those skilled in the art to provide an acceptably large enough source of target surface scanners and reporters as envisioned by this embodiment of the invention. In addition, it is clear that active surface scanner rVab will be needed which recognize different local surfaces on the target in order to generate sufficiently large amounts of one dimensional amino acid sequence information so as to accurately deduce a BEEP which is not only accurate for predicting the structure of one SOMER but is capable of predicting the ensemble of active SOMERS which can attach to that site.

A particularly novel aspect of this invention is that it establishes a way for the CDR regions of a VH or a VL alone or complexed together as rVab to be reduced to a minimum structure which occupies the target sites recognized by the rVab and have a desirable CAP. An advantage of identifying such a minimum structure is the potential reduction of target affinity to a level which is competable in standard binding assays by endogenous ligand and potential SOMERS and of the number of critical atoms participating in target contact. The smaller the number of contact points the simpler the resolution of the BEEP.

B. Create Beeps For Each Active rVab Subset

According to this invention, BEEPS are created which contain the coordinates and attributes of the active elements of the 3D surface of active SOMERS for a particular surface domain on particular pharmacological targets. The starting point for this is grouping together of rVabT$^+$S$^{30}$A$^+$ members of the rVab library according to common target surface domain recognized which in the first instance will be that which is overlapping, or identical to endogenous ligand.

In a preferred embodiment:

a. Each surface group is partitioned and one rVabT$^+$S$^+$A$^+$ for that group is isolated. The VHCH gene is then cloned out and used to derive a new combinatorial library. To derive this new combinatorial library the cloned rVHCHn is paired with all rVLCL for rVab members which bind to the common surface.

b. Isolate via panning (as done for the original LIB) all new combinational rVab members (i.e., rVHCH$^n$: rVLCL$^n$ . . . rVab) which are T$^+$S$^+$A$^+$ for the original common target surface domain. This library is called rVab$_{VHn}$. Repeat for each VHCH in the original rVab thereby deriving a rVab$_{VHn+1,n+2,n+}$ . . . set which identifies all related VH and VL for a particular surface domain. These libraries will provide multiple combinations of defined VH genes with all VL's for a given surface. Alternatively, these various libraries may be made by identifying specific VL genes and cloning them into libraries containing all VH genes identified for a given surface target.

c. Determine via PCR the amino acid sequence of all VL in the set which can bind to all VHs in the library.

d. repeat a–c for all active V$_H$ using [V$_L$]$_{n,n=1n=2n+}$ . . . .

e. The spacial coordinates for the framework of the parent antibody in which all randomized CDRs were placed, along with the coordinates of the various CSR and CDRH3 for the active VH and VL for those entities found in the particular local target surface domain rVab library under study along with the amino acids identified in these CSRs and CDRs are solved in a genetic algorithm to determine the 3D conformation of the pharmacological target landscape occupied by all active rVab members which recognize the same surface domain. This solution is a biological enhanced ensembled pharmacophore (i.e., a BEEP)

f. Repeat for rVab library for other local active target surface domains.

g. If any data base is not sufficient, take the relative set of VH genes and excise their CDRH3 domain and replace with a random oligonucleotide encoding a peptide library of preferably 8 to 10 amino acids. The potential size of this library is between about $8^{20}$–$10^{20}$ members. Repeat selections to obtain new diversity enhanced LIB.

C. Use of genetic algorithms to create BEEPS

Creation of the BEEP begins after isolation of a set of active rVabs {Vi}i=N, which contain members (Vi) which have been verified as having the desired attributes of affinity, selectivity and activity at the target, where N=the number of such members within the set. In the preferred instance, each active rVab will have all three of the above attributes, but it is also possible that only two, or only one, of the attributes will be desired and therefore will be present. For this description, TSA+ will refer to the active rVab irrespective of which attributes are present. Each TSA+ rVab member is then isolated and its amino acid sequence determined using procedures known and available to those skilled in the art. For example, commercially supplied kits and an automated sequencer (ABI, USA).

According to this model, it is assumed that an active target surface binds different rVabs, through the same site of the target surface, and accordingly, at least a subset of those rVab are expected to possess similar surfaces. Thus, finding a recurring, i.e., common, surface motif (which we refer to as the BEEP) in different rVabs indicates either: a) the common rVab surface plays a role in target: rVab interactions; and b) that this interaction could be duplicated by other molecules with similar surfaces. Therein, it is a common surface which is responsible for the common phenotype of at least a subset of the L$_i$ members of the original set of TSA+ rVabs. There may be one or more common surfaces within the original set of TSA+ rVabs. This duplication takes the form of the BEEP first, and subsequently small organic molecules.

Given such a collection of TSA+ rVabs and their amino acid sequences, a preliminary set of surface scanners {L$_i$}$_i$=N, where each L$_i$ is a model of an antibody molecule, is constructed according to the invention using the canonical structural principals of Chothia (Chothia and Lesk 1987, Chothia 1989, and Chothia 1992) and the information on the crystalline form of the parental antibody used as framework for construction of the rVab library as described by this invention, N is the number of such TSA+ rVab surface scanners which define the fundamental geometry which is the position of surface atoms within acceptable distances from each within a generally known structure. Shape descriptors rely on known CSR and CDRH3 shapes, and the amino acid sequence within these domains. Subsequently, chemistry characteristics, such as charge, hydrophobic interactions, exposed/buried surface area, hydrogen bond formation etc., known to those skilled in the art will be considered.

In the preferred case, each TSA+ rVab contains one VH and one VL chain, with 6 complementary determining regions (CDR) wherein three (CDRVL1,2,3) are within VL and three (CDRH1,2,3) are within VH. Furthermore, in the preferred case, there are the 5, 1 and 6 different canonical structures consisting of a different known canonical loop structure possible for every CDRVL1,2 and 3 respectively, and 3, and 4 different canonical structures consisting of known canonical loop structures possible for every CDRH1 and 2 according to the invention. The CDR for H3, although not canonical, in the parental library will have one of three defined structures in its parental mode before the amino acids positions within each are randomized. Furthermore, the prior knowledge of rVab framework and relationship of the 6 CDR domains within the framework provides additional structural information for constructing an L$_i$ and eventually a BEEP. In addition, as the number of known antibody structures increases, new canonical structures become known and may be incorporated into the rVab libraries to allow isolation of TSA+ rVabs containing such structural loops.

Each L$_i$ can be represented, for the purposes here, by the atomic coordinates of the constituent atoms of the rVab which is a member of TSA+ set. The surface (S$_i$) of the preliminary model L$_i$ can be parsed by its CSRs and CDRs wherein $$S_i \cong [(CSR1)_i, (CSR2)_i, (CSR3)_i, (CSR4)_i, (CSR5)_i, (CDR6)_i]$$

wherein 1 through 5 denote CSRVL1, 2, and 3 and CSRH1, 2, and 6 denotes CDRH3, respectively, and wherein with each (CSR)$_i$, for L$_i$ there is a particular sequence.

The surface (S$_{ij}$) can be repositioned and reoriented in space by transforming the atomic coordinates of the Li according to: $S_{ij} \cong G_{ij}*L_i$, where L$_i$, is a model of surface scanner i defined by the coordinates of its constituent atoms and G$_{ij}$ is a matrix that transforms L$_i$. Furthermore, G$_{ij}$ is parameterized by the translation and rotational parameters ($\Psi_i$, $X\chi_i$, $\omega_i$, $x_i$, $y_i$, $z_i$)j. Thus, as scanner i is rotated and moved into a new position j, and the CDR are carried along with it.

The genetic algorithm of this invention, referred to here as DIOGAM, takes the initial set of $\{L_i^o\}$, where the superscript ($^o$) means 'preliminary model', as input data to produce from that data as output the theoretical common surface (i.e., the BEEP) which represents the best overlap in terms of chemistry and geometry for members of the set.

In general, a genetic algorithm (Holland, J. H., 1992 and Goldberg, D. E. 1989, which are herein incorporated by reference) operates on 'genes' to produce variation which through selection yields 'survivors'. The genes of survivors (as judged by 'fitness') are then mutated to produce newer progeny for further fitness selection. Thus, mutated genes, according to the genetic algorithm of the invention DIOGAM, are produced and encode altered surfaces, which in turn are altered phenotypes.

The definition of a "gene" for use in the model of this invention is a specific sets of values for the parameters of $G_i$: ($\phi_i$, $\chi_i$, $\omega_i$, $x_i$, $y_i$, $z_i$)j. Varying these parameters changes the position of the surface Sij which we define here as the phenotype of the given gene.

Herein, $[\{G_i^o\}]j=1,M$ is a population of M variations of the model Li, which encompass all possible ways to vary the surface of the model, on each member of the TSA+ rVab set which gives rise to subsequent models (1st progeny generation, 2nd progeny generation, nth progeny generation models [1–n]) wherein n=the number of the generation.

The initial creation of preliminary models follows in one embodiment the Computer Vision algorithm for structural and surface comparison of proteins (Fisher et al.; 1994) using a small number of points, rotational and translational in nature for unique definition. This method is based on the previous method of the Geometric Hashing Paradigm (Lamdan and Wolfson 1988 and Lamdon Schwartz and Wolfson, 1990). This method finds 3D motifs within different segments or by isolated single amino acids, independently of any linear sequence of amino acids. The later provides for incorporation of all important amino acids or groups thereof located within the 5 CSRs and 1 CHDH3 and which by themselves do not occur in a singularly linear sequence within any rVab.

Using only distance invariants, this program obtains data from surface superpositioning which is then used to solve for portions of the rVab which represent analogous portions of surfaces of ligands directly involved in ligand-target binding requirements, i.e., the 'docking problem.' Various types of surface superpositioning can be used, and includes docking of rVabs, one rVab and one target, and one rVab and one target related ligand. DIOGAM uses an efficient automated computer vision based technique for detection of three dimensional structural motifs (Fisher, D., et al., 1992; and Bachar, O., et al. 1993). In this process, seed matches are found first, based on the Geometric Hashing Paradigm, the clusters of seed matches are found using rotational and translation parameters to fix 3D motion. Here the seed matches will be done within specific sized balls, using different pairs of balls, the subsequent clustering added by known CSR structure and CSR and CDR relationships within each rVab. Extensions will be extensive, eventually including all amino acids within each CSR and CDR, using reiterate ever growing cycles.

Such clustering and extension (referred to here as additional level mutations (see below)) can be used for both chemistry and energy analyses. Modeling will initially be done individually, then in an aggregate manner.

Therein for each progeny generation, the sum of $\{S_{ij}^n\}$, wherein j=jth member of the ith scanner as appearing in the nth generation gives us a Target Fitness Landscape ($T_i$): which is a set of numbers representing chemical and geometric properties of the maximally overlapped set of $S_{ij}$. For the purposes of this invention, Tn is a vector whose components, tj, include but are not limited to scaled electrostatic energy, buried surface area, hydrogen bonding, and local curvature.

As the algorithms proceeds, it calculates at each stage, the target fitness landscape (T) and ascertains a mutational strategy for the next stage. Thus, depending upon the strategy, all N genes are mutated, producing new phenotypes for which a new value of T is calculated. The process is complete when T can be maximized no further.

Thus DIOGAM alters the set of $\{\phi_i, \chi_i, \omega_i, x_i, y_i, z_i\}$ in order to achieve the best overlaps in the general sense (geometry, energy and chemistry) and the result is new Target Fitness Landscapes (i.e., T) defined to be a minimum when maximum generalized overlap has been achieved.

The next or intervening phases of DIOGAM allow variation (i.e., mutation) in the Li themselves thus the genetic algorithm include s genetic varation of CSRs and CDRs. For DIOGAM, the mutated gene (i.e., the augmented or varied gene) is the collection of rotamer angles of the side chains themselves within the CSRs and CDRs. Such changes would include, as example, changing the rotation around a Cα-Cβ bond (C=carbon), which for a valine put it in result in 3 different positions). For an arginine, there are up to 27 rotomers of the guanidium group. In the preferred mode, structural variations will be carried out early on. Considering mutational events, another level of variation could be rocking of the models. Further mutation (i.e., variation) would be changes in the angle between VH and VL from 0–15 degrees, which has the effect of shifting the target residues within the genes over a longer distance which can be considered shifting C α positions. These mutations will include 'catastrophic events' having global implications for the position of the amino acid within the CSR or CDRH3. These mutations enable local minima trapping to be avoided. Although the above mutational events are the first two preferred, the order of changes will be modified during the overall DIOGAM program.

Note that VH CDRH3 is a special case. This is so because first there are no canonical structures for CDRH3, second, it is by far the largest CDR region with insertion sizes of up to close to 24 amino acids; and third, because it can influence the angle between VH and VL. Therefore, this region is the one of most variations with the least structural restrictions.

According to the preferred mode of the invention, there are two positions within each CSR gene, which do not alter its canonical structure, and which are randomized in the rVab lib. as to amino acid. This translates to the possibility of any one of 20 amino acids being present at these two positions within each CSR and CDHR3 within any one of the Li members selected TSA+ rVab set under analysis. Therein, in the first level variation phase of DIOGAM, there is an arbitrary 'mutation', herein meaning rotation, of the gene allowing presentation of the various possible rotamers for these two particular amino acids found within one TSA+ rVab at each of the two randomized positions within the gene. Such mutation events will also be used later with VH CDRH3 at its two randomized amino acid position.

These mutants will then be analyzed by DIOGAM to derive other sets of $T_{1-n}$, in the manner described above.

Additional mutational events may also be utilized to produce further diversity to more fully describe the minimum structural requirements to define the common overlap (i.e., BEEP) which has the best TSA+ phenotype for the active site of the Target. Mutational events which effect fitness, will involve, but not be restricted to hydrophobic, electrostatic and conformational entropy effects, surface roughness, surface curvature, avoidance of unpaired charges, favorable and unfavorable steric interaction of functional groups and will be characterized by available programs like COGEN (Bruccoleri, R. E., and Karplus, M., 1987; Novotny, J., Bruccoleri, and R. E. Saul, F. A., 1989; and Tulip, W. R., et al. 1994) and the multiple copy simultaneous search method of CHARMM (Miranker, A., and Karplus, M., 1991; Patai, S. 1989 and Brooks, B. R., et al., 1993) using functionality descriptors with fewer atoms (Andrews, P. R., Craik, D. J., and Martin, J. L., 1984) or a spherical approximation to a multi-atom group (Goodford, P. J., 1985 and Goodsell, D. S., and Olson, A. J. 1990) based on time dependent Tartree approximation or minimization (Elber, R., and Karplus, M. 1990).

Once these mutational levels ($1^o$–$n^o$ level mutations) have been gone through one time, for each $L_i^o$, there will be new children (perhaps hundreds to thousands) of the original parental rVabs. Structural parameters of the second are then put through the 'Nussinov-Computer Vision' algorithm (Fisher, et. al. 1994), which is included herein by reference, to obtain the best alignment. Details of this method and some applications of the program (Fisher, D., et al., 1992 and Bachar, O. et al. 1993) are included herein by reference. The lowest values of the target functions for each Tn, will be different. The values will include, but not be restricted to, rms (for geometric overlap), $\Delta G$ (Gibbs free energy) and chemistry. The mutational events; will produce progeny which will be selected as having <rms, <energy and <negative chemistry values than those of the parental targets. Together the sum of these values define an overall Target Fitness Landscape for each Tn.

At this stage, DIOGAM will use commercially available algorithms, as described (see Goldberg 1990) by providers, and known to those skilled in the art, to score and register the results of each fitness test. At this stage then, there will be a list of ($\phi_i$, $\chi_i$, $\omega_i$, $x_i$, $y_i$, $z_i$ for each $L_i^n$ and a running fitness score ($Tij^n$). DIOGAM then goes back to next cycle of genetic variations, doing these iterations for thousands and thousands of generations, simultaneous, or in an ordered fashion, which at its termination will provide a list of best minima, which will be the 1st level BEEP, i.e., the best overlap of the surfaces contained within the set of active TSA+rVab.

We have done this manually in the case of two antibodies (NC10 and NC41) to the same site (epitope) on the surface of neuraminidase (Tulip, W. L., et al., 1994) and Malby, R. L., et al., 1994) which have been defined crystallographically and which provides us with a population, here only containing two members, which approximates the TSA+ rVab population isolated by this invention. Analysis of this population has shown overlap of antibody CSR and CDR surfaces which are bound to the same epitope. Therefore, a Sij surface as envisioned by this invention can be made.

At this stage, DIOGAM now goes back to the mutation stage and iterates, i.e., arbitrary changes rotamer position, overlapping the set, yet in so doing producing a slightly different set of $\phi_i$, $\chi_i$, $\omega_i$, $x_i$, $y_i$, $z_i$, but more importantly, finding Ts which are different (higher or lower) from its predecessors. Thus every character of every gene will be updated to reflect the fact that it incrementally (differently) contributed to a more robust phenotype (target fitness landscape).

DIOGAM directs the algorithm to enter into its next stage, initiated after many such mutational iterations, its crossover or recombination stage, wherein it creates new combinations of genes, even without knowing what is good (better fitness) about an existing gene mutations. These combinations, i.e., mating, of genotypes (or isogenotypes) are based on T scores, equal phenotype selection of better fitness, wherein fitness is defined as contributing to maximal overall overlap.

It is noted here that overlap is not restricted to physical occupation of identical space, but includes overlap defined, for example, as charge neutralization wherein, for example, two negative charged residues may be scored as 'overlapping' if they each could be within some distance of a positive charge.

In this entire process, it is important that the test tube selection of TSA+ rVab from the large rVab libraries, selects the right combination of genes which presently in no way can be guessed in advance. By definition, the combination existing in the active TSA+ rVab is 'correct' as it contains the surface necessary for desired activity profile, i.e., consisting of one or more of the desired attributes of affinity, selectivity and or activity on the target.

To summarize, in our genetic algorithm, DIOGAM, the gene is the object, the mutation is the change and the early selection is the testing by iteration to get a better number of individual genes. This is then followed by crossover using genetic logic of pieces of genes which are responsible for the fitness. This crossing over and recombination in the preferred instance includes deletions and additions of single amino acids or groups (referred to a seed clustering, or extension or simplification). With regard to additions, this includes those amino acids within the CSRs, CDR and framework domains of the rVab which have not been randomized, and includes those within the CSRs which are critical to the canonical loop structure itself. The importance of deletions and additions to genes as later mutational events is important as published data (Malby et al. 1994) shows that for two antibodies binding to the same antigen epitope, one of the CSR in the pair does not make contact with the target surface and that large target recognition domains may themselves contain much smaller domains which are responsible for the most of the energy of target interaction (Clackson and Wells, 1995). For the purpose of this invention, the Ti of the best common overlap, i.e., the BEEP, is related to the existence of a small subset of high energy density points in the atoms target surface (Clackson, T. and Wells, J. A. 1995; and Tulip, W. R., et al., 1994), which is considerable less than all contact residues. This is expected to simplify the alignment (i.e., overlapping) of the $L_i$ for example if the target domain which is responsible for the TSA+ phenotype of the set selected rVabs is assumed to have just two hot spots then there is a very restricted number of ways a given antibody, known to interact with the site so as to have a TSA+ phenotype, can bind to that site.

D. Identify small organic molecules active at target sites

1. Use of BEEP as High Volume Screening Reagent

The BEEP provided by this invention may be used as follows to identify SOMERS or drug leads.

a. Use BEEP to electronically screen CHEMFILE to identify SOMERS as discovery leads using computer structural programs commercially available and known to those skilled the art.

b. Use the coordinates of the BEEP to screen via existing computer technology entire chemical data bases for matching SOMERS.

c. Select a few SOMERS and test in vitro and in vivo to confirm discovery lead.

d. Use BEEP to direct synthesis of active SOMERS via techniques known to those skilled in the art of medicinal synthetic chemistry.

2. Identification of SOMERS using rVAB-Reporters a. Select: 1–2 representatives of each surface domain group within the active-selective rVabTSA$^+$ library and enzymatically label with, for example a radionuclide.

b. Establish competition binding assays using endogenous ligand and known allosteric target regulators as displacer labelled rVabTSA reporter.

c. Screen chemical libraries via standard automated binding assays for SOMERs which displace labelled rVab from its target. Identify all close analogs of active SOMERS and perform SAR for target binding.

3. In a preferred embodiment, DISOMERS are identified as follows (See FIGS. 21 and 22):

a. Start with all rVab which recognize a surface on pharmacological targets. These can be selected following steps described above.

b. Modify the phage rVab, rVvx library to contain one or two large random peptide libraries sufficient to occupy the other one or two TARGATTS which together make up the active surface of the target. After identifying a scanner rVab to identify one TARGATT identification of the others is accomplished which may also be done in the presence of the first discovered SOMER. Do limited SAR on each SOMER to identify the inactive elements, covalently oligomerize the two or three SOMERS via linkage through their inactive surfaces to make a DISOMER or TRISOMER. Test in vivo and in vitro to identify best Discovery Lead.

c. Test most potent SOMERs for activity using an in vitro target assay.

d. Test in vitro active SOMERS with best CAP in vivo (via I.P. route to identify Discovery Leads.

If no analogs exists of originally discovered SOMERS, carry out limited synthetic effort, use A*rVabs or rVvx to do a limited SAR binding study and then select best and test in vitro and in vivo for entire CAP.

If label reporter A*rVab or rVvx for a particular target domain does not uncover SOMERS or none are displayed by endogenous ligand, perform secondary simplication or diversification of CSRs and CDRs, reselect for the TSA$^+$ and carry out 3A again.

Screening for small organic molecular replacements (SOMERS) will be done by methods known to those skilled in the art using robotic assay employing labelled n[*]rVab with specific CAP and searching for compounds which displace [*]rVabT$^+$ binding to targets.

e. Excise all rVHCH domains from rVHCHT$^+$.LIB, move into the plasmid for bacterial periplasmic expression and create a library of soluble VHCHT$^+$. Mix this library of soluble rVHCHT$^+$ entities and a phage library of rVLCL displayed attached to the phage coat protein through its CL region (rVLCL.LIB) to make a combinatorial library wherein only one member is packaged in the isolated phage and pan against target protein as in 2Aa. After enrichment (2–4 cycles of selection for one or more of the three desired properties) the genes for the active rVLCL entities are obtained. The genes for the active rVHCHT$^+$ entities may then be obtained in a manner similar to that used to obtain the rVLVL genes. After exision of both the rVLCH and rVHCH genes, the Cre-Lox recombination system (see below) may be used to construct a single phage containing both chains and for expression of the rVab.LIB as a phage displayed functional complex. In another embodiment, the libraries may expressed as single chain versions with VH and VL coupled through a linker using commercially available kits, such as those from Cambridge according to the manufacturer. Finally, enrichment and selection of VH:VL combinations which possess the desired target attribute s may be obtained by, for example, panning.

EXAMPLE 1

Construction of a Recombinant Surface Scanner rVab Library (rVab.lib).

VII. Selection of Parental Fabs of Known Crystalline Structure as rVab Library Framework Templates The amino acid sequences and crystalline structure of the light and heavy chains of the antibody ABXXX which is used as the parental Fab for construction of the rVab.library are obtained from the Brookhaven Data Base, the Kabat Data Base, GENEBANK (email: NCBI.NIH.GOV.) or Kabat, E. A., et. al. (Kabat, T. T. Wu et al. 1991). The V regions of the light and heavy chains are subdivided in domains as follows: the highly variable complementary determining regions (CDR), the canonical structure region (CSR) within each CDR, and the intervening framework regions (FWR) (FIG. 2.5.6). Individual amino acids not within a CSR or CDR, but nevertheless essential to the canonical structure (Chothia and Lesk 1987; Chothia, Lesk et al. 1989; Kabat, T. T. Wu et al. 1991; Chothia, Lesk et al. 1992) are also listed (FIGS. 5, 6)

ABxxx is selected as the parental framework template for the construction of the ABxxx rVab.lib for recognition of target surfaces by an antibody with a planer type antigen combining site. This selection is based on the following: 1) availability of the crystal structure of the antibody (bound or free of corresponding binding partner, i.e. antigen); 2) the antibody is a member of the planer type combining site group of Fabs (Webster, Henry et al. 1994) which have been found to recognize protein surfaces; 3) the antibody has canonical structures for CSR H1-2 and L1-3; 4) the antibody's CDRH3 size is in the mid-range of sizes of CRDH3 (so as to favor equal usage of all 6 CDRs of the rVab in target recognition (Wu, Johnson et al. 1993); and 5) the antibody's antigen is a protein (FIG. 3). Parental antibody frameworks found in antibodies with a cavity and a grove group type combining site (classification as reviewed by Webster [Webster, Henry et al. 1994]) will also be used to make two additional rVab libraries in a fashion similar to that described below for the rVab.lib based on ABXXX. Together these three libraries generate a sufficiently large number of probes for surface recognition of relevant binding sites.

In the ABxxx: rVab.lib the natural diversification of antibodies is provided by placing within the library varied combinations of VH and VL domains which themselves have varied combinations of the known canonical CSRs, variable length CDRH3s, and randomized amino acids (one of 20 essential amino acids) at one or more amino acid positions within the CSR or CDRs of each V region within each rVab (FIG. 4).

VIII. Creating the Nucleic Acids Encoding the Heavy and Light Chains (rVHCH1 and rVLCL) for ABXXX rVab.lib.

The nucleotide sequence of ABxxx is obtained from Sequences of Proteins of Immunological Interest, 5th ed. (Kabat, E. A., T. T. Wu et al. 1991); the Kabat Data Base (NCBI.NIH. GOV); or GENBANK. Identification and analysis of all restriction sites present within these sequences may be accomplished using a commercially available program (GCG [Univ. Wisconsin, USA], MacVector [IBI, Kodak, New Haven, Conn.], DNAStrider (C. Marck, Gif-Sur-Yvette Cedex, France, Service de Biochemie, Inst. Res. Fundamental, Aloric Energy Commission of France) and SeqEd, [Applied Biosystem]).

Restriction sites endogenous to ABxxx and conflicting with construction of the rVab.lib as outlined below are removed and replaced with other nucleotides not encoding the conflicting restriction site. This is done using sequences which keep unchanged the identity of the parental amino acid(s).

The sequences are then analyzed again for the changes necessary to place the convenient and unique restriction sites throughout the V and C genes needed for library construction as outlined below.

The ABXXX rVab.lib is built according to this invention from separate rVLCL (FIG. 7) and rVHCH1 (FIG. 8) chains which are combined randomly in an in vivo process (FIG. 14). The construction of the rVLCL and rVHCH nucleic acid libraries encoding the rVLCL and rVHCH1 chains, is accomplished in steps outlined as follows: step 1) oligonucleotide synthesis: construction of a) amino terminus end (5'V), b) a midregion (MIDV) for VL only, and c) a carboxy-terminus end (3'V) of the V region; step 2) diversification via PCR of some CSRs; step 3) ligation of the sections; step 4) diversification of the remaining CSRs; and step 5) ligation of the appropriate constant (CH1 or CL) region derived by PCR or oligonucleotide construction to generate the complete recombinant heavy and light chain libraries (rVHCH1. lib and rVLCL.lib).

Figure 7E:
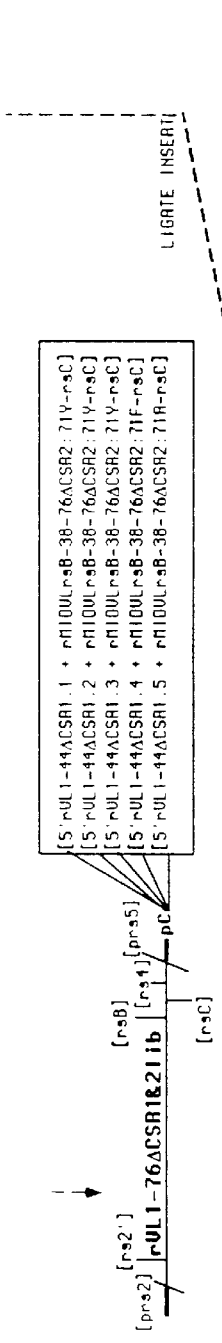
Figure 7F:
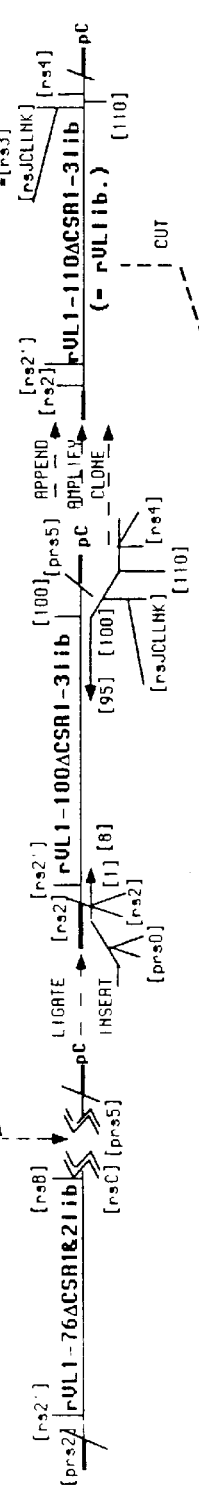
Figure 7G:
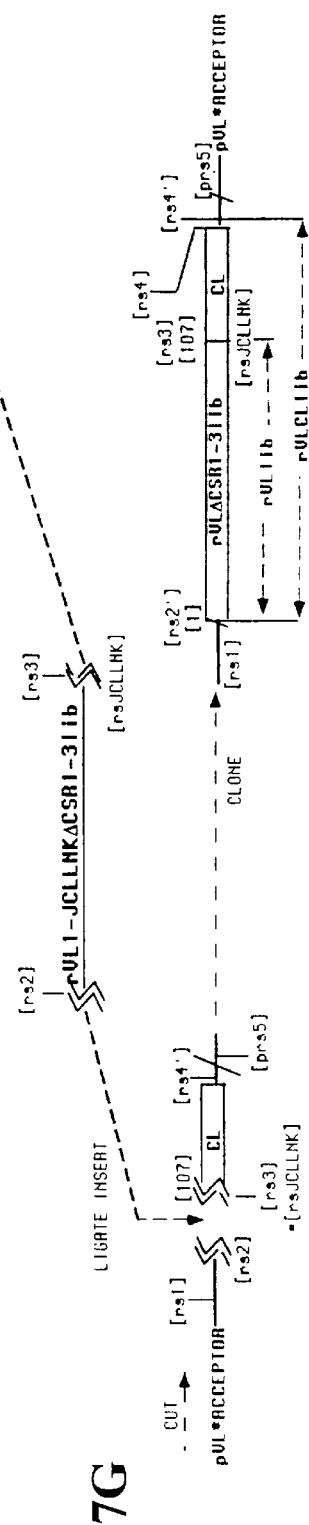
Figures 8A, 8B, 8C, 8D, 8E:
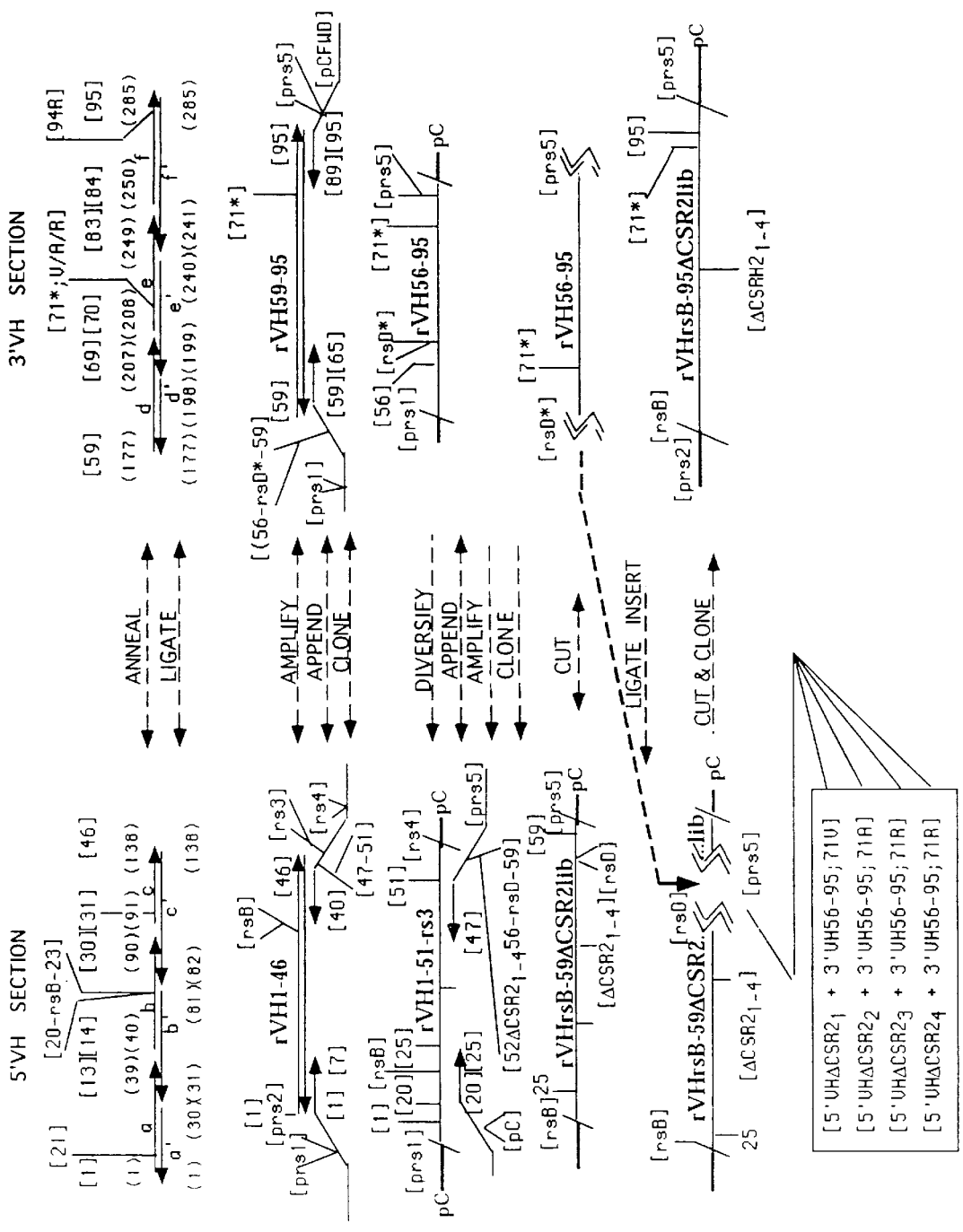
Figure 8F:
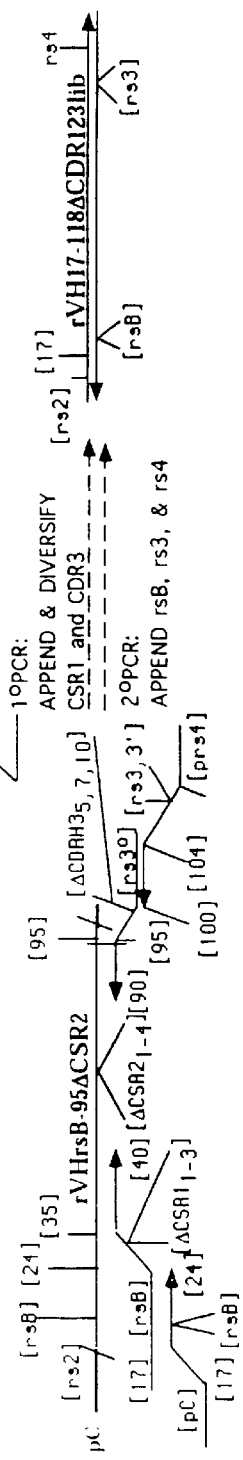
Figure 8G:
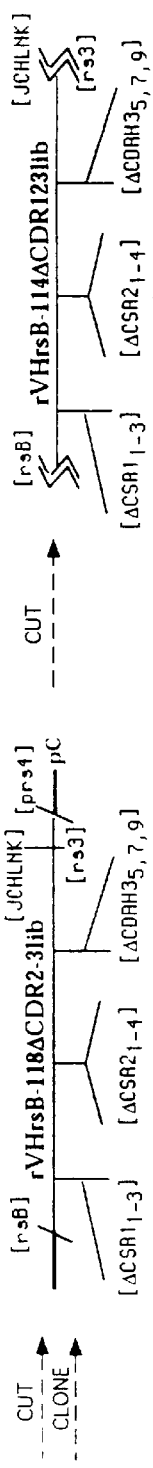
Figure 8H:
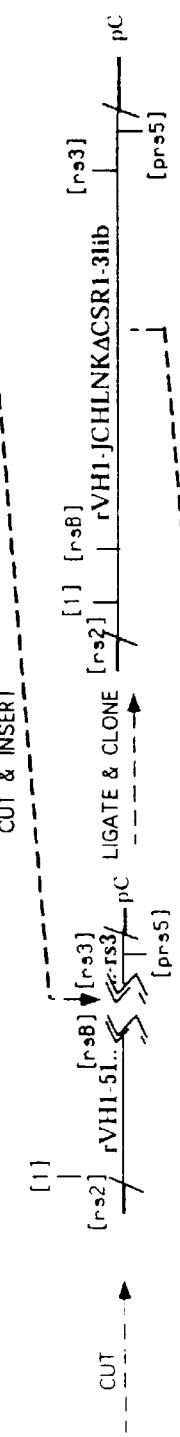
Figure 8I:

Step 1: Construction of rVLCL.lib (FIG. 7)

In the olignucleotide phase (step A, FIG. 7), construction of a) the 5' (5'VL) end; b) the Mid section (MIDVL) end c) 3' (3'VL) end of the VL region uses eight synthetic oligonucleotides comprising four complementary pairs. Each oligonucleotide (x) has a complementary mate labelled x'. Two oligonucleotide pairs, a/a' and b/b' are used to make the 5' end. The MIDVL (c/c'), and the 3'VL (d/d') sections are each synthesized from one oligonucleotide pair. The amino acid and nucleic acid positions encoded by the specific oligonucleotides are shown in FIG. 7.

The variance in amino acids at position 2 (within a/a') and 71 (appended to c/c') necessary to allow for construction of all the desired VL1 CSRs is added during later steps as described below. All oligonucleotides are synthesized so as to have at least one overlapping complementary sticky end, an absence of hairpin forming ends, and to be noncomplementary to sequences other than that of the desired oligonucleotide joining partner based on analysis by a commercially available oligonucleotide primer analysis software program.

Step 1(a): Construction of 5'VL Section

For construction of the 5'VL end section in step 1(a), the oligonucleotides are first phosphorylated, then mixed together in one reaction mixture, heated, annealed and ligated together using generally known molecular biology technology (Sambrook, Fritsch et al. 1990). The product is then isolated and ligated in 60 µl reactions with 1200U T4DNA ligase (New England BioLabs) to 5 µg pCLONALL (see FIG. 9 which lists all general use plasmids) digested at restriction site (rs) prs0 and rs4 ("p" signifies that the location of the restriction site is within the plasmid and outside of the rVab sequence) (Sambrook, Fritsch et al. 1990).

DNA is purified from the ligation mixture using Gleneclean II (Bio101), resuspended in water and used for transfection by electroporation (Dower, Miller et al. 1988) of *E. coli* TG1 (Gibson 1984) grown in broth containing 1% glucose for 1h and then plated on dishes in antibiotic containing media. After overnight (o.n.) incubation at 37° C., individual colonies are picked. Colonies are identified as rVL3-24.bact first by diagnostic PCR using primers pCFWD and pCBCK (see Primer Table, FIG. 10) and subsequently confirmed by sequence analysis via automated an ABI sequencer and commercially available related kits as outlined by manufacturer (ABI,USA). Storage of positive clones at −70° C. is done in broth (Miller, 1972) containing 15% (v/v) glycerol.

Step 2: Diversification by PCR

Toothpicked frozen glycerol stocks of rVL3-24 are used in PCR reactions to append primers conferring diversification to the rVL section. One of the five different CSRL1 diversified with random amino acids at two positions is used as the FWD primer at the 3' end of the parental ab/a'b' 5'VL section. The BCK primer for the 5' end comprises nucleic acids encoding one of the three different amino acids I, V or S at position VL2, and the amino acid of the parental ABXXX at position VL1. These appendings are done in 5 primary PCR reactions, each containing one FWD primer (i.e., L1.1FWD, L1.2FWD, L1.3FWD, L1.4FWD) or L1.5FWD) and one of three different BCK primers in the following combinations: L1.1–3BCK primer mixed with the 3 reactions containing L1.1, L.12 and L.13 FWD primers, and L1.4BCk and L1.5BCk mixed correspondingly with one of the two remaining L1-FWD primers. Subsequently, amino acids VL34–44 are appended to the primary PCR products in secondary PCR reactions by taking an aliquot of the primary reaction and carrying out secondary PCR with primers L1ALLFWD and L1ALLBCK. The products of the secondary reactions are kept separate and are labelled rVL1-44CSR1.1–5.lib.pcr. These constructs allow subsequent generation of all 5 known canonical CSR L1 in the rVL.lib after cloning when these products are joined with the appropriate MIDVL section having one of three different amino acids in position VL71. Each of the primary PCR uses Taq polymerase, FWD and BCK primers as noted above, in 50 µl reaction mixtures and is cycled 25 times (94° C. for 1 min, 60° C. for 1 min and 72° C. for 1 min). The secondary PCR reactions (25 µl) use fresh Taq polymerase and 1 µl of amplified appended diversified primary PCR reaction mixture product, FWD and BCK primer pairs as noted, and the reaction is cycled 30 times (94° C. for 1 min, 55° C. for 1 min and 72° C. for 2 min). A list of the sequences of all primers appears in Primer Table (FIG. 10).

In step C, the five products of the secondary amplification reaction of correct size, are designated rVL1-44CSR1.1–5, and are isolated on low percentage acrylamide gels, recovered, restricted and ligated to pCLONALL precut with prs4 and rs2 and cloned via electroporation (Dower, Miller et al. 1988) into *E. coli* as described (step B, FIG. 7). These five 5'VL section products are designated rVL1-44CSR1.1–5.lib.bact. Twenty clones of each library are checked first by diagnostic PCR and subsequently five (5) clones are analyzed for diversification of CSR1 by automated sequencing as described above using pCFWD and pCBCK sequencing primers and commercially available kits (ABI,USA). This procedure generates greater than $10^4$ transformants per each of the five VL1 CSRs.

Step 1(b): Construction of the MIDVL Section

In parallel fashion, a second set of reaction steps A–C constructs the MIDVL section of rVLlib. The MIDVL section originally contains amino acids rVL53–68. The oligonucleotides for this reaction are contained in the one pair c/c'.

In step A, each oligonucleotide is phosphorylated, the pair hybridized together under annealing conditions, and the c/c' double stranded DNA complex is purified and ligated in a 60 µl volume with 1200U of T4DNA ligase (New England BioLab) to approximately 5 µg rs2 and prs5 cut pCLONALL (Sambrook, Fritsch et al. 1990). Ligated product is isolated from the mixture using Genecleanb II (Bio101), resuspended in water and used to transform E. coli via electroporation (Dower, Miller et al. 1988). After 1 hr in broth containing 1% glucose, the cells are placed on dishes in antibiotic containing media. After overnight incubation at 37° C., individual colonies are picked and the MIDVL section transformants are identified from among 30 transformants generated by diagnostic PCR. Confirmation of sequences is by automated sequencing using an ABI automated sequencer using pCFWD and pCBCK primers (ABI, USA). Positives are labelled rVL53-68.bact. and frozen glycerol stocks are produced.

In step B diversification, PCR is used to append diversified CSRL2 to the 5' end of MIDVL. Three different amino acids at VL71 (i.e., Y, F and A) followed by restriction site rsC between VL72 and VL76 followed by a rs4 restriction site are appended with primers to the 3' end of MIDVL. These additions are done in three separate reaction mixtures, one each containing FWD primer L2.71YFWD, L2.71FWD and L2.71FWD. All three FWD primers contain the rsC site which will allow joining of MIDVL to 5'VL sections. For each of these reactions, the BCK primer is L2ALLBCK which contains an rsB site as well as DCSRL2 diversified at amino acid VL50 and 51. Each mixture contains a toothpicked frozed glycerol stock of rVL53-68 (see Primer Table, FIG. 10 ), Taq polymerase, in 50 µl mixtures, and is cycled 25 times (94° C. 1 min, 60° C. 1 min 72° C. 2 min).

In the following step C, approximately 1 µg of the amplified diversified appended MIDVL products are isolated using Magic PCR Preps (Promega), cut with prs1 and rs4, reisolated and ligated to 5 µg pCLONALL precut with prs1 and rs4 in 60 µl volume with 1200U T4DNA ligase (New England Biolabs) (Sambrook, Fritsch et al. 1990). The ligated plasmid DNA products are isolated using Geneclean II (Bio101), resuspended in water and used to electroporate E. coli to generate, as noted above, a library of transformants (Dower, Miller et al. 1988). The three separate groups of successful transformants (one for each type of VL71) are identified by diagnostic PCR and confirmed regarding diversification of VLCSR2 by automated sequencing of 10 clones of each group. These transformants are designated rVL 38-73CSR2:71 (Y,F,A) lib.bact. This procedure gives $\geq 10^4$ transformations for each group.

Step 1(c): Construction of the 3'VL Section of rVL

In the third set of parallel steps A–C, the 3'VL section of rVL.lib is constructed. This section is originally built to contain amino acids VL72–90 and uses the one oligonucleotides pair d/d'. In step A, this pair is phosphorylated and the two oligonucleotides annealed. The double stranded complex is then isolated and is ligated to pCLONALL precut with prs0 and rs4'. Ligated product is isolated and used to transform E. coli via electroporation (Dower, Miller et al. 1988) as above. 3'VL section transformants are isolated from among the transformants generated, and diagnostic PCR is preformed on twenty of them, the positives being confirmed by automated sequencing and labelled rVL76-90.bact. Frozen glycerol stocks are prepared.

In the next phase, diversification (step B), the six diversified CSRL3s, followed by a new prs5 site, as well as amino acids VL72–75 which contain the convenient restriction site (rsC), are appended to VL76–90 to make the following 5'VL PCR product: rVL72-100CSR3.1–6.pcr. Diversification of CSR3.1–6 occurs at positions VL92 and 93. These processes are done in six (6) separate 50 µl PCR reactions each containing one L3.1–6FWD primer, all containing L3ALLBCK (see Primer Table, FIG. 10), and Taq polymerase in 50 µl mixtures. The reactions are cycled 25 times (94° C. 1 min, 60° C. 1 min and 72° C. 2 min).

In step C, the amplified diversified appended products are isolated using Magic PCR Preps (Promega), cut with prs2 and rs5, reisolated and ligated into pCLONALL precut with prs1 and prs5. The ligated plasmid DNA products are isolated and used to electroporate E. coli to generate a library of transformants as noted above and designated rVL72-100CSR3.1–6.lib.bact. This procedure gives greater than $10^4$ transformations which are identified by diagnostic PCR and sequencing to contain appropriately randomized amino acids at the diversified positions within VLCD3 for each of the six (6) VLCSR3s.

Step 3: Ligation

In step 3, the 5'VL and MIDVL sections are joined (see FIG. 7). Five µg of DNA of each of the five rVL1-44.libs (i.e., CSR1.1–5) is digested with rsB and rs5 and ligated to 1 µg of insert isolated from the three rVL38-70CDRL2:71* using 1200U T4DNA ligase ((New England BioLabs) (Sambrook, Fritsch et al. 1990). In these reactions, ligation pairing of 5'VL[rVL1-44CSRs] to MIDVL[rVL38-76CSR2:71*] is maintained as: 5'VL1.1–3×MIDVL2:71Y; 5'VL1.4×MIDVL2:71F and 5'VL1.5×MIDVL2:71A to create the five rVL1-76CSRD1&2.DNAs. Each of these is used to electroporate E. coli (Dower, Miller et al. 1988).

The bacteria are then grown in broth containing 1% glucose for 1 h and are plated on dishes in antibiotic containing media, After overnight incubation at 37° C., individual colonies are picked and are characterized first by diagnostic PCR and then by automated sequencing. Some 100 colonies are analyzed by diagnostic PCR and 20–30 by sequencing to confirm the random presence of different CSR pairing and diversified amino acids within the various CSRs. Frozen stocks of the five groups are then prepared and are designated rVL1-76CSR12.lib.bact.

In step F, the extended 5'VL halves, consisting of the five rVL1-76CSR1&2.libs., are joined in 30 separate PCR reactions in combinatorial fashion with the six 3'VL halve sections, consisting of the six (6) rVL72-100CSR3.1–6.lib. This process generates 30 full length rVL1-100CSR1&2&3.lib. (as diagramed in FIG. 7). In each of these library constructions, about 5 µg of DNA of each of the five rVL1-71CSR1&2.libs (i.e., CSR1.1–5) is digested with rsC and prs5 and ligated to 1 µg of each of the inserts isolated from the six rVL72-100CSR3.1–6 digested with rsC and prs5 using 1200U T4DNA ligase (New England BioLabs) (Sambrook, Fritsch et al. 1990) to create the 30 rVL1-100CSRD1&2&3.dna preparations. Equal aliqouts from each ligation mixture are pooled and the pooled DNA is purified using Geneclean II (Bio101) and resuspended in 30 µl water to create the completed rVLCL.lib.dna. PCR is then used to append to the 3' end of this DNA library, the nucleotides encoding the remaining amino acids of VL (i.e. rVL101–107), amino acids at the 5' end of CL (i.e., amino acids CL108–110), and within this sequence the convenient rs3 site. The rs3 site, also designated the rsCLLNK site (FIG. 9), subsequently allows the joining of rVL.lib with its cloned rCL section.

These appending reactions are done by carrying out a PCR reaction with an aliquot of the purified rVL1-100CSR1&2&3.lib.dna, the primers LJCLLNKFWK and L1ALLBCK, and the Taq polymerase in 50 µl volume mixtures cycles. The PCR reaction is cycled 25 times (94° C. for 1 min, 60° C. 1 min and 72° C. for 2 min).

Amplified DNA is then purified using Magic PCR Preps (Promega). After suspension in water, 1 µl g of the purified DNA is digested with rs2 and prs5 and ligated to 5 µg of pCLONALL DNA precut with rs2 and prs5 using 1200U T4 ligase (Sambrook, Fritsch et al. 1990) and used to electroporate *E. coli* (Dower, Miller et al. 1988). The bacteria grown in broth containing 1% glucose for 1 h are then plated on dishes in antibiotic containing media. After overnight incubation at 37° C., individual colonies are picked and characterized first by diagnostic PCR and then by automated sequencing. Some 100 colonies are examined by diagnostic PCR and some (about 5–10) by sequencing to confirm the presence of amino acids VL1–110 and the random presence of different CSR pairings and diversification of amino acids within the various CSRs. More than $10^8$ transformants are generated in this process and a frozen stock of the library is then prepared and designated rVL.lib.bact.

In the last step (step G) of rVL.lib construction, DNA from rVLlib is digested with rs2 and rsJCLNK, and 1 µg is ligated to 5 µl g of pVLACCEPTOR (FIG. 9), precut with rs2 and rsJCLLNK, using 1200U T4 ligase (Sambrook, Fritsch et al. 1990). The product is then purified from the ligation mixture using Gleneclean II (Bio101) and resuspended in water. This material is used to electroporate *E. coli* (Dower, Miller et al. 1988), and the bacteria are grown, after1 hr in broth supplemented with 1% glucose, overnight at 37° C. on dishes in antibiotic containing media. Individual colonies are picked and characterized by diagnostic PCR and automated sequencing to confirm the presence of CL in the library. Frozen glycerol stocks of rVL1-110ΔCSR1–3lib are made and designated rVLCL.lib.bact (FIG. 7).

The above detailed reactions where double amino acid randomization occurs within each CSR theoretically allows the construction of 2000, 400 and 2400 different CSR L1,2,3 respectively, and a rVLlib size of $1.92 \times 10^9$. This exceeds the largest published recombinant VL library made by similar (Griffiths, Williams et. al. 1994) technology by about 2 fold.

IX. Construction of the Constant Regions of ABxxx

Figure 9A:
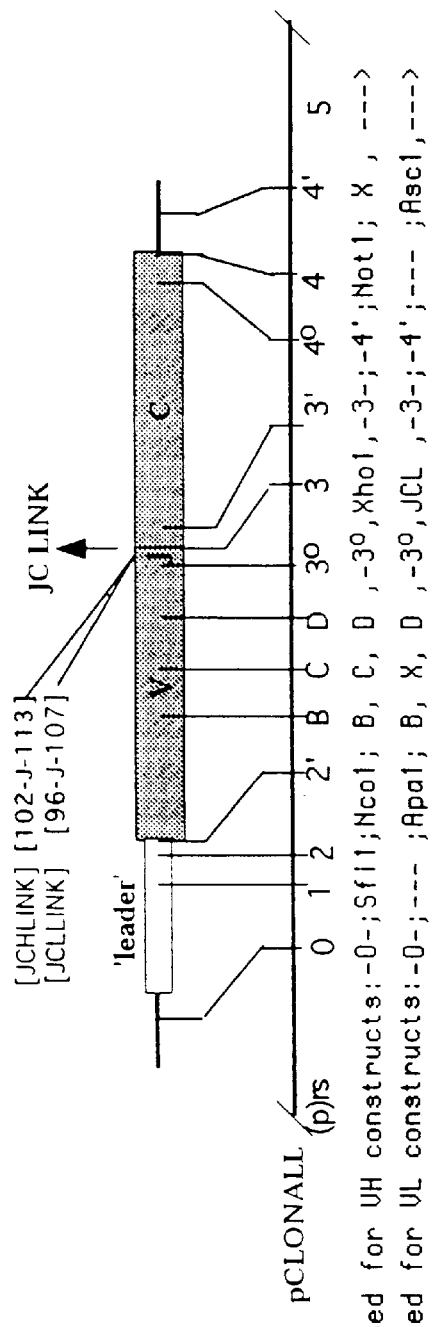
Figure 9B:
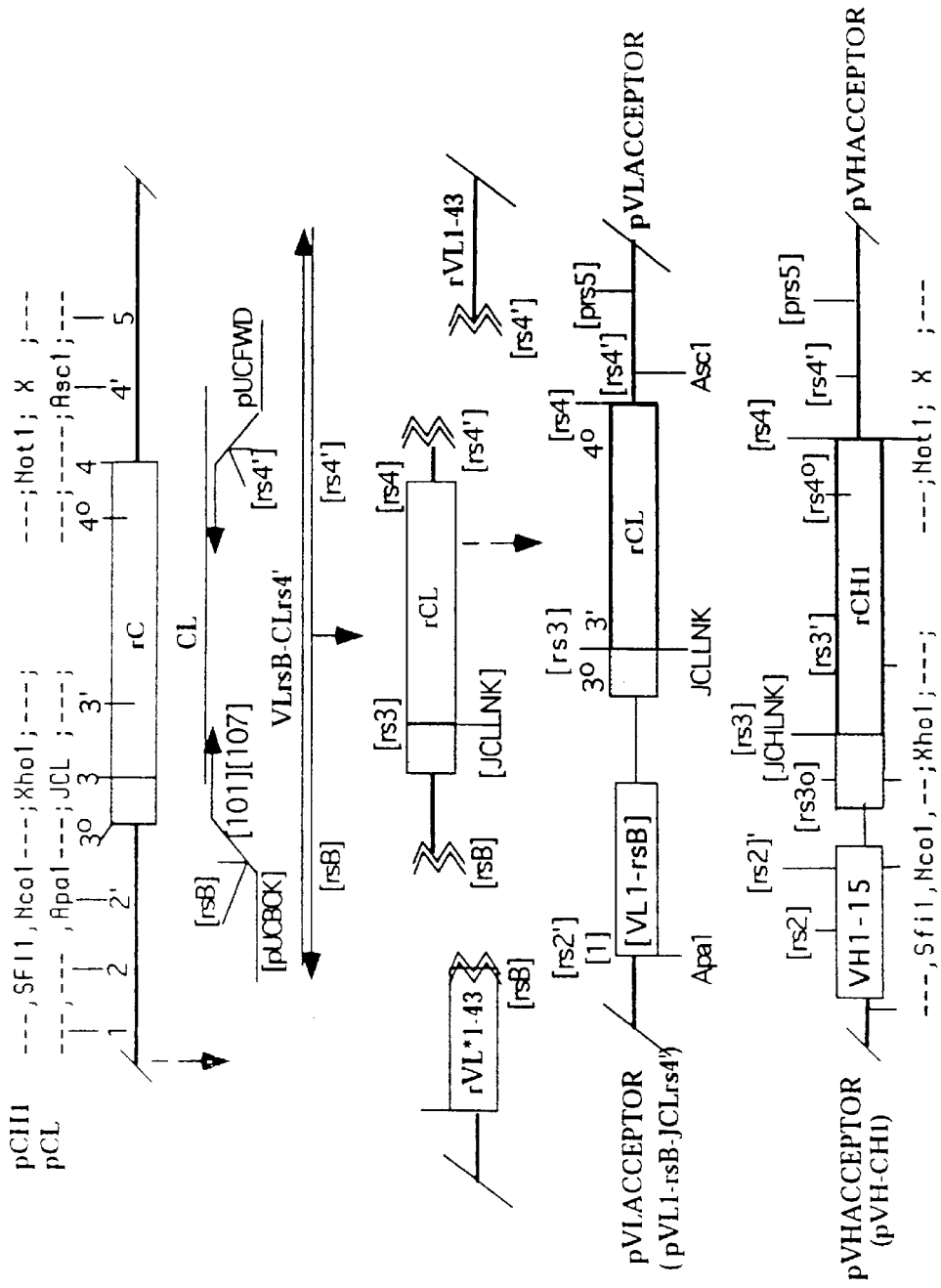
Figure 9C:
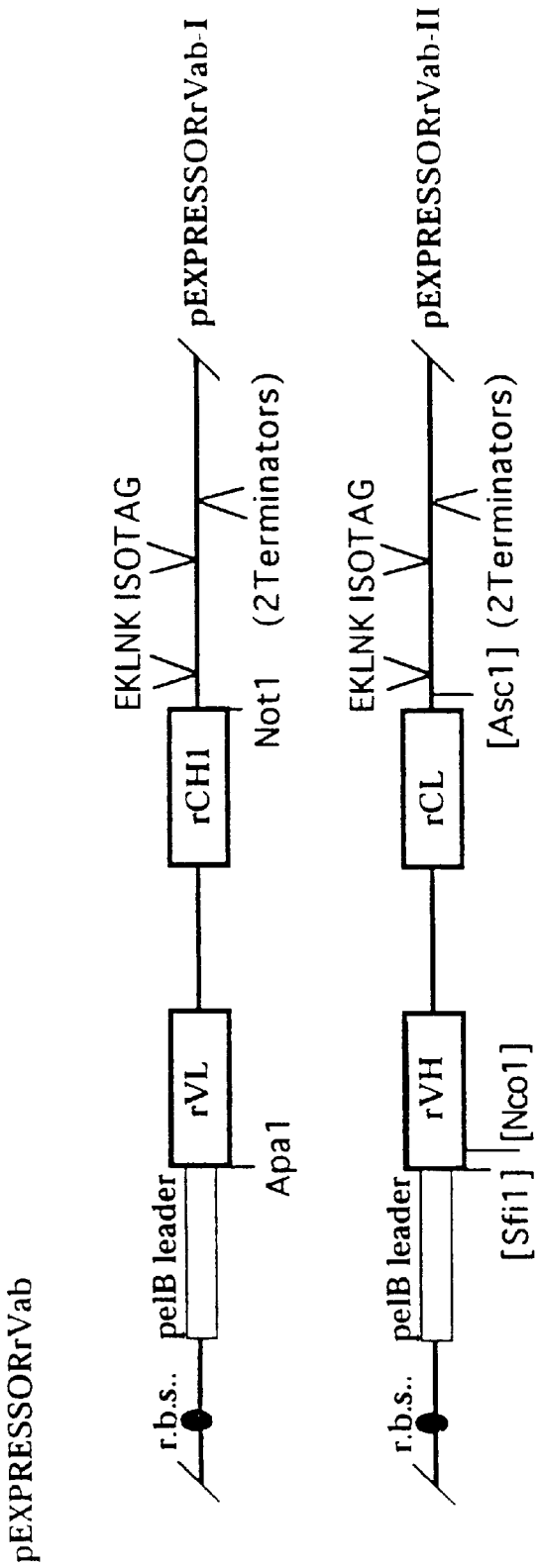

The constant region (C) of the light (CL) and heavy chain (CH1) region for the selected parental Fab ABxxx (FIG. 9) is obtained either by annealing and ligating a series of synthetic overlapping oligonucleotides, as done for the V regions, or via standard PCR of the C regions of ABxxx or any other antibody mRNA or DNA with identical C regions. Nucleic acids encoding specific antibodies may be obtained from hybridmas from various sources including the ATCC. In either case, the constructions includes the removal of endogenous restriction sites that interfere with library construction and the creation of a number of convenient restriction sites at and around the 5' and 3' ends of the C regions so as to allow simple cloning into pCLONAL, pEXPRESSION and pV(H or L)ACCEPTOR (FIG. 9). For both CH1 and CL regions, the C genes have inserted within them an rs3 site for specific joining of V and C sections of rVL at or about the natural V/J gene junction for heavy and light chains. These sites are referred to as either rsJCHLNK and rsJCLLNK respectively. In constructing the C sections, these two junctional rs are appended by standard PCR using BCK primers CLBCK and CHBCK and FWD primers CLFWD and CHFWD (see Primer Table for sequence details (FIG. 10).

The parental C nucleic acid sequence of ABXXX is amplified by PCR with Taq polymerase using primers CLFWD and CLBCK which places the rs3 restriction site within the JC segment of the parental Fab at the 5' end of the C sequence and two stop codons (TAA) and the rs4' site (AscI) just outside the 3'-end of the C region. The reaction mixture (50 µl) is cycled 25 times (94° C. for 1 min, 60° C. for 1 min, and 72° C. for 1 min.) and the amplified appended C sequence is purified using Magic PCR Preps (Promega) and resuspended in 50 µl water.

The reaction amplifying the parental Fab CH1 gene of ABXXX is identical, except for the following: the primers for the PCR reaction are different, being CHFWD and JCHBCK, and the CHFWD primer contains a Not1 site at the 3' terminus of the CH1 region.

To complete construction of the VLCL, the amplified and J appended recombinant VL diversified CSR1 and 2 and 3 (rVLCSR1&2&3) genes are joined to the amplified CL gene in the standard ligation fashion used above, or using PCR (Horton, Hunt et al. 1989). Assembly PCR reactions (25 µl) use Taq polymerase, 1 µl amplified parental JC, and 0.8 µl of the rVL.lib gene from above. The appropriate VLBCK primer is used together with the CLFWD and the reaction cycled 30 times (94° C. for 1 min, 60° C. for 1 min. and 72° C. for 2 min.).

X. CONSTRUCTION OF rVHCH1.lib (FIG. 8)

In the oligonucleotide phase (step A), construction of a 5' and 3' half of the VH region is accomplished using 16 synthetic oligonucleotides, comprising 8 complementary pairs. Six oligonucleotides are for the 5' half and are labelled VH a–c with their complementary partners labelled VH a'–c'. Within the 5'VH half, the oligonucleotide b/b' pair has the rsB restriction site between amino acids rVH 22–26. Ten oligonucleotides are for the 3' half and are labelled VH d–f and d'–f'. Construction of the 3' half of the VH region is done in a similar fashion but uses three forms of the "e" complementary pair, designated as follows VH e/e', VH e2/e2' and VH e3/e3'. These correspond to the "e" oligonucleotides with either a valine (V), alanine (A) or arginine (R) at amino acid position VH71, respectively.

In the annealing step, three types of the 3'VH half are constructed: 3'VHdef/d'e'f', 3'VHde2f/d'e2'f' and 3'VHde3f/d'e3'f. The variance in "e" oligonucleotides within the 3'VH half is necessary to allow for subsequent construction in the rVHlib of all four of the known CSRH2 as outlined below. All oligonucleotides are synthesized so as to have a least one overlapping complementary sticky end, an absence of hairpin forming ends, and an absence of complementary sequences other than those of the desired oligonucleotide joining partner based on analysis by a commercially available oligonucleotide primer analysis software.

Construction of 5' half of the VH Region

For constructing the 5' half of the VH region, the appropriate oligonucleotides are phosphorylated and are mixed together in one reaction mixture, after which they are heated and are annealed and ligated together using generally known molecular biology technology (Sambrook, Fritsch et al. 1990). As outlined, the first phase annealing and ligation (step A, FIG. 8) allows the formation of the 5' VH abc/a'b'c' pair. In the next step (step B), the correct construct of 5' VH, containing a convenient rsB within its b/b' segment, is amplified with primers 5'VHFWD and 5'VHBCK (a list of names and sequences for primers used in VHCH1.lib construction appears in the Primer Table, FIG. 10) by carrying out PCR on an aliquot of the ligated and isolated abc DNA duplex product of step A. In this step, an aliquot from the step A reaction is amplified using the above noted primers and Taq polymerase in 50 µl reactions; and is cycled 25 times (94° C. 1 min, 60° C. for 1 min, 72° C. for 2 min.). The amplified DNA is purified using Magic PCR Preps (Promega) and is suspended in 5 µl water.

Next, the product of the amplification reaction having the correct size and designated rVH1-51, is cut at rs4 (Not1) and prs1. The cut fragment is purified by Magic PCR Preps (Promega) and 1 µg is ligated in a 60 µl volume with 1200U of T4 DNA ligase (New England BioLabs) to 5 µg of rs4 and prs1 digested pCLONALL (Sambrook, Fritsch et al. 1990).

DNA is purified from the ligation mixture using Geneclean II (Bio101) resuspended in 30 μl water and electroporated (Dower, Miller et al. 1988) into *E. coli* which is then grown in broth containing 1% glucose for 1 h and plated into antibiotic containing media. After overnight incubation at 37° C., individual colonies are picked and identified. Transformants containing the recombinant parental 5'VH half, rVH1-51, are identified by diagnostic PCR for appropriate size (with plasmid primers pCFWD and pCBCK). Those transformants suspected of containing the rVH1-51 are expanded. The nucleic acid amplified with PCR using PCFWD and pCBCK are sequenced via automated ABI sequencing with commercially available kits as outlined by the manufacturer (ABI,USA) to confirm the identity of the rVH1-51 fragment. Cultures are then grown and stored as frozen glycerol (15% v/v) stocks and designated rVH1-51bact.

In the next step, step C (FIG. 8), a diversified version of each of the four known CSRH2 is appended to rVH1-51. This process is done in four separate standard PCR reaction mixtures (see above). Each reaction mixture comprises the rVH1-51 fragment (obtained from toothpicked frozen glycerol bacterial stocks), one of four FWD primers (H2.1FWD, H2.2FWD, H2.3FWD and H2.4FWD) and the BCK primer H2ALLBCK. The four FWD primers are constructed to span from amino acid 47 through 59 of $CSR2_{1-4}$ and contain amino acid diversification at position 53. The four library products, are isolated, and are cut at rsB and prs5, and then 1 μg of each purified DNA product is ligated using T4DNA ligase to 5 μg pCLONALL precut at rsB and prs5.

As described above, the ligated DNA is purified and used in step D to transform *E. coli* via electroporation. Transformants are isolated and characterized first by diagnostic PCR and then by automated sequencing to contain appropriate examples of the randomized diversified versions of all four CSRH1. Frozen stocks of each, designated rVHrsB-59CSR2.1–4 lib. bact. are made.

Construction of the 3' Half of the VH Region

In a parallel fashion, another set of reaction steps A–C are conducted to construct the 3' half of the VH region which incorporates nucleic acid encoding amino acids 57–95 of the variable heavy (VH) chain (FIG. 8). The oligonucleotides for this reaction contain the three sets of pairs of VH oligonucleotides, e/e' and e2/e2' and e3/e3' in which amino acid VH71 is valine, alanine or arginine respectively. Appropriate mixing (as outlined above) allows for annealing and ligation of the three different rVH57-95 double stranded complementary oligonucleotides 3'VHdef/def (i.e., VH57-95[71V]) and 3'VHde2f/d'e2'f (i.e., VH57-95[71A]) and 3'VHde3f/d'e3'f (i.e., VH57-95[71R]). Aliquots of these three reactions are then amplified and appended with rsD and prs5 sites in step B by PCR using 3'VHFWD and3'VHBCK. These reactions contain Taq polymerase, as described above, and are cycled 25 times (94° C. for 1 min, 60° C. for 1 min, 72° C. for 2 min). The correct products are purified using Magic PCR Preps (Promega), suspended in 50 μl water and are then cut at prs2 and prs5 and reisolated. Approximately 1 μg of the reisolated rVH56-95 gene fragment is ligated into 5 μg pCLONALL precut with prs1 and prs5. Plasmid pCLONALL with the rVH56-95 insert is isolated and purified using Geneclean II (Bio101), and is used in step C to transform *E. coli* by electroporation (Dower, Miller et al. 1988). Transformants are selected, and the correct three products, rVH56-95:71V;A;R, are identified by diagnostic PCR and confirmed by automated ABI sequencing. Frozen stocks of each, designated rVH56-95 [71V;A; R].bact. are made.

Completion of construction of the nucleic acids encoding the four known CSRH2 regions genes is accomplished in steps D and E. The three rVHrsD-56-71*-95-prs5 inserts, freed by digestion of plasmid DNA are ligated to the four rVHrsB-59CSR2.1–4.lib which have been precut at rsD and prs5. The resultant rVHrsB-95CSR2.1–4 library is cloned into *E. coli* using the standard purification, ligation and electroporation processes outlined above. Transformants are isolated and about 50 are characterized by diagnostic PCR and 20 by automated sequencing to confirm that they contain the expected diversified versions of the four known CSRH. The ligation combinations of rVHrsB-59 CSR2 and rVH56–71*-95 necessary to construct the fully diversified rVHCSR2 library are rVHrsB-59CSR2.1lib. with rVH56-95:71V; rVHrsB-59CSR2.lib. with rVH56-95:71A; and rVHrsB-59CSR2.3 and 2.4lib. with rVH56-95:71R in steps D and E.

Step F, comprises sequential PCR reactions to append to the 3' end of the four diversified CSRH2 constructs rVHRSB-95CSR2.1–4 diversified CDRH3 s of different lengths and the convenient JCH1LNK restriction sites (i.e., rs3), and at their 5' ends diversify their parental CSRH1 and to append nucleic acids encoding VH17-rsB-24. The final PCR products of these reactions are designated rVH17-118CSR1&2&3.lib and contain all combinations of the diversified known CSRH1&2's and diversified CDRH3 of three different lengths.

These steps are carried out in the following 36 PCR reactions. Nine aliquots of each of the four different toothpicked frozen glycerol stocks of rVHrsB-95ΔCSR2.1–4lib.bact. are added to separate 50 μl primary PCR reaction mixtures containing Taq polymerase. The forward primers H3.5FWD, H3.7FWD and H3.10FWD are added to 3 of the 9 tubes containing each of the four CSR2s.bact. To each triplicate set of unique forward primers is added one of the following: the BCK primers H1.1BCK, H1.2BCK, or H1.3BCK. These primary PCR reactions are cycled 25 times (94° C. for 1 min., 60° C. for 1 min. and 72° C. for 2 min.). Following completion of the primary PCR, aliquots of each of the 36 reactions are taken for a secondary PCR reaction with new Taq polymerase, and primers H31FWD and H31BCK. The secondary reactions append VH100-rs3-118-rs4 and VH17-rsB-24 to the 3' and 5' ends respectively. The products are designated rVH17-118CSR123.lib. followed by a combination number (e.g., 1.1×2.2 ×3.5) which denotes the combinatorial arrangement of the three CDRHs in these products. Each of the 36 library products are characterized by diagnostic PCR and sequence analysis. Aliquots of the 36 libraries are pooled to generate the rVH17-118CSR1&2&3.lib.

In step G, DNA from the rVH17-118CSR1&2&3 library is digested with rsB and rs4. The digested DNA is purified using Magic PCR Prep (Promega) ligated into pCLONAL cut with rsB and rs4, purified and used to transform *E. coli* as detailed above. The transformants are isolated, characterized and designated rVHrsB-118CSR1&2&3.lib.bact.

In step H the rVHrsB-rs3 inserts are removed from the DNA of the rVHrsB-118&2&3.lib using restriction enzymes specific for rsB and rs3 to form fragments designated rVHrsB-114CDR1&2&31.3. These fragments are ligated using T4DNA ligase (New England BioLabs) to 5 μg rsB and rs3 digested rVH1-51-rs3.bact. DNA. The product is then isolated, purified and used to transform *E. coli* to generate rVH1-JCHLNK-ΔCSR1&2&3lib.bact. Individual clones from the library are then isolated and their sequence is confirmed by diagnostic PCR and sequencing. The library is then stored as frozen glycerol stocks. The bacterial transformants containing this library contain the canonical CSRH1 and H2 regions diversified in greater than one amino acid position, and CDRH3 of three different lengths and diversified in greater than one amino acid position. This procedure gives at least $10^5$ transformations which are identified by diagnostic PCR and sequencing to contain appropriately randomized amino acids at the diversified positions within the CSRH2 and H3 regions for the rVH1-114CDR2–3.library.

In step I, 5 μg of the rs2 and rs3 precut pVHACCEPTOR DNA (also referred to as pVH-CH, FIG. 9) is ligated to the rs2 and rs3 released insert rVH1-JCHLNKDCSR1&2&3.lib DNA (also referred to as rVHlib, FIG. 8), and the recovered purified product is designated rVHCH1.lib. This rVHCH1.lib product is used to transform E. coli to generate a frozen stock of bacteria containing the rVHCH1.lib. Greater than $10^6$ total members are obtained.

XI. VH and VL Library Sizes:

The above detailed reactions where two amino acid randomizations occur within each CSR theoretically allows the construction of 1200, 1600 and 1200 different CSR H1,2,3 respectively, and a rVH library size of $2.3 \times 10^9$. This exceeds the largest published recombinant VHCH1 library made by Similar technology (Griffiths, Williams et. al., 1994) by only about 2 fold. A smaller rVH library can be made using only 2 randomizations within the CSRH1 and H2 and one randomization within each of the three differently sized CDRH3. This procedure theoretically allows the construction of 1200, 1600 and 60 different CSR H1,2,3 respectively, and a rVH library size of $1.152 \times 10^8$. This is similar to the largest rVHCH1 library reported. The procedure outlined below allows subsequent pairing of individual members of such sized rVHCH1 libraries with individual members of equally sized rVLCL libraries (i.e., of $10^9$ as noted above and FIG. 4) on one piece of DNA in single bacteria. Based on the sizes of the rVHCH1 library and rVLCL library that are generated above, the potential size of the combinatorial rVab.lib (i.e., VHCH1lib×VLCL lib) is greater than $10^{18}$ members (FIG. 4).

XII. Construction of the rVab.lib (the VHCHllib×VLCLlib Combinatorial lib.) (FIGS. 11,12,14)

In this section the phagmid (fdø) which carry the rVLCLlib, designated Lox Receiver (LoxREC) (fdøRECEIVER, FIG. 11) and the plasmid (p) which carries the rVHCH library, designated Lox Provider (LoxPro) (pUC19PROVIDER, FIG. 11) are constructed and then are randomly recombined in vivo within individual bacteria onto a single phage vector (fdøCARRIER) which expresses the rVab rCHCH1 and rVLCL genes and produces on the surface of the phage functional versions of the rVab rVHCL1:rVLCL proteins. The rVab library construction phase is outlined in FIGS. 11, 12.

Construction is begun by reamplification of the rVHCH1 library maintained in the pVHACCEPTOR.lib.bact. using PCR, as described above, with primers pCFWD and pCBCK. The DNA product is isolated and cut with VHrs2' (Nco1) and VHrs4 (Not1) and is ligated using T4 ligase and standard methodology into LoxPRO precut with Nco1 and Not1. The LoxPRO used in this example is fashioned after the pUC based plasmid as described by Griffiths, A. D. et al. 1994) and contains an endogenous CH1, bounded by a Sfil and Not1 rs, preceded by a ribosome binding site (rbs), an in frame LpelB leader sequence (LpelB), followed by an inframe wild type loxP sequence (Hoess et al. 1982) and then an inframe myc sequence. In LoxPRO upstream from the LpelB is a mutant loxP511 sequence. DNA from the ligation mixture is purified and electroporated (Dower, Miller et al. 1988) into E. coli TG1 (Gibson 1984) to create the pUC based library LoxPRO.rVHCH1lib. (i.e., pUCLoxPROVIDER-rVHCH1lib). More than $10^8$ clones are obtained and the diversity is confirmed by sequencing independent clones.

In parallel, DNA is purified from the rVLCLlib.bact. (FIG. 8) and amplified by PCR with primers pCFWD and pCBCK. The PCR product is isolated, cut with VLrs2 (ApaL1) and VLrs4' (Asc1) and ligated using standard methodology into fd based LoxREC (i.e., fdøDOGRECEIVER). In LoxREC, upstream from the endogenous VHCH gene, and to be replaced by the incoming rLVCL.lib. there is an endogenous CL gene which is preceded by a leader sequence which ends in a ApaL1 in frame sequence which is followed by two terminator triplet codons. The endogenous CL gene is followed by two terminator triplet codons, an Asc1 and HindIII restriction site, and a mutant 511 loxP site (Hoess et al. 1986). DNA amplified by PCR is purified using Magic PCR Prep. The DNA is then cut with ApaLI and AscI and the digested DNA (about 6 μg), is purified on a 1.5% low melting-point agarose gel using Magic PCR Prep (Promega). Approximately 1 μg of the purified and cut rVLCL.lib DNA (FIG. 7) is ligated to about 5 μg of digested fdDOG-2loxVkdel (Sambrook, Fritsch et al. 1990) in a 60 μl volume with 1200U of T4 DNA ligase (New England Biolabs) (FIG. 11). Ligated DNA is purified from the ligation mixture using Geneclean II (Bio101), resuspended in 30 μl water and electroporated (Dower, Miller et al. 1988) into four 50 μl aliquots of E. coli TG1 cells grown in 1 ml 2×TY broth containing 1% glucose for 1h. Cells are then plated in dishes (Nunc) in TYE (Miller, 1972) medium with 12.5 μg/ml tetracycline (TYE-TET). After overnight incubation at 37° C., colonies are scraped off the plates into 7 ml 2×TY broth (Miller, 1972) containing 15% (v/v) glycerol for storage at −70° C.

The frequency of inserts is determined by PCR for each of the pools. Sequence diversity is confirmed by sequencing 8 clones of each pool. The pools are then combined to create the rVLCL.lib in fdøDOG as rVdLlib. outlined above. DNA from the ligation mixture is purified and electroporated (Dower, Miller et al. 1988) into E. coli TG1 (Gibson, 1984) to create the library rVLCL.lib in fdøDOG having greater than $5 \times 10^8$ clones. Diversity is confirmed by sequencing 30 independent clones.

Step 4: In vivo Recombination of VHCH1 and VLCL Genes

In this step, summarized in FIG. 14, VHCH1 and VLCL genes are recombined in pairs, onto single pieces of DNA to make the rVab library. Individual members of the VLCL and rVHCH1library are placed within a single bacteria via sequential incorporation within that bacteria of the rVLCL member via phage mediated infection and of the rVHCH1 member via DNA-mediated plasmid transformation. Once inside the bacteria, the two chains are combined onto the same piece of replicating DNA (fdøCARRIER) within the bacterium by the P1 CRE recombinase, provided by P1 phage infection, which catalyzes recombination at loxP site in a process termed 'recombinatorial infection' (Waterhouse, Griffiths et al. 1993). The process of recombinatorial infection for expressing recombinant proteins was originally described by Sternberg and Hamilton (Sternberg and Hamilton 1981); and Hoess et al. (Hoess, Ziese et al. 1982; Hoess, Wierzbicki et al. 1986) which are incorporated herein by reference and depicted in FIG. 14. In the process according to the invention, only those bacteria transformed with a rVHCH1/rVLCL combination (i.e., an rVab member) survive. Given the size of the rVHCH1library (greater than $10^8$, see above) and the rVLCL library (greater than $10^8$, see above), this type of combination, given unlimited bacteria, could yield a rVab.lib of greater than $10^{17}$ members.

According to the invention, the diversified rVLCL.lib is cloned into a tetracycline$^R$ fd phage (1st antibiotic resistance) containing any VH chain which is easily recognized and which will be replaced later in the process by rVH.lib chains. The diversified rVHCH1 chains are cloned into provider ampicillin resistant plasmids (2nd antibiotic resistance). The two libraries are then joined in *E. coli* via phage infection with fd phage containing the receiver VLCL chains (the rVLCL.lib) of bacteria previously transformed with plasmid DNA containing provider VHCH1 chains. A 1 liter culture of these bacteria is then co-infected with fP1 which is chorampenicol resistant (3rd antibiotic resistance) carrying the Cre recombinase. fd phage recovered from expanded colonies resistant to the antibiotics are used to infect *E. coli*. The percent of receptor phage with acquired rVHCH1 genes from the provider vector is expected to be greater than 5% based on the assumption that each bacteria generates 60 phage after overnight culture (Griffiths, Williams et al. 1994). It is also estimated that as long as this percent of the original triantibiotic resistant recovered cells acquires a rVHCH1 chain from the provider vector, the number of different phage within the rVab library will be close to the number of surviving bacteria.

Details of the Individual Steps for Expressing the rVLCL.1.6 and rVHCH1.L.b by CRE-LOX RECOMBINATORIAL FORMATION Phage P1 lysates are made by thermal induction (Rosner, 1972). *E. coli* C600 Su- (Appleyard, 1954) containing phage P1Cm c1.100r-m- (Yarmolinsky, Hansen et al. 1989) are grown in a 2 l baffled flasks containing 1 l of 2×TY, 25 µg/ml chloramphenicol, 10 mM MgSO$_4$ with vigorous shaking at 30° C. to an optical density of 0.6 at 600 nm. The temperature is then raised quickly to 42° C. by shaking in a 70° C. water bath. Shaking is continued for another 35 min. and then at 37° C. until lysis is visible. Cultures are centrifuged to remove debris and intact cells. Chloroform (100 µl) is added to the supernatant and P1 phage after 30 min. 30° C. infection of midlog *E. coli* TG1 (Gibson, 1984) grown in 2×TY broth with 5 mM CaCl$_2$. Phage infected *E. coli* are tittered by plating *E. coli* on TYE medium (Miller, 1972) containing 30 µg/ml chloramphenicol. Resistant colonies are counted after 24 h incubation at 30° C. and when expressed as transducing units (t.u.) are greater than $10^9$/ml.

One liter of 2×TY broth containing 12.5 µg/ml tetracycline (2×Ty-TET) is inoculated with $10^9$ *E. coli* carrying the rVLCL.lib cloned in LoxREC (i.e., fdDOG-2lox Vkldel Griffiths, A. D., et.al. 1994). The culture is incubated for 12 h at 30° C. in two 500 ml aliquots in 2 l baffled Erlenmeyer flasks. Polyethylene glycol is added to precipitate the phage (McCafferty, Griffiths et al. 1990), which are then suspended in PBS (phosphate buffered saline: 25 mM NaH$_2$PO$_4$, 125 mM NaCl, pH 7.0) and filtered through a 0.45 µm sterile filter (Minisart, Sartorius). The resulting phage, are tittered on mid-log *E. coli* TG1 (30 min, 37° C.) and plated on TYE-TET, (Griffiths, A. D., et.al., 1994) reaches ~$10^{10}$ t.u./ml.

The recombination process is monitored by withdrawing aliquots of the phage infected bacteria and serially diluting the bacteria onto TYE plates supplemented with 1% glucose and a variety of the three antibiotics, ampicillin (100 µg/ml), tetracycline (15 µg/ml) and chloramphenicol (30 µg/ml) and calculating the library size. The rVHCH1 library cloned into LoxPRO (i.e., pUC19-21loxVHdel in Griffiths, A. D., et al. 1994, see above) and contained in about $10^9$ *E. Coli*, is inoculated in 100 ml 2×TY broth containing 100 µg/ml ampicillin and 1% (w/v) glucose (2×TY:AMP:GLU). An aliquot is taken for c.f.u titering and the remainder of: the culture is grown overnight at 30° C. A second aliquot is then taken for c.f.u. titering and one 5 ml aliquot is used to inoculate 500 ml of 2×TY:AMP:GLU in a 2l Erlenmeyer flask and the culture is grown at 37° C. to an OD of 0.5 (600 nm). To this culture, 2×$10^{12}$ t.u. of rVLCL.lib in LoxREC is added and the culture is then divided into 5×100 ml aliquots. Each aliquot is mixed with 1l of 2×TY:AMP:GLU, pre-warmed to 37° C., and incubated at 37° C. without shaking for 30 min, and then with shaking until they reach an OD600 of 0.4 (about 30 min). Aliquots are then taken for c.f.u. titering. Two hundred ml of phage P1Cmc1.100r-m- lysate (about 6×$10^{11}$ t.u.) are added to each flask (at an m.o.i. of about 1) after the addition of CaCl$_2$ to obtain a final concentration of 5 mM in CaCl$_2$. This incubation is continued, with short durations of shaking every 15 min. for 1h at 30° C., followed by the centrifugation at 5,000×g for 15 min. The resultant pellets are suspended in 5 l 2×TYB (the original volume) with 100 µg/ml ampicillin (100A), 12.5 µg/ml tetracycline (12.5T) and 25 µg/ml chloramphenicol (25C) and 1% glucose (1G). An aliquot is taken for c.f.u. titering and the library size (number of ATC resistant c.f.u.) is confirmed to be greater than $10^{10}$. An aliquot is centrifuged at 12,000×g for 5 min. the supernatant filtered through a 0.45 m sterile filter, and the fd phage titer is determined by infecting log phase *E. coli* TG1 (30 min. 37° C.) and plating on TYE-TET.

The culture, in 5×1 liter aliquots, is incubated overnight at 30° C. (all culturing is with shaking unless specified) for 24 h in 2 l baffled flasks. Aliqouts are taken for bacterial c.f.u. and fd phage (using log phase *E. coli* TG1) titering with the total yield of fd phage being confirmed to be greater than $10^{13}$ t.u. The culture is centrifuged at 5,000×g for 15 min. at 4° C. and the fd phage are precipitated using PEP (McCafferty et al. 1990) and resuspended in a final volume of 10 ml PBS.

Five 2 l flasks, each with 1 l 2×TYB, are inoculated with *E. coli* TGI and grown at 37° C. until reaching an OD600 of 0.4 (about 4×$10^{12}$ bacteria). About 1–2×$10^{12}$ t.u. rVab are then added to the 5 l of *E. coli* and the cultures are incubated without shaking at 37° C. for 30 min. The number of *E. coli* infected with fd phage is confirmed by plating bacteria on TYE-TET plates to be greater than $10^{12}$. Tetracycline (12.5 µg/ml) is then added and the culture is grown for 16h at 30° C. The culture is then centrifuged at 5,000×g for 10 min. and the pellet comprising the library is suspended in 250 ml 2×TYB containing 15% glycerol and is stored in 15 ml aliquots at −70° C.

The efficiency of replacement of the endogenous VH to be exchanged in the phagemid receiver vector LoxREC with rVHCH1 chains from the provider vector LoxPRO (i.e., pU19-2loxVHlib) ((Griffiths A. D., et.al., 1994), is determined to be less than about 20% by analyzing 200–300 individual colonies from the rVablib. Colonies are transferred onto TYE-TET plates and grown overnight at 30° C. Identification of colonies possessing the recombinant VH genes is accomplished using colony hybridization (Tomlinson et al. 1992) with a primer complementary with the CDR3 region of the exchangeable VH of the LoxREC. Between 40–50 clones lacking the endogenous VH gene (i.e., the antiTNF VH as used in fdDOG-2lox Vdel by Griffiths, A. D. et al., 1994) are screened by PCR (Gussow and Clackson, 1989) for the presence of heavy chains with the primers similar to PELBBCK (5'GAA ATA CCT ATT GCC TAC GG) and CH1. LIBSEQFWD (i.e., 5'GGT GCT CTT GGA GGA GGG TGC) and for the presence of light chains with the primers like fdBCK (5'GCG ATG GTT GTT GTC ATT GTC GGC) and CL.(or CL) LIBSEQFWD (respectively, 5'CAA CTRG CTC ATC AGA TGG CG OR 5'GTG GCC TTG TTG GCTTGA AGC) (Griffiths, A. D., et al. 1994). Both chains are expected to appear among the clones at frequency of about 20–30%.

Aliquots are then spread on TYE-TET in dishes (Nunc), and are incubated overnight at 30° C. as well as being tittered by serial dilution on small TYE-TET plates to allow determination of the number of colonies on the large plates. The plates containing the necessary bacteria to generate $10^7$ clones are accumulated, and the bacteria are scraped into 10 ml 2×TYB containing 15% glycerol to make stocks corresponding to rVab libraries of greater than$10^7$ clones.

XII. Step 5—Generating Phage and Displaying the rVab.lib on Phage Surfaces (FIG. 14)

As constructed above, each phagemid carries and expresses an individual member of the rVab.lib. As shown in FIG. 14, VHCH1 protein is expressed as a fusion protein coupled in open reading frame to the NH2-terminus of the fd gpIII coat protein gene and is therefore displayed on the mature phage surface as an attached surface protein. The VLCL protein, expressed via appropriate leader and double terminator codons as a soluble protein, is released into the bacterial periplasmic space wherein under reducing conditions it spontaneously forms active disulfide linked dimmers with VHCH to produce the desired functional recombinant rVab on the surface of the mature phage. Phage lysates expressing the entire combinatorial rVab library (one rVHCH and one rVLCL gene per phage) are made with the aid of helper phage.

Phage, helper phage, plasmid construction, and titering are as generally described in the literature and phage and helper phage are available from commercial sources (Stratacyte CA, or Cambridge Antibodies Technologies, UK). The lysates are in general made as follows: five l of 2×TY-TET is inoculated with a 15 (5–20) ml aliquot of the rVab phage library (greater than $2 \times 10^{10}$ c.f.u.), the cultures are grown overnight at 30° C. in baffled flasks (1 l medium/fl), centrifuged at 5,000×g for 15 min at 4° C. and the fd phage are precipitated with PEP (McCafferty et al. 1990). Phage is then resuspended in a final volume of 10 ml PBS. These lysates are designated rVab.lib.F and have total yields of rVab expressing nature phage of from $10^{13}$ to $10^{14}$ t.u.

EXAMPLE 2

Preparation of SOMERs For The Human Type 1 Muscarinic Acetylcholize Receptor

In this example, following Stages I and II of the TSA process (FIG. 1), rVabs from the rVab.lib are identified, isolated and used to establish an assay for small organic molecules (SOMER) which bind to and regulate the activity of only one subtype of human muscarinic cholinergic receptor (huAChRm). Such SOMERS are useful new discovery leads for such diseases as Alzheimer's and other memory and learning deficits. The steps outlined below constitute Stages I–II (see FIG. 1) of the process of the invention and are those necessary to isolate from the rVab.lib those rVab members which bind (T+) to type 1 of the AChRm subtypes, regulate its activity (A+), and are specific and selective (S+) for subtype 1 of the human muscarinic receptor (huAChRm1). Stage III of the invention, using these TSA+ rVabs to generate 3D models of ACHRm1-specific pharmacophores (BEEPS, see below) and obtain SOMERs is briefly outlined at the end.

Stages I–II detail the steps necessary to obtain and use the specific. AChRm1 rVab to establish simple rapid radioreceptor assays for small organic molecules (SOMERs) which specifically bind and regulate huAChRm1. As disclosed herein, and illustrated in FIGS. 18 and 19, these rVabs are used to discover active surfaces on the huAChRm1which are not present on the other huAChRm2–5 subtypes. In addition, the rVabs may be agonists or antagonists at selective huAChRm subtypes (i.e., $m_{1-5}$) and may exhibit specificity(S+) of action between one m subtype and the other four.

Phase I of this process reconstitutes functional huAChRm which are the target of these assays. Phase II first identifies the rVabs contained within the rVab.lib which bind to huAChRm1 (i.e., are T+), and are selective among the five huAChRm subtypes (Andre, Marullo et al. 1987) as well as specific for huAChRm over non-cholinergic neurotransmitter receptors. In this example these two attributes are referred together as S+. Subsequently, Phase II identifies and isolates the subpopulation of TS+ huAChRm rVab which regulate the activity of the huAChRm1(A+) with similar TS+ attributes. The rVabs with all these attributes are referred to as TSA+ rVabs. Phase III converts the TSA+ rVabs to reporters (i.e., rVab.reporters) and establishes validated automated rapid receptor binding screens for small organic molecules (SOMERS) which competitively displace active rVab reporters from active surfaces on huAChRm1. Among these SOMERS are those having the desired activity profile of a pharmaceutical discovery lead, i.e., selective specific regulation of AChRm1.

Phase I-A: Obtaining AChRm

Cortical membranes enriched in huAChmR are prepared from brains (fresh or frozen, human, porcine or bovine) as outlined by Haga & Haga (Haga and Haga 1983). Membranes are prepared by homogenization in standard fashion (i.e., with protease inhibitors) and AChRm is solubilized by treatment with 1% digitonin, 0.1% NaCholate in 50 mM NaCl/buffer. The soluble receptor is purified over an 3-(2'-amino benzhydryloxy) tropane (ABT) affinity column and is eluted from the ABT column by atropine. Soluble receptor is subsequently applied onto a hydroxyapatite column to remove the free atropine. The receptor is then eluted with high potassium phosphate and 0.1% digitonin and is further purified through a second round of ABT purification as rioted above. Two rounds of HPLC purification over tandem linked TSK4000SW and TSK3000SW columns provides the final purification and the receptor is suspended in 0.1 M potassium phosphate with 0.1% digitonin.

As a secondary source, the five huAChRm1–5, expressed as recombinant proteins (rhuAChRm1–5) in Sf9 cells containing an expression vector baculovirus construct carrying one of the huAChRm as originally described by Vasudeva (Vasudevan, Reilander et al. 1991) are obtained from commercial sources (BioSignal, Inc., Montreal, Canada). Other alternative sources of huAChRm are various tissue culture cell lines transfected and expressing cloned huAChRm (Kubo, Fukuda et al. 1986; Shapiro, Scherer et al. 1988; Buckley, Bonner et al. 1989; Buckley, Hulme et al. 1990; Tietje, Goldman et al. 1990; van Koppen and Nathanson 1990; Kashihara, Varga et al. 1992; Beth 1993; Lazareno, Farries et al. 1993; van Koppen, and Lenz et al. 1993).

Phase I-B: Obtaining the G proteins (GP)

Go, Gi and Gn (referred to as G protein [GP] in text and G in Figures) are purified as described (Sternweis, 1984; Haga, 1986, and Haga, Uchiyama, et.al., 1989). Brains (150 g), porcine, bovine or human (obtained from commercial or non-profit sources) are homogenized, the membranes pelleted and then solubilized with 1% NaCholate in 20 mM TrisHCl (pH 8.0) 1 mM EDTA, 1 mM DTT (1%Cho-TED) with 0.1 mM benzamidine (2 L vol.). After centrifugation, the supernatant is applied to DAE Sephacel and the fractions binding [$^{35}$S]GTPS are eluted with linear NaCl, in 1%Cho-TED, concentrated, and applied and eluted from Ultrogel AcA 34 in 0.1M NaCl in Cho-TED. The fractions with [$^{35}$S]GTPS binding activity are pooled with TED+0.1M NaCl (450 ml) and applied to heptylamine-Sepharose, washed and finally are eluted with a linear gradient of 0.25% NaCho-TED+0.2M NaCl vs. 1.3% NaCho-TED+0.05M NaCl. This material (a mixture of Gi and Go) is applied to DEAE-Toyopearl, prewashed with TED+0.6% Lubrol PX (0.6%LPX-TED) and eluted with a linear gradient of NaCl in 0.6%LPX-TED. The Gi fractions elute first, then the Go fractions. Each is collected separately and is stored at −80° C. until use. Before use, the Lubrol is changed to 0.8% NaCholate, in TED+0.5M K phosphate buffer pH7, 0.1MNaCl) on a small column of hydroxyapatite.

Phase I-C: Reconstitution of an active AChRm:GP complex

Reconstitution is accomplished as per Florio and Sternweis (Florio, 1985). Porcine [or human brain total lipids: as per Folch, J., Lees, M., and Stanley, G. H. S. (Folch, Lees et al. 1957). The lipid mixture is prepared (Haga, 1986) from brain extract (Folch fraction I) (1.5 mg each) and total lipids (1.5 mg each) suspended in 1 ml HEN (20 mM Hepes-KOH buffer pH 8.0, 1 mM EDTA and 160 mM NaCl) with 0.18% deoxycholate and 0.04% sodium cholate. rhuAChRm (0.2–0.4 nmol/ml [$^3$H]QNB binding sites in PD (0.5M potassium phosphate buffer pH 7.0 and 0.1% digitonin (10–40 μl)) are mixed with 0.1 mM oxotremorine in HEN, and then with 100 μl of lipid mixture (final vol. 200 μl) to give QNB:R complex. The complex is then run through a Sephadex G50 column and the void volume (1–8 pmol [$^3$H]QNB binding sites, 400 μl) is collected. The huAChRm:QNB complex is mixed with G protein (mixtures or separate G-proteins, 0–200 pmol of [$^{35}$S]GTPgS binding sites in 40 μl cholate solution) CN-TED and HEN (50 μl) containing MgCl$_2$ and DTT (final concentration 10 and 5 mM respectively) and incubated at 0° C. for 1 hr. This huAChRm1:GP mixture is diluted before use with p3–5 vol of HEN.

Figure 19:
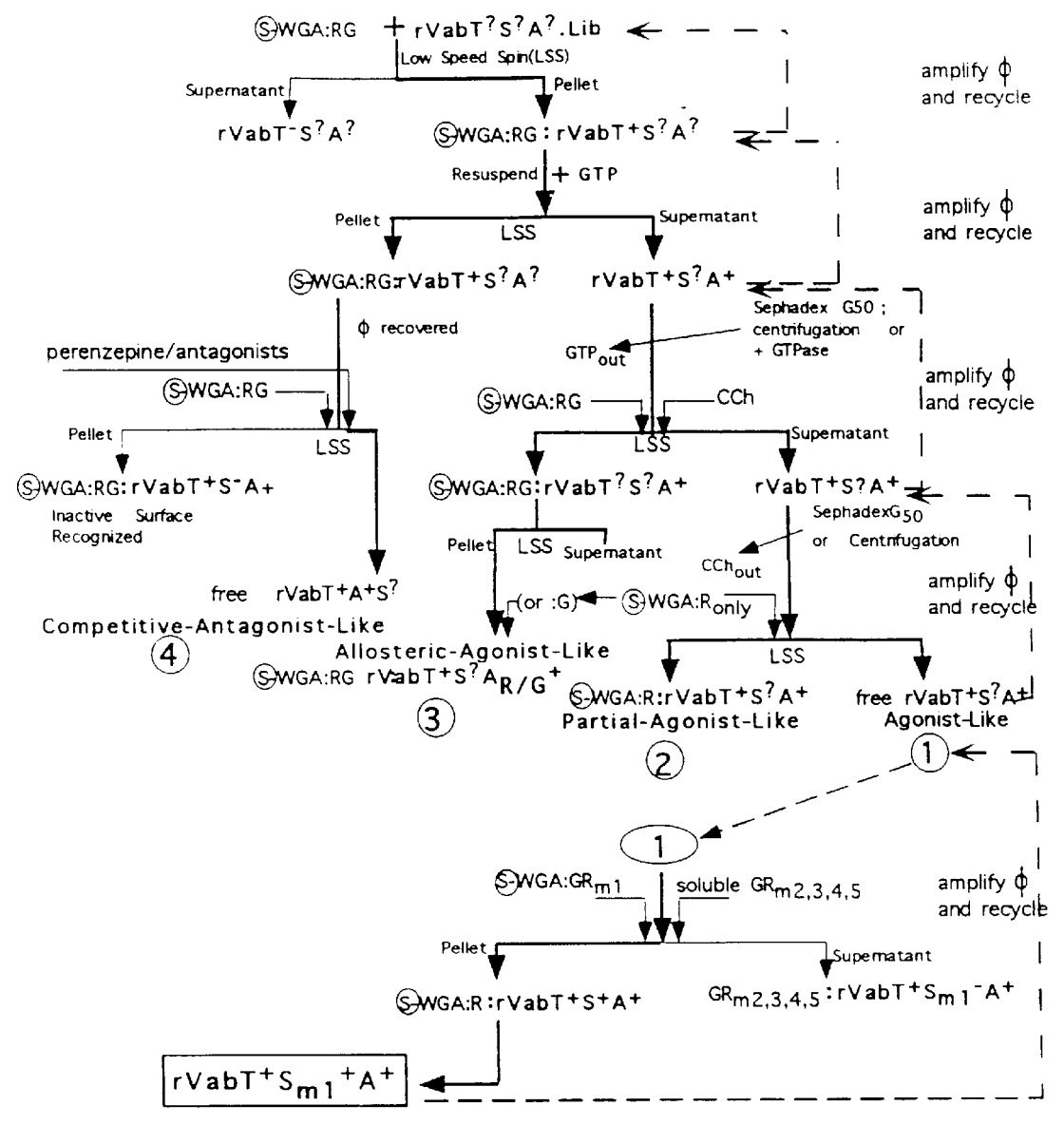

Phase I-D: Attachment of active huAChRm to matrices (FIG. 19)

huAChRm (abbreviated AR in text and R or T in Figures), alone or complexed with GP, is attached to a Sepharose (or agarose)-type matrix by taking 5 ml of matrix (WGA-Sepharose, mmolWGA/ml Sepharose, 50% v/v, prewashed and suspended in buffer A (25 mM Potassium phosphate buffer, [pH 7.0 ], 0.8 mM EDTA, 10 mM MgCl2, 230 mM NaCl, 0.06% BSA, and 4 mM HEPES KOH buffer (pH 8.0]) and mixing it with less than 1 ml reconstituted AR:GP complexes (100 pmol AR/ml). The mixture is then incubated at room temp (r.t.) for 30 min, diluted with buffer A to 20 ml and the Sepharose is allowed to settle (or centrifuge at low speed [5,000×g, 1–2 min]). The Sepharose is then resuspended in 20 ml buffer A and the washes are repeated twice to provide purified AR complexed-Sepharose WGA [sWGA:ARGP] material. Recombinantly derived or native AR:GP complexes with appropriate sugar residues bound to WGA in this process remain active as matrix-attached receptor in agreement with published data showing glycosylation is not required for AChRm activity (Habecker, Tietje et al. 1993). Quantitation of bound AR:GP to sWGA is verified by [$^3$H]QNB ±10 μM atropine and [$^{35}$S]GPTS or [$^3$H]GppNHp ±0.1 mM GTPS or GppNHp binding using standard binding assays (Berrie, Birdsall et al. 1985; Haga, Haga et al. 1986; Wheatley, Hulme et al. 1986; Poyner, Birdsall et al. 1989).

In parallel reactions, AChRm (or GP), natural or recombinantly expressed preparations, are attached by standard techniques to plastic, directly or secondarily, through matrix attached antibodies, naturally derived or rVab-type, which recognize epitopes on the receptor, glycoprotein, G-protein or small peptide tags (i.e., the c-myc and other amino or carboxy terminal in frame tagging peptides, available in various spaced commercial expression vectors). After attachment of AR, the unoccupied reactive matrix surfaces are blocked by application of various standard blocking agents (i.e., BSA, milk etc.).

Phase II: Panning for TSA+rVab

In this stage, rVabs which possesses TSA+ attributes are identified a s those which bind to AChR directly or indirectly attached to the matrix, with or without G, in buffer conditions similar to those used for AChRm radioreceptor binding studies. These conditions maintain receptor activity. In all cases plastic and not glass is used for direct attachment matrix surfaces and reaction vesicles to minimize rVab nonspecific absorption to glass. The buffer for these reactions is a 10 mM potassium phosphate (pH 7.0), 0.8 mM EDTA, 10 mM $MgCl_2$, 0.230 mM NaCl, 0.06% BSA, 4 mM Hepes-KOH (pH 8.0) buffer, and optionally further comprising guanine nucleotide (GTP) and/or muscarinic agonist or antagonist as detailed below. This stage isolates four types of A+ TSA+ rVab antibodies: agonist like (Ago+), partial agonist-like (partAgo+), allosterically agonist (Alloago+) and antagonist-like (Antago+) (outlined in FIG. 19).

Phase II-A: Panning for receptor [Target ($T^+$)] recognition

The general process is summarized in FIG. 16 and the specific application in FIG. 19: Five ml of the rVab.lib ($10^{11-12}$PFU/5 ml, and suspended in buffer) is mixed with 1.0 ml settled s-WGA:GAR in buffer A, and incubated at 30° C. with gentle shaking for 60 min. The mixture is then centrifuged at low speed (LSS) of 500×g for 15 min. The supernatant is decanted and diluted with buffer A to 10 ml. These washes are repeated 3 times rapidly and the rVab in the final pellet resuspended in buffer A and designated as the $T^+$rVab.lib. (FIG. 19). Phage are released by elution with 100 mM triethylamine (Marks, Hoogenboom et al. 1991). Aliquots are withdrawn and tittered for phage. The population of isolated phage are then amplified by infection and induction of new lysates and panned again 2–4 more times to generate the final T+rVab population of phage for subsequent isolation of the four types of A+rVabs.

Phase II-B; Panning for Active rVabs (A+rVab) (Phase IIB)

In this process (general outline in FIG. 17, specific application in FIG. 19), the subset of rVab from the amplified T+rVab population which are potentially agonistic are induced by the addition of guanine nucleotides to dissociate from the matrix attached R:G complex and be isolated as free TA+rVab in the supernatant. In this process, the rVab which bind and act as antagonists, or bind to nonactive surfaces, remain matrix-receptor associated after the addition of guanine nucleotide. The negative influence of GTP on T+rVab binding is taken as indicative of potential agonist action of the bound rVab based on the observation that in functionally coupled AR:GP complexes there is a negative reciprocal interaction between the binding of GTP or GDP to the G protein, and agonist to the receptor, which can be observed as an immediate dissociation of either from the complex (Smith, Perry et al. 1987; Poyner, Birdsall et al. 1989; Lazareno, Farries et al. 1993). No such reciprocal interactions occur between antagonist and guanine nucleotide binding (Buckley, Bonner et al. 1989).

The TA+ rVab released into the supernatant are further separated and isolated as one of three types of agonists in separate panning steps (see below Phase IIB-i,ii,iii). The specific muscarinic activity of the rVab is confirmed at the end of all isolations using AChRml activity assays in which potential TSA+rVabs (a) compete with radiolabelled antagonist (or agonist), (b) dissociate prebound [$^{35}$S]GPTS or [$^{3}$H]GppNHp from matrix bound AChRm:GP complexes, (c) stimulate GTPase and or GTP exchange, and d) regulate the activity of other effector systems coupled to the AChRm1 (i.e., adenylate cyclase, phospholipase, K channels) in various published in vitro, cellular or animal assay systems (Yatani, Mattera et al. 1988; Fraser, Wang et al. 1989; Shapiro and Nathanson 1989; Kobayashi, Shibasaki et al. 1990; van Koppen and Nathanson 1990; Weiss, Bonner et al. 1990; Yatani, Okabe et al. 1990).

In Phase IIB, addition to bound T+rVab of ACh itself can also be used, via the same type of induction of rVab dissociation from AChR, to isolate those rVab which bind not to the ACh binding pocket but to GP at active nucleotide binding surfaces or to other surfaces on AR or GP which are active and allosterically connected with the cholinergic binding surfaces of the AChRm1.

Specifically, at the start of Phase IIB, the amplified T+rVab.lib isolated in Phase IIA is mixed with matrix-bound AChRm1:G complex, in 10 volumes buffer A as noted above for 30 min at 37° C. The pellet is centrifuged at low speed, resuspend in 10 vol cold buffer A and immediately recentrifuged. The washed pellet is resuspended in 10 vol cold buffer A containing 100 uM GTP. After less than or equal to about 1 min. the matrix:AR:GP complex is centrifuged at low speed, and the supernatant is separated from the pellet to be used to isolate three different types of agonistic rVab in Phase IIB-i,ii-iii. The pellets are washed in similar fashion with buffer A three (3) times and analyzed in phase IIB-iv for muscarinic antagonist (Antago+) activity as detailed below. Throughout these phases, aliquots of supernatant are taken to titer the phage, and if less than $10^6$/ml, the phage are amplified and recycled as above 2–3 additional times. To the final supernatant, containing rVab induced to dissociated via GTP addition, GTPase and GDPase are added and the supernatant incubated 30 min at 30° C. The solution is then chilled and passed over a Sephadex G50 fine column using buffer A and the void volume, free of any remaining nucleotides, is taken and labeled $TA^{+(GTP+)}$rVab.lib.

Identification of Antagonist Activity

The T+rVab lib, for which binding is not modified by addition of GTP, and which is recovered bound to matrix in the presence of GTP, is released from matrix and the phage harvested by PEE, precipitation in Phase IIB-iv. The phage are then resuspended and mixed with s-WGA:RG in 2 ml buffer A containing saturating amounts of antagonist (atropine 10 $\mu$M, perenzepine 1 $\mu$M, scopolamine, 1 $\mu$M). Following incubation for 60' at 30° C. phage and s-WGA:RG are centrifuged at low speed and the supernatant is collected. The free phage are isolated, and amplified (as noted above) and the population recycled an additional 2 to 3 times by combining with s-WGA:RG to remove from the supernatant phage which, in the presence of antagonist, do not bind to s-WGA:AR. The phage in the final supernatant contain the expressed A+rVab members which are muscarinic antagonist-like (Antago+) are designated at the end of Phase IIB-iv, as TAntago+ huAChRm1 rVab.lib. [see FIG. 19, rVab-4].

The pellet from incubation with muscarinic antagonist in the above Phase IIB-iv contains a T+rVab sublibrary which has members which interact directly with surfaces on the G protein of the AR:GP complex and are guanine nucleotide like regulators of the AChRm1:G complex. Phage are freed from the matrix, amplified and incubated with matrix bound G-protein in buffer A. The matrix, and attached rVab, are then centrifuged, washed and attached phage isolated. Confirmation of G-like activity among these isolated rVabs is done in standard radioreceptor binding assays establishing competition with radiolabelled GppNHp or $GTP_\gamma S$ for binding to GP.

Phase IIB-i,ii,iii: Separating GTP Sensitive A+rVab into Ago+($^{GTP+CCh\ sensitive}$) and alloAgo+($^{GTP+\ CCh-insensitive}$) AChRm1-rVab (FIG. 19 )

One to 10 ml of the $TA^{+(GTP+)}$rVab.lib is mixed with 1 ml sWGA-GR, incubated 60' min, 30° C. in buffer A with 300 $\mu$M stable muscarinic agonist carbachol (CCh) and is then centrifuged at low speed. In Phase IIB-iii, the pellet is washed with buffer A three (3) times, and resuspended in buffer A and the phage isolated in standard fashion. This phage population, labelled $TA^{+(GTP+CCH-)}$rVab.lib, contains the allosterically acting muscarinic like agonist (alloAgo+) rVab members (FIG. 19, rVab-3).

The supernatant from the above Phase IIB incubation with CCh is passed over Sephadex G50 (fine) in Phase IIB-i,ii and the phage are collected in the void volume of the column (as outlined above) to obtain CCh free rVab which are blocked from binding to AChRm by CCh. These phage are labeled as the $TA^{+(GTP+CCH+)}$rVab.lib and contain the Phase IIB-i and ii rVab.lib members which are competitive-ACh muscarinic full(i) or partial(ii) agonist-like (Ago+) antibodies (i.e., rVab-1 and 2 in FIG. 19).

Phase II-C: Separating Selective(S+) from non Selective(S−) $TA^+$ rVabs

All four types of AChRm A+T+rVab phage isolated in Phase IIB (label-Led rVab-1,2,3 &4 FIG. 19), are taken separately, and mixed with 1 ml sWGA:GR m1 in buffer A containing soluble complexes of GP and AChR of subtypes 2–5 (i.e., G:AChRm2–5 complexes). These complexes are added as the competing target peptide (analogous to comp-T-pep in FIG. 16) which contain greater than 10 fold excess of surface epitopes which are not to be recognized by the ml specific A+rVabs, incubated 30° C., 60 min and then centrifuged at low speed(FIG. 19). The pellets contain the S+rVabs.lib members and these are resuspended in 10 vol buffer A and washed immediately. The phage are recovered in standard fashion, amplified and cycled through Phase IIC two to four additional times. Frozen stock bacterial cultures and phage lysates are prepared for each of the four A+ types of AChRm1 specific(S+) and are designated TS(Ago; partAgo; alloAgo; or antAgo)+ rVab.lib. In an alternative embodiment, isolation of the AChRm1 specific rVab library is done on the T+rVab.lib before selecting for the A+rVab.lib (FIG. 16) and the population is amplified for subsequent A+ selection as defined above.

Stage II-E: Confirmation of A+ activity among individual members of the TSA+ rVab AChm1 lib Individual members (10–20) of each of the four A+ type TSA+ rVab AChRm1 library identified above are obtained and phage lysates are generated for each by standard technology. The A+ profile for individual phage members of each of the above four A+ library is confirmed and quantitated by a nM ED50 value in one or more of the following standard radioreceptor and receptor-coupled activity assays. The radioreceptor assays use 1) active soluble targets (i.e., AChRm, AchRm:G and G-protein complexes); 2) radiolabelled AChRm [$^3$H]agonist or antagonist, or [$^3$H, or $^{32}$P] GTP, or GMPPNP or [$^{35}$S]GTPS in buffers used for rVab isolation; and 3) various dilutions of individual rVab members to be tested. The reaction mixture contents are incubated at 30° C. for 30 min and the targets are recovered free of soluble radioligand by standard filtration or PEG precipitation. The reduction in specifically bound radiolabel is then quantitated.

The degree of agonist activity for Ago+, partAgo+ and alloAgo+ rVab members is demonstrated by dose response alteration of any one of a number of AChRm1 coupled effector systems. Individual antagonism (Antago+) is demonstrated by dose response blockage of the ACh agonist effect on the particular receptor coupled system.

Phase III. Conversion of Selected A+ rVab to rVab Reporters

Figure 18:
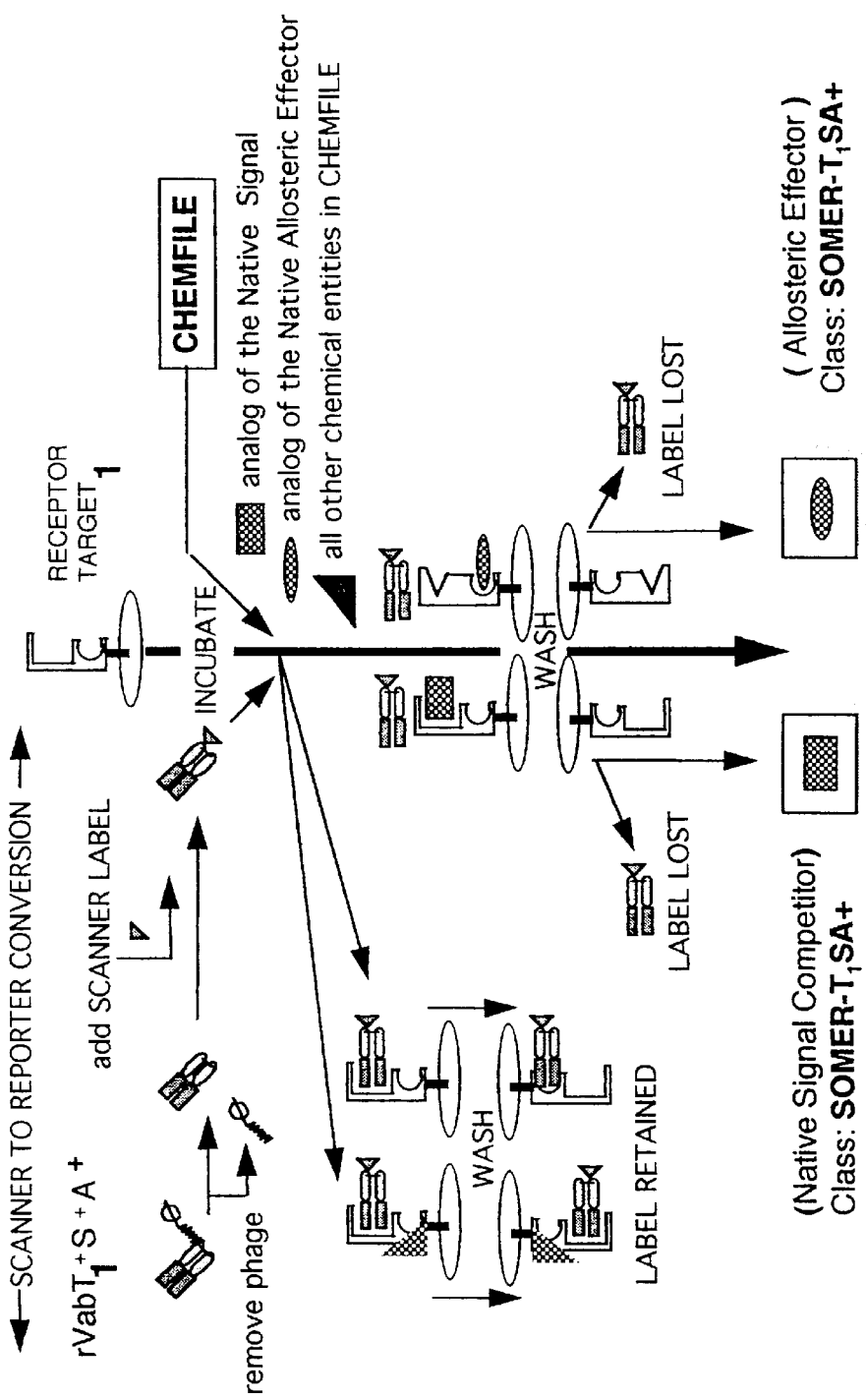

A. Preparation of Reporters and Competitive Binding Assays to Identify SOMERs (FIGS. 18,19)

DNA is isolated from phage lysates prepared from bacteria grown from two to five individual TSA+rVab.bact stocks from each of the four classes of A+ libraries characterized above to have A+ activities with ED50 values of 1–30 nM. The DNA is digested with ApaL1 and Not1 to release from the fdøCarrier the rVLCL-rVHCH1 rVab construct. One µg of the insert is isolated and mixed with 5 µg DNA from pEXPRESSORrVab (pEXPRESSORrVab-1, see FIG. 9), precut with ApaL1 and Not1, and 1200U T4 ligase (Sambrook, Fritsch et al. 1990). The ligated products are purified and electroporated into E. coli (Dower, Miller et al. 1988). Transformants are grown and characterized by diagnostic PCR and then sequenced. Correct constructs of each are then grown, the recombinant rVab (i.e., VHCH1: VLCL dimmer chains) induced and the rVab products are recovered in the supernatant by precipitation with Sepharose coupled VH or VL chain antibodies or antibodies to peptide sequences (ISOTAGS) included in pEXPRESSORrVab-I (FIG. 9C) and fused in frame to the carboxyterminus of CH1. The rVab are then released from the precipitating antibody. The VHCH1 chain of the rVab is then phosphorylated in a constant region C terminal domain attached in frame (Li, et al. 1989) when rVab is ligated to pEXPRESS-rVab. The phosphorylation reaction uses protein kinase and [$^{32}$P]ATP following published methodology and the radiolabelled product is isolated in the void volume of a G50 column. The radiolabelled rVab is mixed with BSA and stored at −4° C. until use.

To establish a saturation isotherm and ED50 for the labelled rVab with its active target (soluble or membrane bound; GP, AChrR m1, or AChrRm1:GP complexes), the binding of rVab is determined from reaction mixtures (50 µl) comprising from 1000–1,000,000 cpm of radiolabelled rVab with and without 1000 folded excess of unlabelled rVab in buffer B. Identical control assays are done with AChRm2-5, AChRnicotinic, or other non-cholinergic G-protein linked neurotransmitter receptors (e.g., beta-and alpha adrenergic, and opiate receptor). These assays are incubated for 30 min at 30° C. The [$^{32}$P]rVab:target complex is PEG precipitated (or filtered with membrane bound target) and counted for radioactivity.

The induced dissociation of rVab from its target by an allosteric effector (i.e., the Ago+rVabs with GTP) defines the class of allosteric rVab agonists. A series of competition binding assays is then performed using less than, or equal to, the ED50 amount of [$^{32}$P]rVab with increasing concentrations of the nonlabelled form of the same rVab, other rVab, standard muscarinic specific ligands (agonists and antagonists), and a number of noncholinergic ligands as controls to further characterize these rVabs.

These assays establish a saturation binding isotherm, an apparent Kd for rVab and target association, and IC50 values for various ligands and other rVabs. The reactions carried out in the presence of increasing concentrations of other members of the same TSA+ rVab group define the rVab with the lowest IC50 value. This rVab is then converted to a radiolabelled form for use in obtaining saturation isotherms and various competition curves. In addition to the radiolabelled rVab, these assays further may contain 1) target agonist; 2) antagonist; 3) GTP; and 4) combinations of all three. Standards such as nicotine, muscarine, ATP, GMP, and the various small organic molecules previously reported in the literature to have affinity for regulation of AChRm receptor of the m1-5 type regardless of affinity or selectivity may also be included. Saturation isotherms are generally conducted over a concentration range of four to six orders of magnitude.

rVab's with affinity for AChRm1 of less than about 10 nM, selectivity for AchRm1 over AchR types m2-5of >100 fold, and specificity regarding non-cholinergic soluble receptors of 1000 fold are appropriate as rVab-REPORTERs for A+ activity for use in Stages II and III of this invention wherein SOMERs are identified in CHEMFILES or synthesized based on BEEP models (see below).

Phases IV-VI

In the last three phases of the invention, which are part of TSA Stage III, the TSA+ rVabs are grouped according to common epitopes and attributes (Phase IV), 3D-models of active pharmacophores (BEEPS) are derived (Phase V) and the pharmacophores used to find SOMERs in existing CHEMFILES or by synthesis (Phase VI). The grouping of TSA+rhuAChRm1 in Phase IV is accomplished according to a) the common surfaces recognized by the rVab (defined by competition by peptide fragments of the AChR; b) the type of activity exhibited by the rVab (partial or full agonist, antagonist, competitive or allosteric with ACh or GTP) and; c) the diversified amino acids of the V regions found in the rVab.

Figure 23:
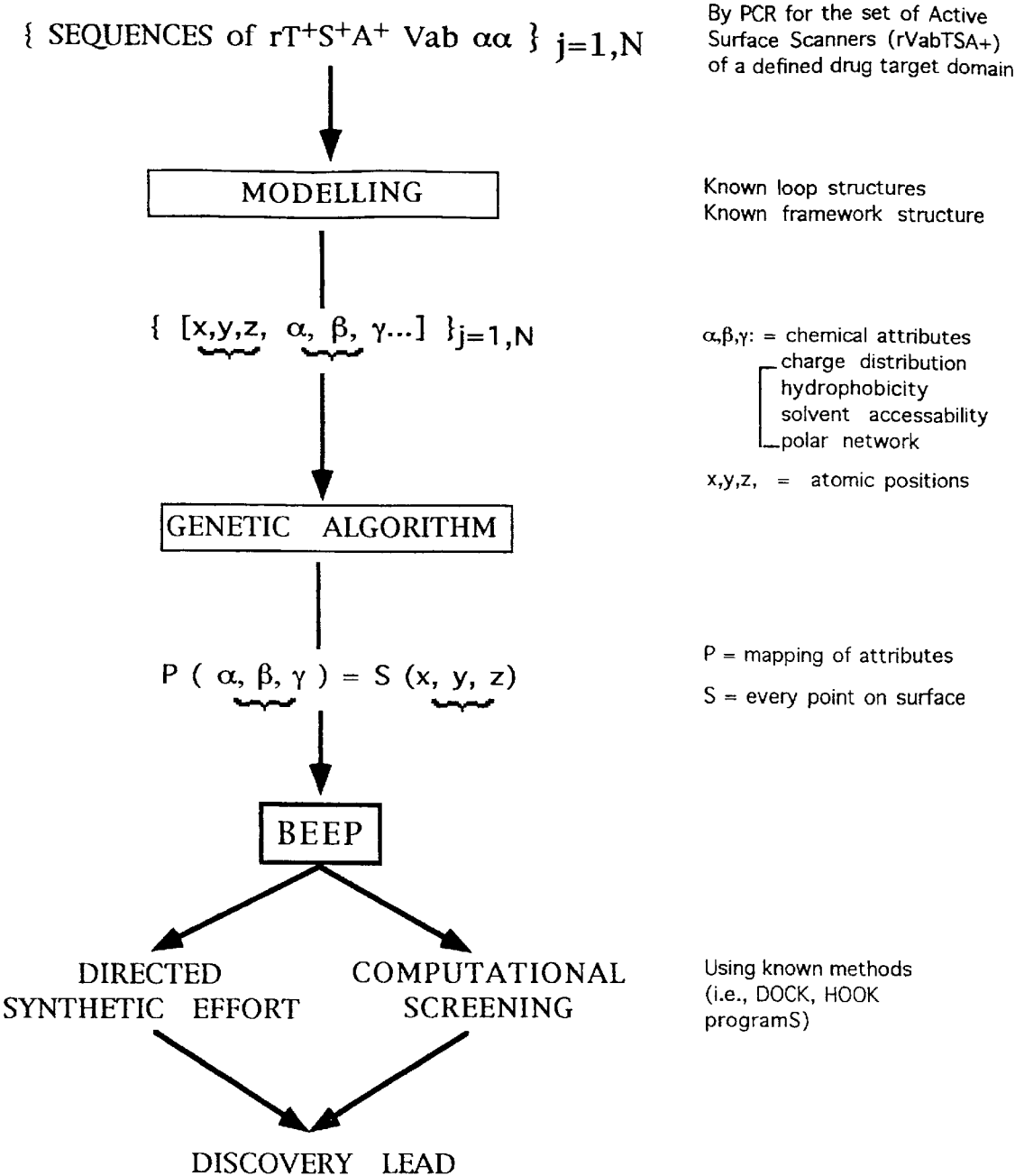

The Stage III analysis of the TSA+rVabs which creates a 3D model pharmacophore (FIGS. 23–25) is performed based on a genetic algorithm directed comparison of the array and positions of the amino acids in the V regions of the active rVab's, including CSR, CDR and framework residues. The 3D atomic model formulated by this process is designated a "biologically enhanced ensembled pharmacophore" (BEEP). The BEEP contains sufficient information to describe the elements of a SOMER necessary for the activity profile of the active rVabs within that particular group.

In Phase VI, the BEEP is used in a variety of available programs (HOOK, LOOK, and DOCK) for computational screening (Phase VIa) of available CHEMFILES for huAChRm1 SOMERs and, in a rational drug design effort, to direct the actual synthesize of huAChRm1 SOMERs (Phase VIb). SOMERs obtained by either approach are then confirmed as TSA+ AChRm1 agonists or antagonists in in vitro, cellular and animal assays, known to those versed in cholinomimetics.

Figure 15:
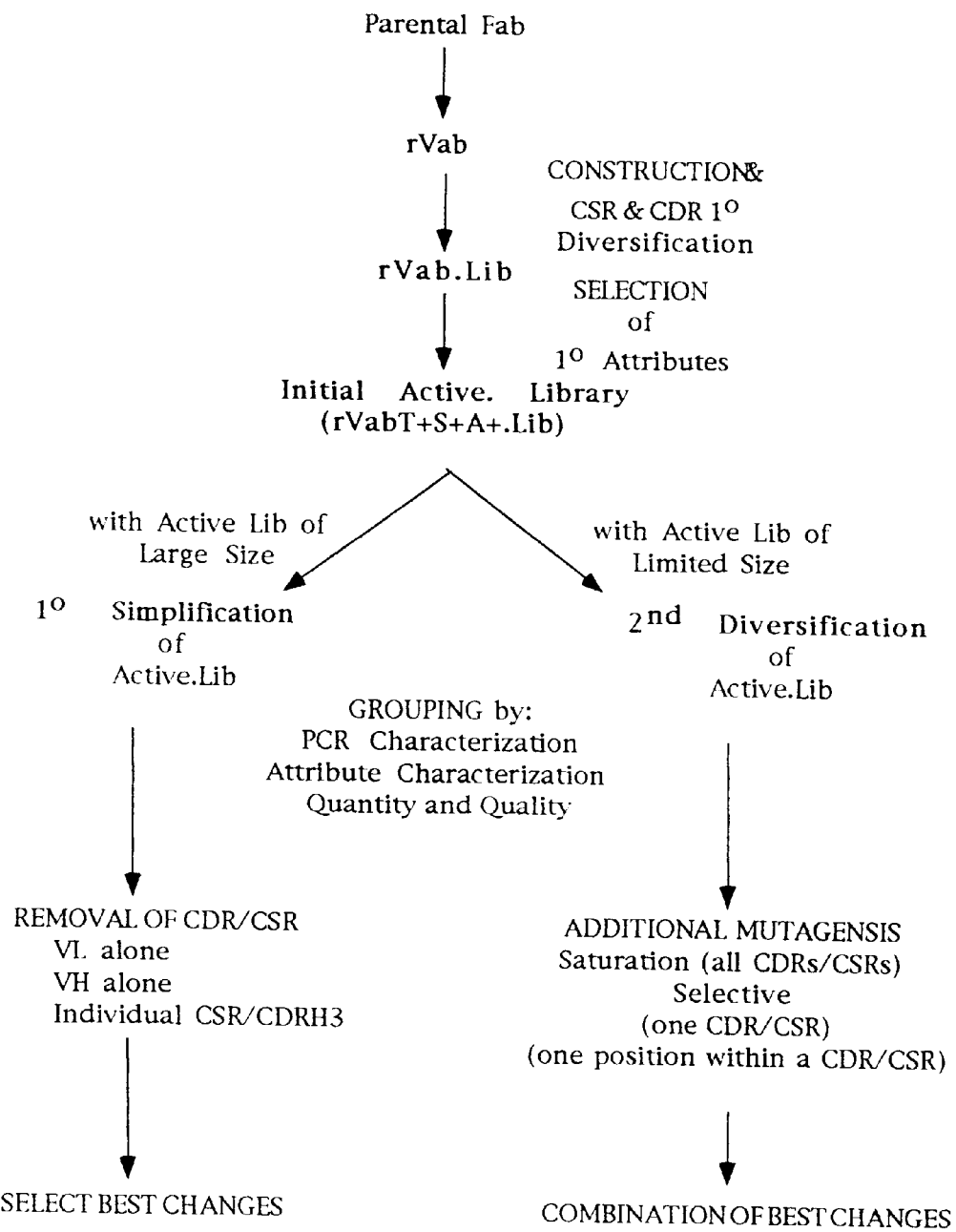
Figure 17:
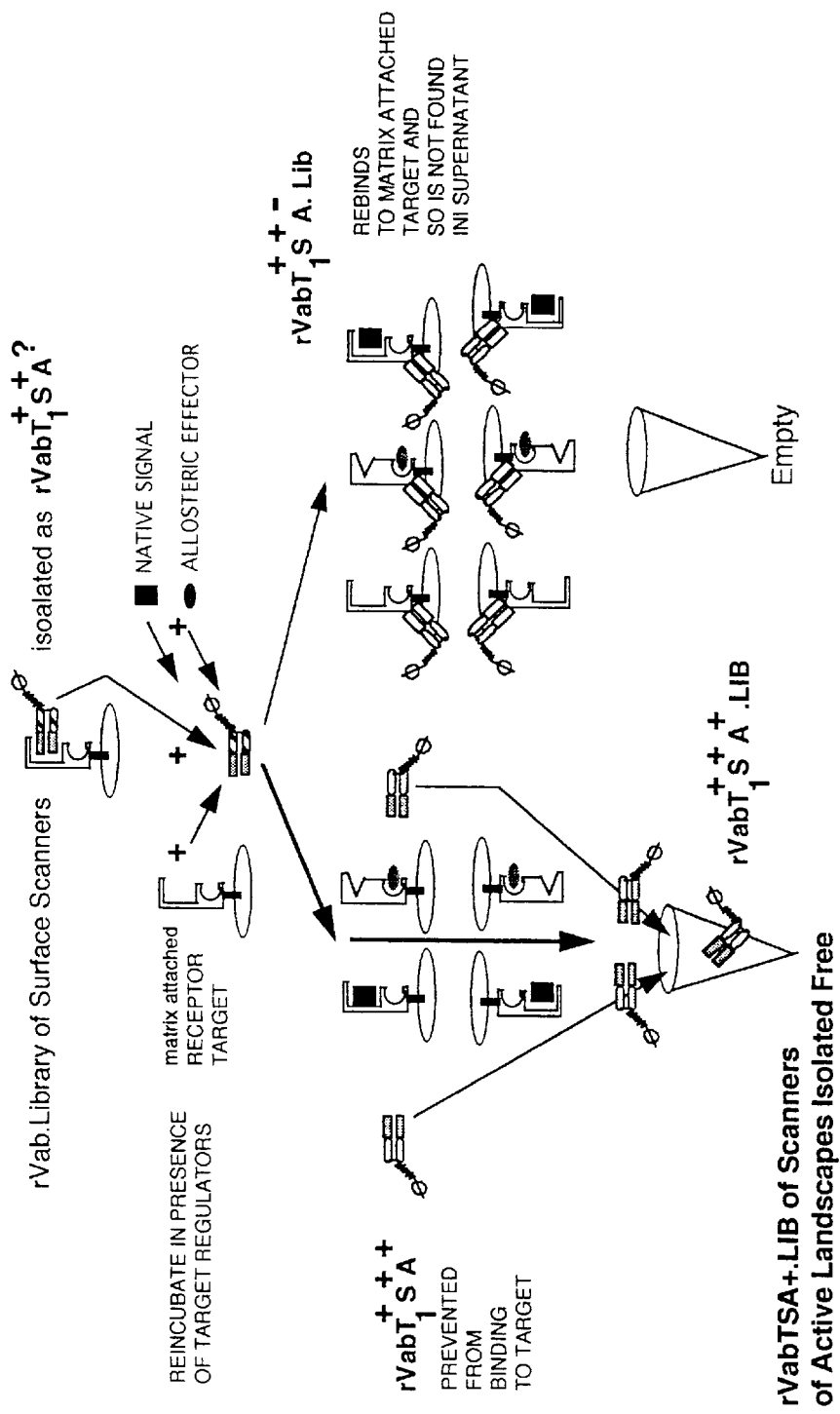

Additional diversification of TSA+ rVabs within CSRs and CDRH3 is carried out by PCR (as detailed in the construction of the original rVab.lib) in Phase IVb whenever the number of rVab within a group is less than 10 or when sufficient information is not obtainable from the number of A+ rVab's identified to develop BEEPS with the desired usefulness for identifying SOMERs and simplification of the TSA+ population is done when the number of rVab within a group is >100 (FIG. 15)

EXAMPLE 3

This example outlines the TSA process establishing simple competitive binding assays for multimeric small organic molecules, which in this example are DISOMERs, capable of regulating the activity of growth hormone receptor. Here, DISOMER discovery is based on the discovery of pairs of rVab which identify active surfaces on Growth Hormone Receptor and their conversion to rVab.REPORTERs according to the method of the invention.

This methodology establishes a generic approach for discovery of drugs active at oligomeric receptor targets, or targets requiring activation at multiple sites of a monomeric unit. In such systems the "receptor" is defined by multiple surfaces which must be in contact with the signal to cause activation.

The process of this invention provides a means of identifying active ligands for multiple site receptors a) which have more than one active surface; b) more than one subunit per active receptor complex; or c) different subunits and active surfaces. This method is also suitable where more than one subunit contains a portion of an active surface; the surface required for activation is too large to be occupied by a single small organic molecule present: within a CHEMFILE; and activation of oligomeric receptors is intimately associated with the hormone induced formation of complexes of at least two receptor subunits (Cunningham, 1991; Kelly, 1991; DeVos, 1992; and Wells, 1993).

Unlike standard screens to identify a single chemical entity to replace a large multi-site binding hormone, the approach described according to this invention, identifies pairs of active surfaces, finds SOMERs for each individual active surface, and then links the SOMERS together to create multimeric units (e.g.,DISOMER) large enough to replace the multivalent hormone, e.g., growth hormone (GH). In the example provided, the target oligomeric receptor is the homo-dimeric growth hormone receptor (GHR) and the active surfaces identified are the two surfaces used by GH for active GHR dimerization. For GHR there is only one type of receptor subunit, referred to here as T1. Activation of the receptor requires GH to dimerize two receptor subunits (T1$^2$) by maintaining binding of active surfaces on two T1.

1. Identification and Isolation of rVabs Specific for GHR

Step 1a: Identification of GHRT+rVab.lib for the T1 GHR Subunits

Isolate from the rVab.lib the subpopulation which binds to the surfaces of the T1 GHR subunit. These rVabs are designated GHR.T+rVab.lib.

Library surface scanners are provided by the rVab.lib constructed as outlined in Example 1 of this invention. This rVab.lib, i.e., rVHCH:VLCL complexes, is expressed on phage surfaces attached to the phage gpIII coat protein. A one ml aliquot of phage lysate (>10$^{12}$t.u.) is mixed with GHR receptor subunits (T1) which are prebound to an immolized solid support i.e., agarose bead-type isolation matrix (mat-T1). In this example, the basic GHR subunit (T1) used is that which encompasses only the excellular domain of the hGHR, including hGHR amino acids 1 to 238 (Leung, 1987; Fuh, 1990) with an unpaired penultimate cysteine (Bass, Greene et al. 1990). This form is referred to as sGHR and is expressed in *E. coli* as an extracellularly released soluble protein (Fuh, Mulkerrin et al. 1990). This soluble protein is then purified (Fuh, Mulkerrin et al. 1990) and bound to beads or plastic through its unpaired cysteine (Bass, Greene et al. 1990), or to plastic through an antibody which recognizes the sGHR but does not interfere with GH binding or active GHR dimerization (Fuh, Mulkerrin et al. 1990; Cunningham, Ultsch et al. 1991). All forms of sGHR bind GH as does the endogenous membrane associated entact GHR (Leung, 1987; Fuh, 1990). An excess of soluble prolactin receptor (PRLR) as competing peptide (comp-T-peptide) (see FIG. 16) or various mutant hGHR, or PRLR missing either H binding site I or II (Cunningham, 1991; DeVos, 1992; and Rozakis-Adcock, 1992) to compete binding of non-specific rVab binders which have no selectivity for GHR binding is routinely added to the mixture to define rVab specificity. With sGHR attached to 0.2 mg of oxivane polyacrylamide beads (Sigma) the reaction mixtures can be as small as 50 ul beads. The excess of soluble prolactin receptor competes for binding of non-specific rVab binders which have no selectivity for GHR binding. The mixture is incubated for at least 3 hr at 30° C. in buffer A which supports normal GHg and GHR association with one entity displayed as an attached phage coat protein (Bass, Greene et al. 1990) and consists of <50 mM Tris, pH 7.4, 1 mM EDTA50 mM NaCl, 1 mg/ml BSA and 0.02% Tween 20 and washed three (3) times in 30C buffer A. The rVab bound to the matrix associated GHR, in the presence of the excess competing soluble non-GHR related peptide (i.e., the comp-T-pep) is designated the GHRTS+ rVab.lib. The phage are recovered by washing (2x) either in Buffer A with 20 nM hGH or 0.2M glycine (pH2.1) (Bass, Greene et al. 1990) and tittered.

The phage libraries are mixed with *E. coli* (at a multiplicity of infection) of approximately one (1), incubated without shaking for 30 min and then plated in antibiotic media and grown overnight and tittered. The survivors are pooled and grown overnight and frozen as bacterial stocks, in 15% glycerol. An aliquot of the stock is grown up and new phage lysates are made and tittered. This phage population, GHR.TS+rVab recognizes all surfaces on the T1 subunit of GHR. Definition of S+ in this population at this time is not mandatory, and can be omitted, i.e., by not adding prolactin receptor (or any other comp-T-pep) to the original reaction mixture above, if the number of GHR.TS+rVab members obtained in Step 1 which are competed by GH (see below) is less than 100.

An additional phase of V region amino acid diversification within CSRs and/or CDRH3, as per outlined in the Example 1 and summarized in FIG. 15, is performed if greater numbers of GHR.T+ or TS+rVab are desired.

Step 1b: Subdivision of TS+rVab based on GHR Surface Epitope Recognized

1b) Group library members according to common receptor surfaces recognized. Designate groups as GHR(x-y).T+ rVab.lib, where x-y is the amino acid domain of the T1 unit containing the common group epitope (FIG. 16).

Separation according to the receptor surface recognized is accomplished by adding aliquots of TS+rVab to plastic dishes to which have been preabsorbed peptides (obtained commercially) of 10–20 amino acid overlapping amino acid sequences of GHR and those domains containing amino acid sequences known to influence GH binding (i.e., hGHR amino acids 54-68, 171-185, 9 [GHR siteI]); and 116-119 and 8-14 (GHRsiteII) as described (Cunningham, Henner et al. 1990). TS+rVab are incubated with preadsorbed peptides in buffer A (20 mM TrisHCl buffer pH 7.5, 1 mM EDTA, 0.1% bovine serum albumen) for 3 hr at 30° C. The dishes are washed to remove unbound rVabs. Bound rVabs are released from the matrix, tittered and amplified again via infection in *E. coli*. Binding to these overlapping GHR peptides produces a grouping according to primary receptor amino acid sequence and hormone binding. Each of the separate groups are then mixed with soluble matrix-GHR (see step 1a) in buffer A with greater than 100 fold excess GH and incubated 3 hr at 30° C. and centrifuged. The phage in the supernatant are tittered, amplified and further enriched by panning 2–3 additional times for TS+rVabs which do not bind to GHR in the presence of GH. This recycling produces a population of GHR.TS+rVab which bind to a surface of the GHR which is normally occupied by bound GH. Although these steps do not identify and/or subdivide all GHR hormone related epitopes, they divide the original GHRTS+ rVab.lib into workable sized subgroups based on binding to various amino acid sequences and domains involved in GHR recognition. Each group is tittered, amplified, infected into *E. coli* and bacterial stocks and subsequent new phage lysates are prepared. Each group is designated by its amino acid receptor sequence or domain recognized (e.g., amino acid x-y) as follows: GHR.T(x-y)S+rVab.lib. Competition by these rVab for I125hGH binding to sGHR is done in standard binding assays (Spencer, Hammonds et al. 1988) in buffer A with terminated by precipitation by polyethylene glycol 8000, at 4° C. in phosphate buffered saline as described (Leung, 1987). Competition binding to membrane associated GHR is performed under identical conditions and reactions are terminated by filtration and washing.

2. Formation and Identification of Bifunctional Active rVabs Possessing Random Sequences of Amino Acid Step 2a: Preparation and Expression of rVab-Pep Library 2a) Attach a random 8 amino acid peptide library (Pep 8) in frame to the light chain (VLCL) of all members of a rVab library recognizing a common GHR surface (FIG. 11 and 20). Designate these bifunctional surface binder libraries GHR(xy).T+rVab-pep.lib.

Each of the group libraries is genetically engineered to be expressed, in a coupled manner, with a short random peptide of 8 amino acids (pep 8) attached through a short linker (LNKR) to one chain of the rVab (FIG. 11). Attachment can be at different positions on different chains depending upon which Cre-Lox recombination system is used to combine the rVHCH1.lib and rVLCL.lib onto the same piece of DNA when the rVab.lib is made (see FIG. 11 vs. 13). In this example, the rVab.lib is made according to Example 1 (FIG. 11) and attachment of the pep 8 is to the amino terminus of the VL region of the rVLCL.lib (FIGS. 11 and 20). In Example 4 below, the construction of a different rVab.lib where addition to a single pep8 could be made to either the carboxyterminus of the constant domain (CL) of the rVLCL or to the aminoterminus domain of the VH of the rVHCH1 is described (also see FIG. 13).

In this example, attachment is accomplished by using PCR to append the pep8 library to the 5' end of the VL region within the rVLCL members of the GHR.TS+rVab.lib. This reaction uses forward primer CH209-216-Not1FWD and back primer APAEPEP8LNKRBCK (i.e., leader seq.Apa1-$(NNN)_8(GGGGS)_1$VL1-7) (see Primer Table, FIG. 10). These reactions contain an aliquot of bacteria from each GHRT(x-y)S+rVab.lib., Taq polymerase and forward and back primers and are cycled 25 times (94° C. 1 min, 60° C. for 1 min and 72° C. for 2 min). The amplified, appended DNA is purified using Magic PCR PREPS (Promega) and after suspension in water, 1 $\mu$g of the purified DNA is digested with Not1 and Apa1 and ligated using 1200U T4 ligase (Sambrook, Fritsch et al. 1990) to fdrVabpCARRIER (see FIG. 11) precut with Not1 and Apa1. The ligated product, designated fdrVabPEPpCARRIER is isolated with GeneClean and electroporated into *E. coli*. Transformants are grown, tittered and frozen stocks are made. A sufficient number of colonies are picked and sequenced to confirm the presence of the random pep8 library. The bacteria, designated GHRT(x-y).rVab-PEP.lib.bact are then grown and phage are induced for expression with helper phage so that the GHRT(x-y) rVab-pep constructs are displayed on the phage surface attached to gpIII. (see FIG. 20).

With the amino acids of the octapeptide being random at each position, there are greater than $10^{10}$ peptide combinations for each library. Accordingly, with less than about 100 GHR.TS+rVab in each group the combinatorial rVab-pep.lib number is less than $10^{12}$ and is therefore accommodated in a normal phage lysate. If the number of GHR.TS+ rVab is greater than about 100, the random octapeptide library is expressed alone as a fusion protein fused to the gpIII on the surface of fd phage via the same linker ([GGGGS]2) and the octapeptides which recognize GHR surfaces are isolated first by panning over matrix attached GHR complexes. Those phage which stick to the matrix, are isolated, amplified and the oligonucleotide sublibrary encoding the pep8 octapeptides which bind to GHR are excised and amplified with primers containing a leader restriction site (in the BCK primer) and ApaL1 (in the FWD primer). This smaller pep8 oligonucleotide sublibrary, which is T+ (pepT+), is then ligated into the grouped GHR.$TS^{+}$rVab.lib precut at the rs1 site in the VL Lgp111 leader secuence and at Apa 1 (See FIG. 11D) to produce a GHR.TS+rVab-pep(T+) library. In such cases the members of this combinatorial library, less than $10^{14}$, are grown, the phage induced and the library of surface attached GHR.TS+rVab-pep(T+) harvested and tittered.

Step 2b: Identification of Active Bivalent rVab-Pep Members

2b) Isolate GHR(x-y) T+.rVab-pep members which actively (A+) dimerize the receptor as does GH. Label these GHR(x-y)TA+rVab-pep.

The bivalent; rVab-PEP, are expressed as a phage displayed library and are panned for combinatorial members which actively dimerize GHR. The positives are labeled GHR.rVabT(x-y)SA+-pepT1+.lib. In this step, activation is recognized by the occurrence of one or more of the following observable events: 1) dimerization of two GHR T1 subunits; 2) dimerization of two T1 subunits which allow fluorescence transfer between the same or different modified amino acids in the two subunits as described by Cunningham (Cunningham, Ultsch et al. 1991); 3) dimmer formation which generates an antibody recognized epitope which contains amino acids from two T1 subunits which occur only in activated dimeric T1$^2$ structures (Taga, Narazaki et al. 1992); 3) GHR-GH-GHR-matrix complexes which are dissociated by wild type hGH, or only a mutant hGH with only site I or site II binding capability (Cunningham, Ultsch et al. 1991); or 4) antibody recognizable phosphorylation of one of the receptor subunits associated with active receptor dimerization. In the later case, incubation of GHR.rVabT(x-y)S+pep.lib with ATP and PKC is carried out before panning and the ATP and PKC is present during the panning procedures. It is also possible to monitor for in vitro active dimerization by the co-presence of some third GHR associated protein in the active complex (Taga, Narazaki et al. 1992).

2c) Confirm activity by testing for activation of a cell associated C GHR. Those GHR.TSA+rVab-pepT which appear active in vitro, are tested in an intact cell assay system such as GH induced growth of myeloid leukemia cell line FDCP1 expressing hybrid extracellular domain GHR-intracellular granulocyte colony-stimulating factor receptor (GCSFR) (Fuh, Cunningham et al. 1992) or IM-9 cells (Silva, Weber et al. 1993) to confirm the agonist nature of the rVab-pep complex.

3. Identification of Active GH-rVab Pairs for use as Reporters

Step 3a. Expression of Soluble rVabs

3a) Identify from among the members of different A+ rVabA+-pep groups, those which have a rVab which by itself competes with the peptide member of the same or different rVabA+-pep group. This is accomplished by carrying out competition binding assays designed to identify those rVabs and peptides which compete with each other for binding to the GHR. The peptide portion of an active rVab-pep is separately expressed without the corresponding rVab to perform these binding assays. By this process rVabs which can mimic and replace the pep8 portion of an active rVab-pep member are identified. The rVab of a first A+rVab-pep member and the rVab of a second A+rVab-pep member which competes with the peptide portion of the first member, are designated an active pair of GH-rVabs.

Specifically, after confirmation of activation is obtained, the active rVab-pep are modified by appropriate digestion of the construct to allow expression of soluble rVab without any linkage to phage coat protein gpIII and to the octapeptic e as well. Such simplified entities are labeled rVabTS+A*. To prepare the modified constructs allowing for expression of free soluble rVab, DNA from rVab-pep is obtained, digested with Apa1 and Not1 and isolated. One μg of the isolated DNA is then ligated with 5 μg pEXPRESSIONrVab DNA precut with ApaL1 and Not1 by incubation with T4 ligagse. The ligated products are isolated by GeneClean II and electroporated into E. coli and transformants obtained and confirmed by diagnostic PCR and sequencing. Frozen stocks are prepared. These stocks are denoted GHR.rVabTS+A* and not A+ because by themselves they cannot activate the GHR but are members of active pairs (i.e., rVabs and pep8s) which do activate the receptor. Expression of the octapeptide member of the active rVab-pep is carried out by excision and ligation of the oliognucleotide portions encoding the pep8 and transfer to expression vectors in which the pep8 is expressed as a soluble extracellular entity fused with a easily purifiable tagged carrier protein (using a variety of commercially available expression vectors) or attached via GGGGS linker to gpIII coat protein and displayed as a phage surface entity. These entities are labelled pep8A* and are used as described below to identify rVab for the other portion of the GHR active surface utilized by the active rVab-pep entity.

3b) rVab and pep8 members of active pairs are grouped according to common GHR surfaces recognized (as described above).

4. Preparation of GH-rVab-Reporters

Convert a rVab representative of at least one active pair of GH-rVabs into a GH.rVab-Reporter.

The CH domain of the heavy chain of the rVab is labelled (as described in Example 2) and the labelled entity, designated GH.rVab-REPORTER, is used to establish saturation and competition binding assays as described in Example 2.

The isolated and expressed separated pep8 members from active rVabA+-pep constructs are used in standard binding competition assays to identify (see FIG. 11) those GHRrVabT+ which bind to the same GHR domain as the pep8 entities. Those which compete are designated as the second member of the active pair of rVab for the two active GHR surfaces required for receptor activation. This second member is then converted to a rVab-Reporter (see above). The rVab member of the rVabA+-pep construct from which the pep8 was obtained is the second member of the active pair.

Step 5: SOMER SCREENING

Establish binding assays with each member of an active pair of GH.rVab-REPORTERs for a pair of SOMERS, each capable of binding to at least one of the two domains of an active pair of receptor surfaces involved in active GHR dimerization.

Figure 21:
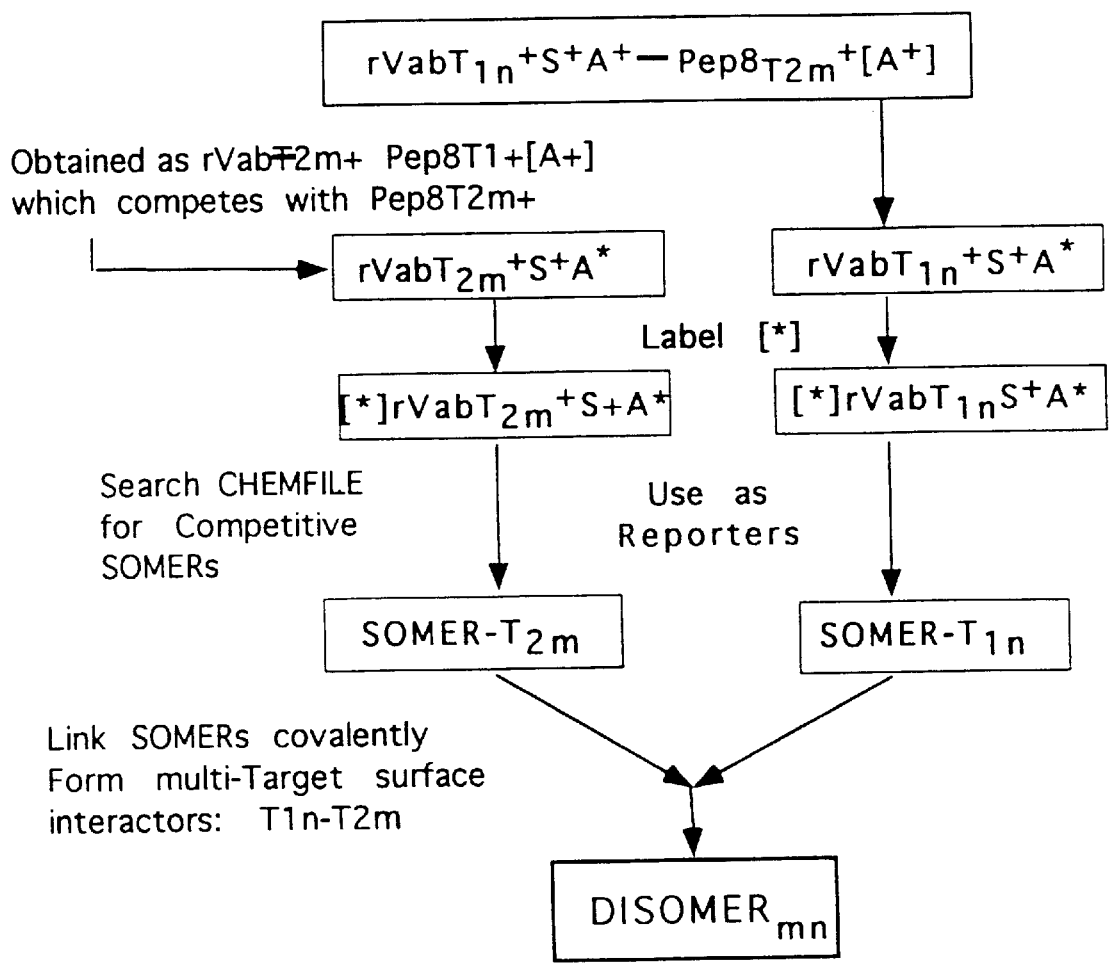
Figure 22:
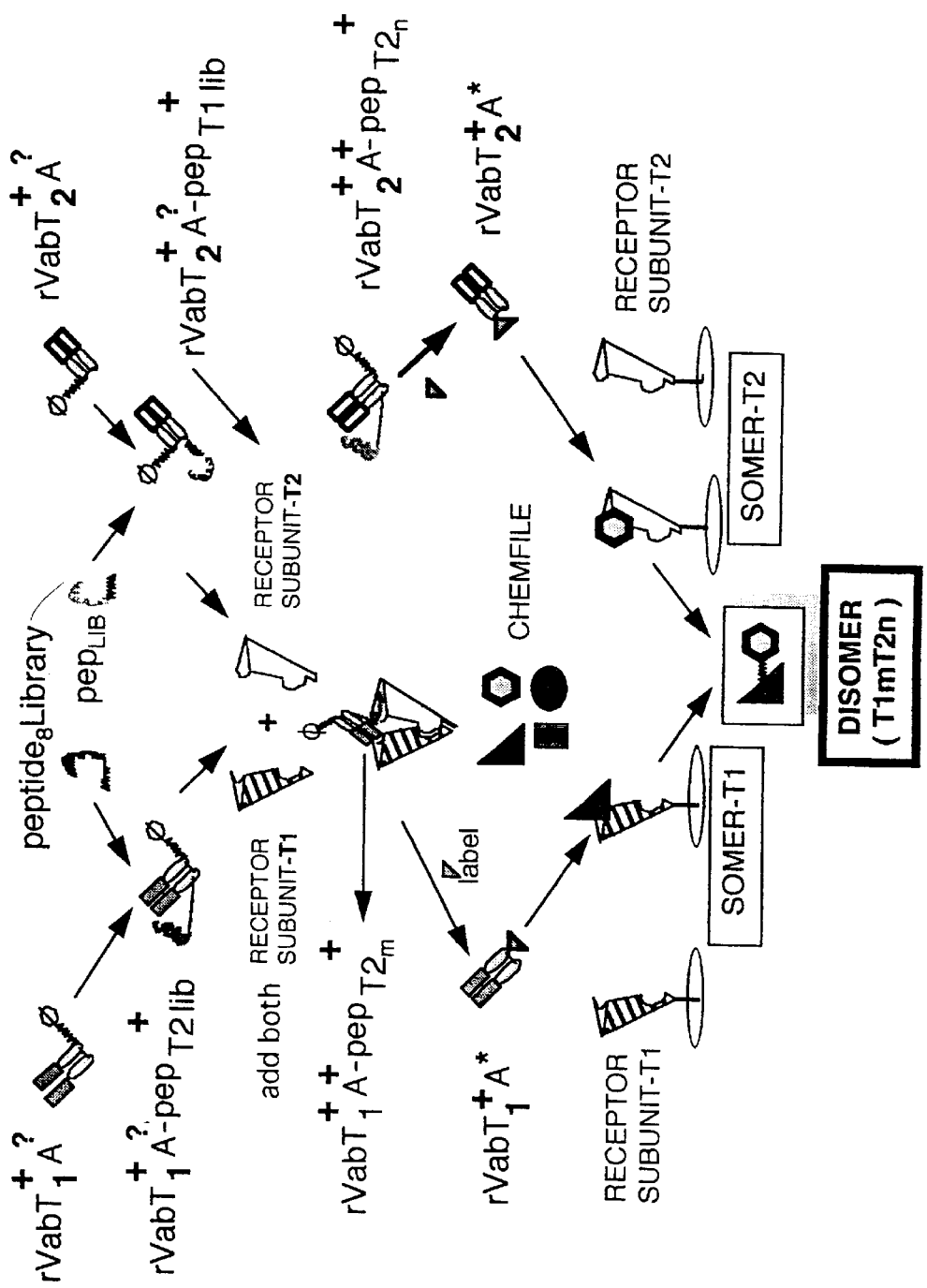

The GH.rVab-REPORTER is used under standardized and automated binding assay conditions to identify SOMERs within a chemical data base (i.e., CHEMFILE) which will compete at an active* (A*) surface on the T1 subunit of the GH receptor. These SOMERs are designated SOMER-T1. In a parallel fashion, using the other rVab-Reporter member of the active rVab pair (as defined above) SOMERs are isolated for the second active surface on GHR required for its activation (FIGS. 21 and 22). The SOMERs which recognize the second site are designated SOMER-T1.

Identification of specific interaction with site I (i.e., T1) or site II (i.e., T1') of huGHR is made in binding assays measuring the ability of these entities to compete with mutant 125I-GH which can only bind to site I or II as described (Cunningham, Ultsch et al. 1991).

Step 6: DISOMER Preparation and Identification of Drug Leads

In the last step of this process, SOMER-T1 and SOMER-T1' are covalently combined to create a bivalent SOMER (i.e., a DISOMER) which can recognize the two sites of the active surface pair, i.e., the T1 and T1' receptor dimmer subunit active surfaces. This DISOMER can actively dimerize the GH receptor subunits as does the native hormone. Confirmation of DISOMER GH activity is obtained in standard radioreceptor binding assays (competitive with intact labelled (GH) for GHR binding and standard activity assays (in vitro and/or GHR cellular activation systems). Additional assay systems for active hormone receptor subunit oligomerizations in which a free excellular receptor-:hormone complex associates with other membrane proteins in intact cells to form active oligomeric complexes which direct auto-, and substrate phosphorylation, and other down stream activation responses (Taga, Narazaki et al. 1992).

Figure 20:
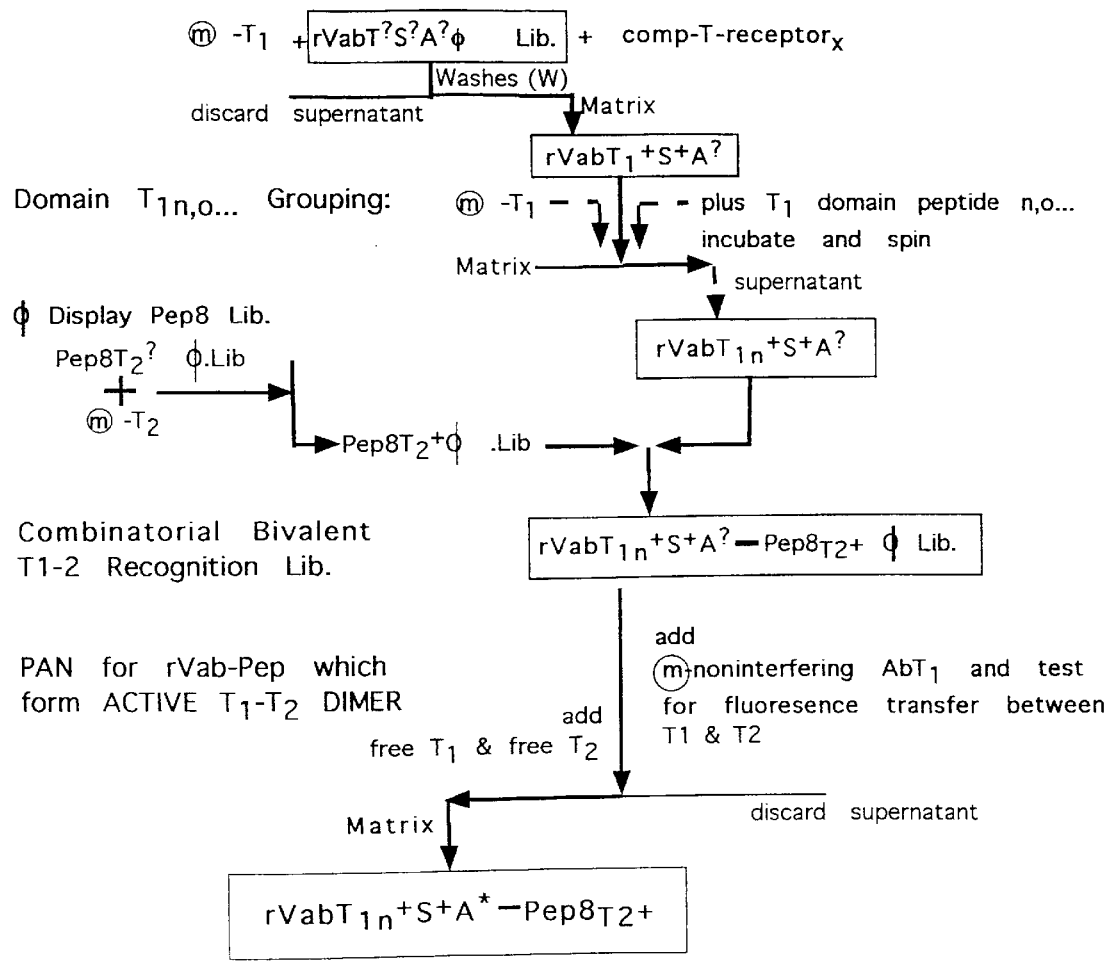

Steps 1–4 of the process, which find active surface landscapes involved in active dimerization of two TI subunits of GHR are outlined in FIGS. 20, 21 and 22. FIG. 20 is a flow diagram for creation of rVab-pep. libraries and isolation of rVab-peptides for the two active GHR surfaces. In the example presented here of oligomeric receptor targets, there is only one type of subunit (T1) in the active GHR dimer complex, and therefore subunit T2=T1. FIGS. 21, 22 illustrate GHT1- and GHT1'-SOMER and GH-DISOMER (i.e., GHT1-GHT1') identification.

EXAMPLE 4

Example 4 is a variation of Example 3 which recognizes the fact that many hormonal receptors are comprised of different receptor subunits. Often at least two or three subunits which may all be different from each other are required for activity. In these cases, hormone induced receptor oligomerization associated with receptor activation, requires interaction of the hormone with at least three active surfaces, each being on a different receptor subunit. Examples of heterodimeric (alpha/beta, or alpha/gamma) receptors include the group of interleukin (IL) IL3, IL4, IL5, IL7, IL9 receptors and the GMCSF receptor, and the group of growth factor FGF, PDGF, CSF and NGF receptors, while an example of a heterotrimeric receptors (alpha, beta and gamma) is the IL2 receptor (see reviews Pierce, 1989; Boulay, 1993; Cosman, 1993; Kishimoto, 1994; Kaushansky, 1993; Kondo, 1994; Noguchi, 1993; Russell, 1993 and Bamborough, 1994).

The use of rVab to identify active surfaces involving two or more site's distributed on multiple subunits involves certain adaptions from the process used when activation requires only one site. First, with the heterooligomeric receptors, a different rVabT(x)S+ lib is identified for each subunit (x) using the soluble receptor subunits as initial targets (e.g. Tavernier, 1991), as Second, that for trimeric receptors two random peptide 8 libraries are attached to each rVabT(x)S+ library. Third, where the rVab is T+ for the alpha receptor subunit (i.e., rVabT+S), the other two members of the active trio (i.e., those binding to each of the other two subunit surfaces necessary for active receptor trimerization), designated rVabT+ and rVabT+, are identified as those which compete for binding with one of the two octapeptide members of an active rVabTSA+-pep$^2$. For such trimeric receptors, the individual rVHCH.lib and rVLCL.lib made in Example 1 are combined into different fdRECEIVERs and pUC19PROVIDERs as detailed in FIG. 13.

Figure 13A:
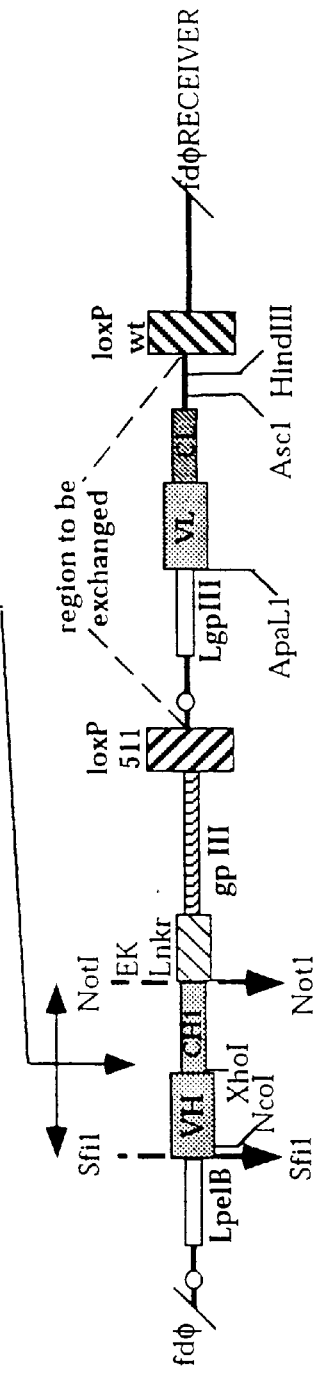
Figure 13B:
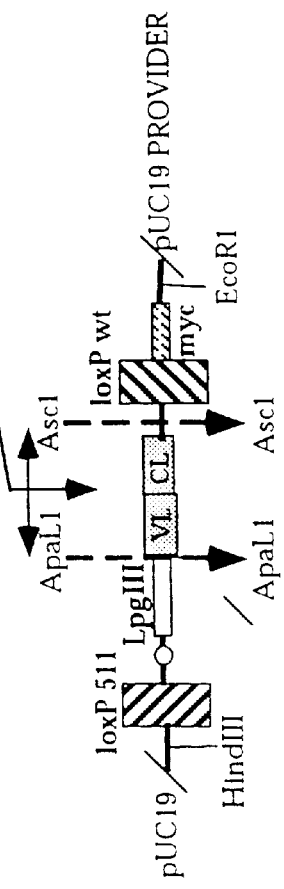
Figures 13C, 13D, 13E:
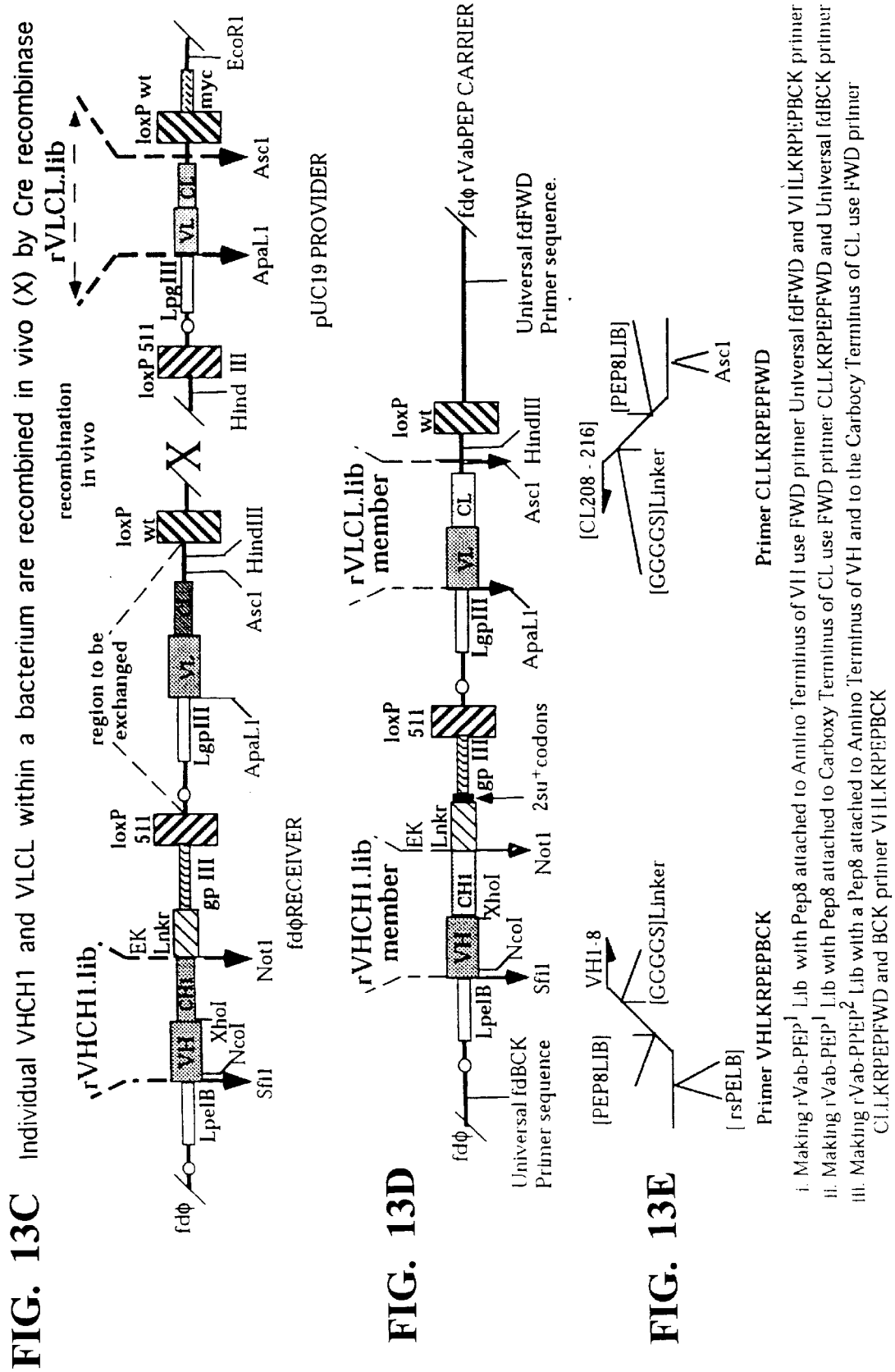

In this application, rVHCH.lib is placed into a fdRECEIVER which allows expression of rVHCH fused to gpIII coat protein and with, or without, peptide (preferably 8 amino acids) attached to its aminoterminus. The rVLCL.lib is placed into a pUCPROVIDER which allows for expression of rVLCL as soluble entities with, or without, peptide, preferably 8 amino acids, attached to its CL domain. After in vivo Cre-Lox -recombination of these two libraries, as detailed in Example 1, (see also. FIG. 13) the product rVab.lib is cloned as a single fdDNA designated fdrVabPEP-CARRIER. rVab members which bind to each of the receptor subunits (i.e., Tx+rVab) are then isolated and grouped as described in Example 3. Subsequent addition of one or two random octapeptide libraries (Pep 8'''), which in some cases have been prescreened and selected for binding to an identified receptor subunit is accomplished via PCR. As described above and in FIG. 13, oligonucleotides encoding the peptides are added to the DNA encoding the rVab library using FWD primer CLLNKPEPFWD (Asc1-(NNN)8 (GGGGS)3CLL208-216) and VHLNKPEPBCK (rsPELB-(NNN)8(GGGGS) VH1-8) together or in combination with primers having no Pep8 or linker- appending sequences. Use of one of these primers with a primer devoid of a Pep8 library could be used to generate a rVab with one attached pep8 (i.e., rVab-Pep $8^1$) as described above in Example 2 with the single Pep 8 library appended through linker to the either the aminoterminus of the rVHCH1 member or the carboxyterminus of the rVLCL member (FIG. 13). According to this process, each attached peptide and the rVab portion of the rVab-PEP$^2$ each bind to a specific target site. Binding to all three sites is required for activity of the receptor. Therefore, the trimeric rVab-PEP$^2$ unit defines three binding domains: one defined by the rVab portion ((T(x)), and one each by each of the pep8 (i.e., pep8$^1$ and pep8 $^2$) present in the construct.

Isolation of active rVab-Pep$^2$ members utilizes enrichment cycles in which all three receptor units are complexed together in active trimeric structures. Such structures, complexed with their phage expressed rVab-Pep$^2$ entities, are enriched by use of matrix-bound active subunits, antibodies to each of the three units, antibodies to modifications of receptor units which occur upon active oligomerization, such as phosphorylation or association with additional non-receptor membrane components (Argetsinger, Campbell et al. 1993; Silvennoinen, Witthuhn et al. 1993; and Witthuhn, 1993). Confirmation of agonist and antagonist activity is done using standard hormone: receptor binding assays to establish competitive binding of hormone to its receptor (Kitamura, Sato et al. 1991; Imler and Zurawski 1992; Pietzho, Zohlnhofer et al. 1993) and cellular receptor dependent activity assays measuring growth, DNA synthesis, protein phosphorylation etc. (Yokota, Otsuki et al. 1986; Pierce, Ruggiero et al. 1988; Solari et al. 1989; Anklesaria, Teixido et al. 1990; Heidaran, Pierce et al. 1990; Pierce, Di et al. 1990; Heidaran, Pierce et al. 1991; Keegan, Pierce et al. 1991; Murakami, Narazaki et al. 1991; Kruse, Tony, et al. 1992; Otani, Siegel et al. 1992; Taga, Narazaki et al. 1992; and Wang, Ogorochi et al. 1992).

For a given rVab-Pep8$^2$ we identify rVabA*s which are contained in other rVab-Pep8$^2$A+ which bind to each of the target sites bound by the peptides of the original active rVab-Pep8$^2$ (trimer rVabA* unit), following the same process outlined in Example 3. Using this process, members of the trimeric unit are identified as a) any rVabT+ from another active construct (i.e., rVabTSA+-Pep8$^2$) which competes with one of the two PEP lib on the original active rVabTSA+-PEP$^2$, b) with any rVabT+ from a third active construct (i.e., rVabTSA+-Pep8$^2$) which competes with the other PEP on the original active rVabTSA+-PEP$^2$ and c) the rVabTS+ of the original active rVabTS+-PEP$^2$. Competition for binding to GHR is determined by assaying for competition of PEP8 units expressed either attached to gpIII coat protein and presented as phage displayed entities or as soluble fusion proteins with labelled rVabTx+-Reporters which are made as described above in example 2 and 3. After identification of all three of the active trimer members, each rVab member of the active timeric unit is then cloned minus its Pep8library member(s), expressed, isolated and converted to a rVab-REPORTER, as detailed in Example 1, and used to establish competitive binding assays which then find competing SOMERs (i.e., Somer-$T_1$, $T_2$ or $T_3$). In the final stage covalent linking of the three Somer-Ts) is done so as to construct the active multimer, in this case a TRISOMER (i.e., $T_1$-$T_2$-$T_3$), substitute for the native hormone. In these systems, an additional receptor activation assay system is available for heterooligomeric receptor activation which monitors the induction of identifiable holoreceptor induced cellular responses by preformed soluble complexes of hormone and one of the receptor subunits in response to the binding of these complexes to intact cells expressing the other subunit(s) of the active receptor complex and formation of active holoreceptor complexes (Taga, Hibi et al. 1989).

In these systems, an additional receptor activation assay system may be used to confirm heterooligomeric receptor activation. Such systems monitor the induction of identifiable cellular responses induced by the combination of preformed soluble complexes comprising hormone and one of the receptor subunits and intact cells expressing the other subunit(s) of the active receptor complex and the subsequent formation of active complete holoreceptor complexes (Taga, Hibi et al. 1989).

The following Table lists exemplary ligands and heterooligomeric receptor systems for which this invention provides a means for identifying their pharmacologic target sites as well as SOMERS or DISOMERS.

| | | |
|---|---|---|
| Interleukin1 | Immune System Supression/Stimulation | Agonist/Antagonist |
| 1L2-7, 9-11 | Immune System Supression/Stimulation | Agonist/Antagonist |
| Insulin Like Growth Factors: | Neoplasias | Antagonist |
| | Erythropoiesis | Agonist (synergistic w Epo) |
| | Granulopoiesis | Agonist (synergistic w GMSCF) |
| TGFbetas | Wound Healing (Matrix proteins) | Agonist |
| | Inflammation | Antagonist |
| | Carciogenesis | Antagonist |
| | AutoImmune Disease | Antagonist |
| GCSF | Chemotherapy | Agonist |
| | Bone Marrow Transplation | Agonist |
| CSF | Bone Marrow Failure Syndromes (re: radiation/chemotherapy) | Agonist |
| | Inflammatory | Antagonist |
| | Neoplasms (acute myeloid leukemia) | Antagonist |
| Erythropoietin | Hematopoiesis (anemias) | Agonist |
| GMCSF | Immune Suppression/Stimulation | Agonist/Antagonist |
| PDGF | Wound Repair | Agonist |
| | Angiogenesis | Antagonist |
| | Vasoconstriction | Antagonist |
| | Atherosclerosis | Antagonist |
| | Neoplasms | Antagonist |
| | Pulmonary Fibrosis | Antagonist |
| | Inflammatory Joint Diseases | Antagonist |
| EGF | Wound Repair | Agonist |
| | Neoplasms | Antagonist |
| FGF | Neoplasms | Antagonist |
| | Wound Repair | Agonist |
| | Angiogenesis (Capillary Blood Vessels) | Antagonist |
| NGF | AntiNeurodegenerative Diseases (Acute/Chronic); (Peripheral/Central) | Agonist |
| Small Organic Molecules | Neurotransmitters i.e. Cholinomimetics (ACh @ mReceptor 1-5) | Agonist/Antagonist |
| | Transporter/Channel Regulators | Agonist/Antagonist |

References

Andre, C., et al. (1987). "Immunochemical studies of the muscarinic acetylcholine receptor." *J Recept Res* 7(1–4): 89–103.

Andrews, P. R., Craik, D. J., Martin, J. L., (1984). Functional group contributions to drug receptor interactions. J. Med. Chem. 27:1648–1657.

Anklesaria, P., et al. (1990). "Cell-cell adhesion mediated by binding of membrane-anchored transforming growth factor alpha to epidermal growth factor receptors promotes cell proliferation." *Proc Natl Acad Sci USA* 87 (9): 3289–93.

Appleyard, R. K. (1954). Genetics 39: 440–452.

Argetsinger, L. S., et al. (1993). "Identification of JAK2 as a growth hormone receptor-associated tyrosine kinase." *Cell* 74(2): 237–44.

Bachar, O., Fisher, D., Nussinov, R., Wolfson, H. J. (1993). A computer vision based technique for 3-D sequence independent structural comparison of proteins. Protein Eng. in press.

Bamborough, P., et al. (1994). "The interleukin-2 and interleukin-4 receptors studied by molecular modelling." *Curr.Biol.* 2: 839–851.

Barbos, C. F., Kang, A. S., Lerner, R. A. and Benkovic, S. J. (1991). "Assembly of combinatorial antibody libraries on phage surfaces: the gene III site." *Proc. Natl. Acad. Sci. USA* 88:7978–7982.

Bass, S., et al. (1990). "Hormone phage: an enrichment method for variant proteins with altered binding properties." *Proteins* 8(4): 309–14.

Berrie, C. P., et al. (1985). *BioChem Soc. Trans.* 13: 1101–1103.

Beth, A. (1993). *Life Sci.* 52: 429–432.

Bird, R. E., Hardman, K. D., Jacobson, J. W., Johnson, S., Kauifman, B. M., Lee, S. M. Lee, T., Pope, S. H., Riordan, G. S. and Whitlow, M. (1988). "Single-chain antigen-binding proteins." *Sci.* 242:423–426.

Boulay, J. L. and W. E. Paul (1993). "Hematopoietin sub-family classification based on size, gene organization and sequence homology.[Review]." *Curr. Biol.* 3: 573–581.

Breitling, S. D., Seehaus, T., Klewinghaus, I. and Little, M. (1991). "A surface expression vector for antibody screening." *Gene* 104:147–153.

Brooks, B. R., Bruccoleri, R. E., Olafson, B. D., States, D. J., Swaminathan, S., Karplus, M., (1993). CHARMM: A program for macromolecular energy, minimization and dynamics calculation. J. Comp. Chem. 4:187–217.

Bruccoleri, R. E., Karplus, M., (1987). Prediction of the folding of short polypeptide segments by uniform conformational sampling. Biopolymers, 26:137–168.

Buckley, N. J., et al. (1989). "Antagonist binding properties of five cloned muscarinic receptors expressed in CHO-K1 cells." *Mol Pharmacol* 35 (4): 469–76.

Buckley, N. J., et al. (1990). "Use of clonal cell lines in the analysis of neurotransmitter receptor mechanisms and function [Review]." *Biochim Biophys Acta* 1055(1): 43–53.

Burton, D. R., Barbas, C. R., Persson, M. A. A., Liening, S., Chanock, R. M. and Lerner, R. A. (1988). "A large array of human monoclonal antibodies to type 1 human immunodeficiency virus from combinatorial libraries of asymptomatic seropositive individuals." *Proc. Natl. Acad. Sci. USA* 88:10134–10137.

Cabilly, S., Riggs, A. D., Pande, H., Shively, J. E., Holmes, W. E., Rey, M., Perry, L. J., Wetzel, R., Heyneker, H. L. (1984). "Generation of antibody activity from immunoglobulin polypeptide chains produced in *Escherichia coli.*" *Proc. Natl. Acad. Sci. US* 81:3273–3277A.

Chothia, C. and A. M. Lesk (1987). "Canonical structures for the hypervariable regions of immunoglobulins." *Journal of Molecular Biology* 196(4): 901–17.

Chothia, C., et al. (1992). "Structural repertoire of the human VH segments." *J Mol Biol* 227(3): 799–817.

Chothia, C., et al. (1989). "Conformations of immunoglobulin hypervariable regions [see comments]. [Review]." *Nature* 342(6252): 877–83.

Clackson, T., Hoogenboom, H. R., Griffiths, A. D. and Winter, G. (1991). *Nature* 352:624–628.

Clackson, T. and Wells, J. A. (1995). A Hot Spot of Binding Energy in a Hormone Receptor Interface Science 267:383–386.

Claesson-Welsh, L. (1995). "Platelet-derived Growth Factor receptor Signals." *J. Biol. Chem.* 269:32023–32026.

Cosman, D. (1993). "The hematopoietin receptor superfamily. [Review]." Cytokine 5(2): 95–106.

Cox, J. P. L., Tomlinson, I. M. and Winter, G., (1994). "A directory of human germ-line V kappa segments reveals a strong bias in their usage." *Eur. J. Immunol.* 24:827–836.

Cunningham, B. C. and J. A. Wells (1989). "High-resolution epitope mapping of hGH-receptor interactions by alanine-scanning mutagenesis." *Science* 244(4908): 1081–5.

Cunningham, B. C., et al. (1990). "Zinc mediation of the binding of human growth hormone to the human prolactin receptor." Science 250(4988): 1709–12.

Cunningham, B. C., et al. (1990). "Engineering human prolactin to bind to the human growth hormone receptor." *Science:*247(4949 Pt 1): 1461–1465.

Cunningham, B. C., et al. (1991). "Dimerization of the extracellular domain of the human growth hormone receptor by a single hormone molecule." *Science* 254 (5033): 821–5.

Cwirla, S. E., Peters, E. A., Barrett, R. W., and Dower, W. J. (1990). "Peptides on phage: a vast library of peptides for identifying ligands." *Proc. Natl. Acad. Sci. USA*, 87:6378–6382.

DeFronzo, R. A. Bonadonna, R. C. and Ferrannini, E. (1992). *Diabetes Care* 15:318–368.

Delvin, J. J., Panganiban, L. C., and Devlin, P. E., (1990). "Random Peptide Libraries: A Source of Specific Protein Binding Molecules." *Science* 249:404–406.

DeVos, A. M., et al. (1992). "Human growth hormone and extracellular domain of its receptor: crystal structure of the complex." *Science* 255(5042): 306–12.

Dower, W. J., et al. (1988). "High efficiency transformation of *E. coli* by high voltage electroporation." *Nucleic Acids Research* 16(13): 6127–45.

Elber, R., Karplus, M. (1990). Enhanced Sampling in molecular dynamics: Use of the time-dependent Hartree approximation for a simulation of carbon monoxide diffusion through my myoglobin. *J. Am. Chem. Soc.* 112:9161–9175.

Figini, M., Marks, J. D., Winter, G. and Griffiths, A. D. (1994). "In Vitro Assembly of Repertoires of Antibody Chains on the Surface of Phage by Renaturation." *J. Mol. Biol.* 239:68–78.

Fisher, D., Bachar, O., Nussinov, R., Wolfson, H. J. (1992). An efficient automated computer vision based technique for detection of three dimensional structural motifs in proteins. J. Biomolec. Struct. Dyn. 9(4): 769–789.

Fisher, D. R., Norel, R. H., Wolfson, and Nussinov, R., (1994). Surface motifs by a Computer Vision Technique: Searches, Detection and Implications for Protein Ligand Recognition, Protein: Structure, Function and Genetics, 16:278–292.

Florio, V. A. and P. C. Sternweis (1985). "Reconstitution of resolved muscarinic cholinergic receptors with purified GTP-binding proteins." *J. Biol. Chem.* 260(6): 3477–83.

Folch, J., et al. (1957). *J. Bio. Chem.*

Fraser, C. M., et al. (1989). "Site-directed mutagenesis of ml muscarinic acetylcholine receptors: conserved aspartic acids play important roles in receptor function." *Mol Pharmacol* 36(6): 840–7.

Fuh, G., et al. (1992). "Rational design of potent antagonists to the human growth hormone receptor." *Science* 256(5064): 1677–80.

Fuh, G., et al. (1990). "The human growth hormone receptor. Secretion from *Escherichia coli* and disulfide bonding pattern of the extracellular binding domain." *J. Biol. Chem.* 265(6): 3111–5.

Garrard, L. J., Yang, M., O'Connell, M. P., Kelly, R. F. and Henner, D. J. (1991). "Fab assembly and enrichment in a monovalent phage display system." *Bio/Technology* 9:1373–1377.

Garrett, K. M., Blume, A. J. and M. S. Abel (1989). "Effect of halide ions on [$^{35}$S]TBPS binding to Gaba-A Receptors." *J. Neurochemistry* 53:935–939.

Garrett, K. M., Abel, M. S. and A. J. Blume (1989). "Effects of various GABA-A Receptor Modulators on [$^{35}$S] TBPS binding in the presence of various halindes." *J. Neurochemistry* 53:940–945.

Gibson, T. J. (1984). University of Cambaridge, UK.

Goldberg, D. E. (1989). Genetic Algorithms in Search, Optimization and Machine Learning Addison-Welsey Publishing Co.

Goodford, P. J., (1985). A computational procedure for determining energetically favorable binding sites on biologically important macromolecules. J. Med. Chem. 28:849–857.

Goodsell, D. S., Olson, A. J. (1990). Automated docking of substrates to proteins by simulated annealing Proteins 8:195–202.

Griffiths, A. D., et al. (1994). "Isolation of high affinity human antibodies directly from synthetic repertoires." *EMBO* 13(14): 3245–3260.

Habecker, B. A., et al. (1993). "Regulation of Expression and Function of Muscarinic Receptors." *Life Sciences* 52: 429–432.

Haga, K. and T. Haga (1983). "Affinity chromatography of the muscarinic acetylcholine receptor." *J. Biol. Chem.* 258(22): 13575–9.

Haga, K., et al. (1986). "Reconstitution of the muscarinic acetylcholine receptor. Guanine nucleotide-sensitive high affinity binding of agonists to purified muscarinic receptors reconstituted with GTP-binding proteins (Gi and Go)." *J. Biol. Chem.* 261(22): 10133–40.

Hakwins, R. E. and Winter, G. (1992). "Cell selection strategies for making antibodies from variable gene libraries: trapping the memory pool." *Eur. J. Immunol.* 22:867–870.

Heidaran, M. A., et al. (1990). "Chimeric alpha- and beta-platelet-derived growth factor (PDGF) receptors define three immunoglobulin-like domains of the alpha-PDGF receptor that determine PDGF-AA binding specificity." *J. Biol. Chem.* 265(31): 18741–4.

Heidaran, M. A., et al. (1991). "Role of alpha beta receptor heterocimer formation in beta platelet-derived growth factor (PDGF) receptor activation by PDGF-AB." *J. Biol. Chem.* 266(30): 20232–7.

Hoess, R. H., et al. (1986). "The role of the loxP spacer region in P1 site-specific recombination." *Nucleic Acis Res.* 14: 2287–2300.

Hoess, R. H., et al. (1982). "P1 site-specific recombination: nicleotide sequence of the recombining sites." Proceedings of the *National Academy of Sciences of the United States of America* 79(11): 3398–402.

Holland, J. H., (1992). *Adaption in Natural and Artificial Systems*. The MIT Press, Cambridge, Mass.

Holliger, P., Prespero, T. and Winter, G. (1993). "Diabodies": Small bivalent and bispecific antibody fragments." *Proc. Natl. Acad. Sci. USA* 90:6444–6448.

Hoggenboom, J. R., Griffiths, A. D., Johnson, K. S., Chiswell, D. J., Hudson, P., and Winter, G. (1991). "Multisubunit proteins on the surface of filamentous phage: methodologies for displaying antibody (Fab) heavy and light chains." *Nucleic Acid. Res.* 19:4133–4137.

Hoogenboom, H. R. et al. (1991), *Nucleic Acid Res.* 4133–4137; Jespers, L. S., Roberts, A., Mahler, S. M., Winter, G. and Hoogenboom, J. R. (1994). "Guiding the selection of human antibodies from phage display repertoires to a single epitope of an antigen." *Bio/Technology* 2:899–903.

Hoogenboom, H. R., Marks, J. D., Griffiths, A. D., and Winter, G. (1992). "Building antibodies from their genes." *Immunol. Rev.* 130:41–68.

Horton, R. M., et al. (1989). "Engineering hybrid genes without the use of restriction enzymes: gene splicing by overlap extension." *Gene* 77 (1): 61–8.

Hulme, E. C., et al. (1990). "Muscarinic receptor subtypes [Review]." *Annu Rev Pharmacol Toxicol* 30: 633–73.

Huse, W. D., Sastry, L., Iverson, S. A. Kang, A. S., Alting-Mees, M. Burton, D. R., Benkovic, S. J. and Lerner, R. A. (1989). "Generation of a Large Combinatorial Library of the Immunoglobulin Repertoire in Phage Lambda." *Sci.* 346:1275–1281.

Huston, J. S., Levinson, D., Mudgett, H. M., Tai, M. S. Novotny, J., Margolies, M. N., Ridge, R. J., Bruccoleri, R. E., Haber, E., Crea, R., and Opperman, H. (1988). "Protein Engineering of antibody binding sites; recovery of specific activity in a anti-digoxin single-chain Fv analogue produced in *Escherichia coli.*" *Proc. Natl. Acad. Sci. USA* 85:5879–5883.

Imler, J. L. and G. Zurawski (1992). "Receptor binding and internalization of mouse interleukin-2 derivatives that are partial agonists." *J. Biol. Chem.* 267(19): 13185–90.

Kabat, E. A., et al. (1991). *Sequences of Proteins of Immunological Interest.* 5th edn. US Dept Health And Human Services, Bethesda, Md. USA.

Kang, A. S., Barbas, C. F., Janda, K. D., Benkovic, S. J. and Lerner, R. A. (1991). "Linkage of recognition and replication functions by assembling combinatorial antibody Fab libraries along phage surfaces." *Proc. Natl. Acad. Sci. USA*88:4363–4366.

Kaplan, D. R., Martin-Zanco, D. and Patrada, L. F. (1991). "Tyrosine phosphorylation and tyrosine kinase activity of the trk proto oncogene product induced by NGF." *Nature*, 350:156–160.

Kaplan, D. R., Martin-Zanco, D. and Patrada, L. F. (1991). "The trk proto-oncogene product: a signal transducing receptor for nerve growth factor." *Sci.* 252:554–558.

Kashihara, K., et al. (1992). "Cloning of the rat M3, M4 and M5 muscarinic acetylcholine receptor genes by the polymerase chain reaction (PCR) and the pharmacological characterization of the expressed genes." *Life Sci.* 51(12): 955–71.

Kaushansky, K. and P. A. Karplus (1993). "Hematopoietic growth factors: understanding functional diversity in structural terms. [Review]." *Blood* 82 (11): 3229–40.

Keegan, A. D., et al. (1991). "Ligand stimulation of transfected and endogenous growth factor receptors enhances cytokine production by mast cells." *Embo J.* 10(12): 3675–82.

Kelly, P. A., et al. (1991). "The prolactin/growth hormone receptor family." *Endocr Rev* 12(3): 235–51.

Kishimoto, T., et al. (1994). "Cytokine signal transduction. [Review]." *Cell* 76(2): 253–62.

Kitamura, T., et al. (1991). "Expression cloning of the human IL-3 receptor cDNA reveals a shared beta subunit for the human IL-3 and GM-CSF receptors." *Cell* 66(6): 1165–74.

Klein, R., Jing, S. Q., Nanduri, V., O'Rourke, E., and Barbacid, M. (1991). "The trk proto-oncogene encodes a receptor for nerve growth factor." *Cell* 65:189–197.

Kobayashi, I., et al. (1990). "Purification and characterization of five different alpha subunits of guanine-nucleotide-binding proteins in bovine brain membranes. Their physiological properties concerning the activities of adenylate cyclase and atrial muscarinic K+ channels." *Eur J. Biochem.* 191(2): 499–506.

Kruse, N., et al. (1992). "Conversion of human interleukin-4 into a high affinity antagonist by a single amino acid replacement." *Embo J* 11(9): 3237–44.

Kubo, T., et al. (1986). "Cloning, sequencing and expression of complementary DNA encoding the muscarinic acetylcholine receptor." *Nature* 323(6087): 411–6.

Lamden, Y., Schwartz, J. T., Wolfson, H. J. (1990). Affine invariant model-based object recognition. IEEE Trans. Robotics Automation 6(5) 578–589.

Lamden., Y., Wolfson, H. J. (1988). Geometric Hashing: A general and efficient mod el-based recognition scheme. Proc. IEEE Int. Conf. Computer Visions, Tampa, Fla. Dec. pp. 238–249.

Lazareno, S., et al. (1993). "Pharmacological characterization of guanine nucleotide exchange reactions in membranes from CHO cells stably transfected with human muscarinic receptors m1–m4. " *Life Sci.* 52(5–6): 449–56.

Lerner, R. A., Kang, A. S. Bain, J. D., Burton, D. R. and Barbas C. F. (1992). "Antibodies without immunization." *Sci.* 258:1313–1314.

Leung, D. W., et al. (1987). "Growth hormone receptor and serum binding protein: purification, cloning and expression." *Nature* 330(6148): 537–43.

Li, B. L., et al. (1989). *Prox. Natl. Acad. Sci. USA*86: 558–562.

Malby, R. L., Tulip, W. R., Harley, V. R., McKimm-Beschkin, J. L., Laver, W. G., Webster, R. G. and Colman, P. M. (1994). The structure of a complex between the NC10 antibody and influenza virus neuraminidase and comparison with the overlapping binding site of the NC41 antibody. Structure, 2(8) 733–746.

Marks, J. D., et al. (1991). "By-passing immunization. Human antibodies from V-gene libraries displayed on phage." *Journal of Molecular Biology* 222(3): 581–97.

Marks, J. D., Hoogernboom, H. J. R., Griffiths, A. D., and Winter, G. (1992). "Molecular evolution of protein on filamentous phage: mimicking the strategy of the immune system." *J. Bio. Chem.* 267:1–4.

McCafferty, J., et al. (1990). "Phage antibodies: filamentous phage displaying antibody variable domains." *Nature*348(6301): 552–4.

McCafferty, J., Griffiths, A. D., Winter, G. and Chiswell, D. J. (1990). "Phage antibodies: filamentous phage displaying antibody variable domains." *Nature* 348:552–554.

Miller, J. H. (1972). *Experiments in Molecular Genetics.* Cold Spring Harbor, N.Y., USA, Cold spring Harbor Laboratory Press.

Milstein, C. (1990); The Croonian Lecture (1989). "Antibodies: a paradigm for the biology of molecular recognition." *Prox. R. Socl. Lond. Biol.* 239:1–16.

Miranker, and A., Karplus, M. (1991). Functionality Maps of Binding Sites: A Multiple Copy Simultaneous Search Method Proteins, Structure, Function, and Genetics, 11:29–34.

Mullinax, R. L., Gross, E. A., Amberg, J. R., Hay, B. N., Hogrefe, H. H., Kubitz, M. M., Greener, A., Alting-Mees, M., Ardourel, D., Short, J. M., Sorge, J. A., and Shopes, B. (1990). "Identification of human antibody fragment clones specific for tetanus toxid in a bacteriophage λ immunoexpression library." *Proc. Natl. Acad. Sci. USA* 87:8095–8099.

Murakami, M., et al. (1991). *Proc.Natl.Acad.Sci.USA* 88: 11349–11353.

Nissim, A., Hoogenboom, H. R., Tomlinson, I. M., Flynn, G., Midgley, C., Lane, D. and Winter G. (1994). "Antibody fragments from a 'single pot' phage display library as immunochemical reagents." *EMBO J.* 13:692–698.

Nossal, G. J. (1993). "Tolerance and ways to break it." [Review]. *Ann. N.Y. Acad. Sci.* 690:34–41.

Novotny, J. Bruccoleri, R. E., Saul, F. A., (1989). On the attribution of binding energy in antigen-antibody complexes McPC603, D1.3 and HyHEL-5. Biochem. 28:4735–4749.

Obermeier, A., Halfter, H., Wiesmuller, K., Jung, G., Schlessinger, J. and Ullrich A. (1993). "Trosine 785 is a major determinant of Trk-substrate interaction." *EMBO J.* 12:933–941.

Otani, H., et al. (1992). "Interleukin (IL)-2 and IL-3 induce distinct but overlapping responses in murine IL-3-dependent 32D cells transduced with human IL-2 receptor beta chain: involvement of tyrosine kinase(s) other than p56lck." *Proc. Natl. Acad. Sci. USA* 89(7): 2789–93.

Parmely, S. F., and Smith, G. P. (1988). "Antibody-selectable filamentous fd phage vectors: affinity purification of target genes." *Gene* 73:305–318.

Patai, S. (1989). Patai's Guide to the Chemistry of Functional Groups, New York; New York, John Wiley and Sons.

Pierce, J. H., et al. (1988). "Signal transduction through the EGF receptor transfected in IL-3-dependent hematopoietic cells." *Science* 239 (4840): 628–31.

Pierce, J. H. (1989). "Oncogenes, growth factors and hematopoietic cell transformation [Review]." *Biochim Biophys Acta* 989 (2): 179–208.

Pierce, J. H., et al. (1990). "Macrophage-colony-stimulating factor (CSF-1) induces proliferation, chemotaxis, and reversible monocytic differentiation in myeloid progenitor cells transfected with the human c-fms/CSF-1 receptor cDNA." *Proc. Natl. Acad. Sci. USA* 87(15): 5613–7.

Pietzho, D., et al. (1993). "The Hepatic Interleukin-6 Receptor." *J. Biol. Chem.* 268: 4250–4258.

Poyner, D. R., et al. (1989). "Binding and hydrodynamic properties of muscarinic receptor subtypes solubilized in 3-(3-cholamidopropyl) dimethylammonio-2-hydroxy-1-propanesulfona te." *Mol Pharmacol* 36(3): 420–9.

Roitt, I. M. (1991). *Essential immunology* 7th edition, pgs 35–64. Blackwell Scientific Publications. Boston.

Rosner, J. L. (1972). "Formation, induction, and curing of bacteriophage P1 lysogens." *Virology* 48(3): 679–80.

Rozakis-Adcock, M. and P. A. Kelly (1992). "Identification of Ligand Binding Determinants of the Prolactin Receptor." *J. Biol. Chem.* 267(11): 7428–7433.

Russell, S. M., et al. (1993). "Interleukin-2 receptor gamma chain: a functional component of the interleukin-7 receptor." *Science* 262: 1880–1883.

Sambrock, J., et al. (1990). Molecular Cloning: A Laboratory Manual. Cold Spring Harbor, N.Y. USA, Cold Spring Harbor Laboratory Press.

Sastry, L., Alting-Mees, M., Huse, W. D., Short, J. M., Sorge, J. A., Hay, B. N., Handa, K. D., Benkovic, S. J. and Lerner, R. A. (1989). "Cloning of the immunological repertoire in Escherichia coli for generation of moniclonal catalytic antibodies: Construction of a heavy chain variable region-specific cDNA library." *Proc. Natl. Acad. Sci. USA* 86:5728–5732.

Scott, K. M., and Smith, G. P. (1990). "Searching for peptide ligands with an epitope library." *Sci.* 249:386–390.

Shapiro, R. A. and N. M. Nathanson (1989). "Deletion analysis of the mouse m1 muscarinic acetylcholine receptor: effects on phosphoinositide metabolism and down-regulation." *Biochemistry* 28(22): 8946–50.

Shapiro, R. A., et al. (1988). "Isolation, sequence, and functional expression of the mouse M1 muscarinic acetylcholine receptor gene [published erratum appears in J Biol Chem 1989 Apr 15;264(11): 6596]." *J. Biol. Chem.* 263(34): 18397–403.

Short, J. M., et al. (1988). *Nucleic Acid Res.* 16:7583–75.

Silva, C. M., et al. (1993). "Stimulation of tyrosine phosphorylation in human cells by activation of the growth hormone receptor." *Endocrinology* 132(1): 101–8.

Silvennoinen, O., et al. (1993). "Structure of the murine Jak2 protein-tyrosine kinase and its role in interleukin 3 signal transduction." *Proc. Natl. Acad. Sci. USA* 90(18): 8429–33.

Skerra, A., and Pluckthun, A. (1988). "Assembly of a Functional immunoglobulin Fv Fragment in *Escherichia coli.*" *Sci.* 240:1038–1041.

Smith, C. J., et al. (1987). "Guanine nucleotide modulation of muscarinic cholinergic receptor binding in postmortem human brain—a preliminary study in Alzheimer's disease." *Neurosci Lett* 82(2): 227–32.

Smith, G. P. (1985). "Filamentous fusion phage: novel expression vectors that display cloned antigens on the virions surface." *Sci.* 228:1315–1317.

Solari, R. and e. al. (1989). *Biochem J.* 262: 897–908.

Spencer, S. A., et al. (1988). "Rabbit liver growth hormone receptor and serum binding protein. Purification, characterization, and sequence." *J. Biol. Chem.* 263(16): 7862–7.

Stahl, N. and Yancopoulos, G. D., (1993). "The Alpha, Betas and Kinase: B of Cytokine Receptor Complexes." *Cell.* 74:587–590.

Sternberg, N. and D. Hamilton (1981). "Bacteriophage P1 site-specific recombination. I. Recombination between loxP sites." *Journal of Molecular Biology* 150(4): 467–86.

Sternweis, P. C. and J. D. Robishaw (1984). "Isolation of two proteins with high affinity for guanine nucleotides from membranes of bovine brain." *Journal of Biological Chemistry* 259(22): 13806–13.

Taga, T., et al. (1989). "Interleukin-6 triggers the association of its receptor with a possible signal transducer, gp130." *Cell* 58(3): 573–81.

Taga, T., et al. (1992). "Functional inhibition of hematopoietic and neurotrophic cytokines by blocking the interleukin 6 signal transducer pg130." *Proc.Natl.Acad. Sci. USA* 89: 10998–11001.

Tavernier, J., et al. (1991). "A human high affinity interleukin-5 receptor (IL5R) is composed of an IL5-specific alpha chain and a beta chain shared with the receptor for GM-CSF." *Cell* 66(6): 1175–84.

Tietje, K. M., et al. (1990). "Cloning and functional analysis of a gene encoding a novel muscarinic acetylcholine receptor expressed in chick heart and brain." *J Biol Chem* 265(5) 2828–34.

Tomlinson, I. M., Watler, G., Marks, J. D., Llewelyn, M. B. and Winter, G. (1992). "The repertoire of human germline VH sequences reveals about fifty groups of VH segments with different hypervariable loop." *J. Mol. Biol.* 227:776–798.

Tomlinson, I. M., Cook, G. P., Carter, N. P., Elaswarapu, R., Smith, S., Walter, G., Buluwela, L., Rabbits, T. H. and Winter, G. (1994). "The human immunoglobulin VH and D segments on chromosomes 15q11.2 and 16p11.2. " *Human Mol. Gen.* 3:853–860.

Tulip, W. R., Harley, V. R., Webster, R. G., Novotny, J. (1994). N9 Neuraminidase Complexes with Antibodies NC41 and NC10: Empirical Free-Energy Calculations Capture Specificity Trends Observed with Mutant Binding Data. *J. Biochemistry*, 33:7986–97.

Ullrich, A., Riedel, H J., Yarden, Y., Coussens, L., Gray, A., Dull, T., Schlessinger, J., Waterfield, M. D., Parker, P. J. (1986). "Protein kinases in cellular signal transduction: tyrosine kinase growth factor receptors and protein kinase C." *Cold Spring Harb. Symp. Quant Biol.* 2:713–724.

Ullrich, A. and Schlessinger, J. (1990) Cell 61:203–212.

van Koppen, C. J., et al. (1993). "Isolation, sequence and functional expression of the mouse m4 muscarinic acetylcholine receptor gene." *Biochim Biophys Acta* 1173(3): 342–4.

van Koppen, C. J. and N. M. Nathanson (1990). "Site-directed mutagenesis of the m2 muscarinic acetylcholine receptor. Analysis of the role of N-glycosylation in receptor expression and function." *J. Biol. Chem.* 265(34): 20887–92.

Vasudevan, S., et al. (1991). "Expression and cell membrane localizaLtion of rat M3 muscarinic acetylcholine receptor produced in Sf9 insect cells using the baculovirus system." *Febs Lett* 283(1): 52–6.

Ward, E. S., Gussow, D., Griffiths, A. D., Jones, P. T. and Winter, G. (1989). "Binding activities of a repertoire of single immunoglobulin variable domains secreted from *Escherichia coli.*" *Nature* 351:554–546.

Waterhouse, P., et al. (1993). "Combinatorial infection and in vivo recombination: a strategy for making large phage antibody repertoires." *Nucleic Acids Research*21(9): 2265–6.

Wang, H. M., et al. (1992). "Structure of mouse interleukin3 (IL-3) binding protein (AIC2A). Amino acid residues critical for IL-3 binding." *J. Biol. Chem.* 267(2): 979–83.

Webster, D. M., et al. (1994). "Antibody-antigen interactions [Review]." *Current Biology* 4: 123–129.

Weiss, A. (1993) *Cell* 73:209–212.

Weiss, J., et al. (1990). "Delineation of Muscarinic Receptor Domains Conferring Selectivity of Coupling to Guanine Nucleotide-BindirLg Proteins and Second Messengers." *Mol. Pharmacol.* 38: 517–523.

Wheatley, M., et al. (1986). *Proc. 6th International Symp. Cell and Molec. Basis Cholinergic Function:*

Williams, S. C., and Winter, G. (1993). "Cloning and sequencing of human immunoglobulin V lambda gene segments." *Eur J. Immunol.* 23:1456–1461.

Winter, G., Griffiths, A. D., Hawkings, R. E., and Hoogenboom, H. R. (1994). "Making Antibodies by phage display technology." *Annu. Rev. Immunol.* 12:433–455.

Winter, G. and Milstein C. (1991). "Man-made antibodies." *Nature* 349:293–299.

Witthuln, B. A., et al. (1993). "JAK2 associates with the erythropoietin receptor and is tyrosine phosphorylated and activated following stimulation with erythropoietin." *Cell*74 (2): 227–36.

Wu, T. T., et al. (1993). "Length Distribution of CRDH3 in Antibodies." *Proteins: Structure, Function and Genetics* 16: 1–7.

Yarmolinsky, M. B., et al. (1989). "Participation of the lytic replicon in bacteriophage P1 plasmid maintenance." *Journal of Bacteriology* 171(9): 4785–91.

Yatani, A., et al. (1988). "The G protein-gated atrial K+ channel is stimulated by three distinct Gi alpha-subunits." *Nature* 336(6200): 680–2.

Yatani, A., et al. (1990). "ras p21 and GAP inhibit coupling of muscarinic receptors to atrial K+ channels." *Cell*61(5): 769–76.

Yokota, T., et al. (1986). *Proc.Natl.Acad.Sci. USA*83: 5894–5898.

Zebedee, S. L., Barbas, C. F. 3d, Hom, Y. L., Caothien, R. H., Graff, R., DeGraw, J., Pyati, J., LaPolla, R., Burton, D. R. and Lerner, R. A. (1992). "Human combinatorial antibody libraries to hepatitis B surface antigen." *Proc. Natl. Acad. Sci. USA* 89:3175–3179.

While we have hereinbefore described a number of embodiments of this invention, it is apparent that the basic constructions can be altered to provide other embodiments which utilize the methods and compositions of this invention. Therefore, it will be appreciated that the scope of this invention is defined by the claims appended hereto rather than by the specific embodiments which have been presented hereinbefore by way of example.

I claim:

1. A method of identifying a potential drug candidate capable of binding to at least one site of a biologically active target, which site is capable of conferring a biological response, and wherein said potential drug candidate exhibits either agonist or antagonist activity at the target, the method comprising:

a) providing at least one detectable reporter of binding of said potential drug candidate to the biologically active target, wherein said reporter possesses agonist or antagonist activity at said target and wherein said reporter is selected from a recombinant library of antibodies comprising at least one variable region;

b) screening potential drug candidates by assaying for the ability of the potential drug candidates to compete with the reporter for binding to the target; and c) selecting potential drug candidates possessing agonist or antagonist activity, which compete with the reporter for binding to the target.

2. The method according to claim 1 wherein each antibody member (rVab) of the antibody library comprises at least one variable region selected from the group consisting of VH and VL regions, and optionally comprises a constant domain attached by its amino terminus to the variable region.

3. The method according to claim 2 wherein the rVab unit is displayed on the surface of a carrier.

4. The method according to claim 2 wherein the rVab unit is soluble.

5. The method according to claim 3 wherein the carrier is a bacteria.

6. The method according to claim 3 wherein the carrier is a bacteriophage.

7. The method according to claim 2 wherein a parental VL region comprising at least one CDR is used to derive the VL region of the rVab by deleting, inserting or substituting at least one amino acid within at least one CDR.

8. The method according to claim 2 wherein a parental VH region comprising at least one CDR is used to derive the VH region of the rVab by deleting, inserting or substituting at least one amino acid within at least one CDR.

9. The method according to claim 2 wherein parental VL and VH regions comprising at least one CDR, are used to derive a pair of VL and VH regions of a rVab by deleting, inserting or substituting at least one amino acid within at least one CDR of each variable region.

10. The method according to any one of claims 7, 8 or 9 wherein the crystal structure of the parental V regions used to derive rVab are known.

11. The method according to claim 9 wherein the crystal structure of the parental VH and VL pair used to derive the rVab is known.

12. The method according to claim 2 wherein at least one of the parental V regions used to derive rVab is unmodified.

13. The method according to claim 2 wherein the crystal structure of the rVab is determined after isolation as a rVab which binds to a biologically active site on the target.

14. The method according to claim 2 wherein at least two V regions are modified by deleting, inserting or substituting at least one amino acid in at least one CDR after isolation as rVab which binds to a biologically active site on the target.

15. The method according to claim 1 wherein the target is a polypeptide, protein, nucleic acid, oligosaccharide, carbohydrate or lipid.

16. The method according to claim 1 wherein target activation by the reporter is determined by assaying a biochemical response at the target which biochemical response occurs subsequent to binding of the reporter to the target and is a signal of target activation.

17. The method according to claim 16 wherein the biochemical response is detectable as a change in a protein or polypeptide characteristic.

18. The method according to claim 16 wherein the biochemical response is associated with an organometallic moiety, a metal or other nonprotein.

19. The method according to claim 16 wherein the biochemical response comprises a detectable free radical, fluorescent or chemiluminsecent group, radioactive isotope or involves oligomerization.

20. The method according to claim 16 wherein the biochemical response is phosphorylation and the signal is a change in the phosphorylation state of the target.

21. The method according to claim 17 wherein the signal protein is a G protein and the signal is a change in either the presence of a G protein regulatory agent or the binding of rVab due to the presence of a G protein regulatory agent.

22. The method according to claim 16 wherein the signal is a change in the binding affinity of rVab to its binding site.

23. The method according to claim 2 wherein the recombinant antibody comprises a single polypeptide chain comprising a VH region and a VL region which together form a binding site.

24. The method according to claim 1 wherein the target is a eukaryotic target.

25. The method according to claim 1, wherein the recombinant antibody library comprises at least $10^9$ members.

26. The method according to claim 1, wherein the recombinant antibody library comprises at least about $10^{12}$ members.

27. The method according to claim 9, wherein the parental VL and parental VH each comprise randomized amino acids at least one position of at least one CDR.

28. The method according to claim 9, wherein the parental VL region comprises a CDR1, a CDR2 and a CDR3.

29. The method according to claim 28, wherein at least one CDR comprises a multiplicity of canonical structures.

30. The method according to claim 29, wherein the CDR1 comprises five different canonical structures, CDR2 comprises one canonical structure, and CDR3 comprises six different canonical structures.

31. The method according to claim 9, wherein the parental $V_H$ region comprises a CDR1, a CDR2 and a CDR 3.

32. The method according to claim 31, wherein at least one CDR comprises a multiplicity of canonical structures.

33. The method according to claim 32, wherein CDR1 comprises three different canonical structures, CDR2 comprises four different canonical structures, and CDR3 is devoid of canonical structures.

\* \* \* \* \*